US007910331B2

(12) United States Patent
Gorman et al.

(10) Patent No.: US 7,910,331 B2
(45) Date of Patent: Mar. 22, 2011

(54) NUCLEIC ACIDS ENCODING MURINE IL-174

(75) Inventors: Daniel M. Gorman, Palo Alto, CA (US); J. Fernando Bazan, Menlo Park, CA (US); Robert A. Kastelein, Portola Valley, CA (US); Gerard Zurawski, Midlothian, TX (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 12/616,476

(22) Filed: Nov. 11, 2009

(65) Prior Publication Data
US 2010/0210012 A1    Aug. 19, 2010

Related U.S. Application Data

(60) Division of application No. 11/604,559, filed on Nov. 27, 2006, now Pat. No. 7,625,720, which is a continuation of application No. 10/742,220, filed on Dec. 19, 2003, now abandoned, which is a division of application No. 10/366,791, filed on Feb. 14, 2003, now Pat. No. 7,005,501, which is a division of application No. 09/480,297, filed on Jan. 10, 2000, now Pat. No. 6,562,578.

(60) Provisional application No. 60/115,506, filed on Jan. 11, 1999.

(51) Int. Cl.
C12N 15/09    (2006.01)
C12N 15/12    (2006.01)

(52) U.S. Cl. ............... 435/69.52; 435/320.1; 435/252.3; 435/325; 536/23.5; 530/351

(58) Field of Classification Search .................. None
See application file for complete search history.

(56) References Cited

U.S. PATENT DOCUMENTS

| 6,562,578 | B1 | 5/2003 | Gorman et al. |
| 6,569,645 | B2 | 5/2003 | Chen et al. |
| 6,579,520 | B2 | 6/2003 | Chen et al. |
| 7,005,501 | B2 | 2/2006 | Gorman et al. |
| 7,094,566 | B2 | 8/2006 | Medlock et al. |
| 7,094,886 | B2 | 8/2006 | Shaughnessy |
| 7,256,264 | B2 | 8/2007 | Goddard et al. |
| 2005/0208572 | A1 | 9/2005 | Shaughnessy |
| 2006/0078933 | A1 | 4/2006 | Medlock et al. |
| 2006/0078966 | A1 | 4/2006 | Medlock et al. |
| 2006/0078967 | A1 | 4/2006 | Medlock et al. |
| 2007/0123459 | A1 | 5/2007 | Medlock et al. |
| 2008/0085262 | A1 | 4/2008 | Gorman et al. |
| 2008/0090993 | A1 | 4/2008 | Gorman et al. |

FOREIGN PATENT DOCUMENTS

| JP | 2008278887 A | 11/2008 |
| WO | WO 95/18826 | 7/1995 |
| WO | WO 97/04097 | 2/1997 |
| WO | WO 98/49310 | 11/1998 |
| WO | WO 99/03982 | 1/1999 |
| WO | WO 99/60127 | 11/1999 |
| WO | WO 99/61617 | 12/1999 |
| WO | WO 00/15798 | 3/2000 |
| WO | WO 01/16318 | 3/2001 |
| WO | WO 02/08285 | 1/2002 |

OTHER PUBLICATIONS

Amin, Ashok R., et al.; "The role of nitric oxide in articular cartilage breakdown in osteoarthritis"; Curr. Op. Rheumatol., 10:263-268 (1998).
Birren, Bruce, et al.; "Multiple Alignment, Sequence Motifs, and Structure Inference"; Genome Analysis a Laboratory Manual; 1:574-576 (1997).
Bonaldo, M., et al.; "Human chromosome specific mRNA"; GenBank, Accession No. L23206 (Dec. 15, 1993).
Chabaud, Martine, et al.; "Enhancing Effect of IL-17 on IL-1-Induced IL-6 and Leukemia Inhibitory Factor Production by Rheumatoid Arthritis Synoviocytes and Its Regulation by Th2 Cytokines"; J. Immunol.; 161(1):409-414 (Jul. 1, 1998).
Davenport, J.W., et al.; Swiss Prot. Accession No. Q9Z1S0 (2000).
Fort, Madeline, M., et al.; "IL-25 Induces IL-4, IL-5, and IL-13 and Th2-Associated Pathologies In Vivo"; Immunity; 15:985-995 (2001).
Fossiez, Francois, et al.; "Interleukin-17"; Int. Rev. Immunol.; 16(5-6):541-551 (1998).
Hillier, L., et al.; Definition: "yv07g12.r1 Soares fetal liver spleen 1NFLS Homo sapiens cDNA clone Image:242086 5', mRNA sequence"; GenBank, Accession No. H93843 (Dec. 4, 1995).
Hillier, L., et al.; Definition: "yf25g06.r1 Soares fetal liver spleen 1NFLS Homo sapiens cDNA clone Image:127930 5', mRNA sequence"; GenBank, Accession No. R09040 (Apr. 5, 1995).
Isaacs, Neil W.; "Cystine Knots"; Curr. Op. Struct. Biol., 5:391-395 (1995).
Kennedy, Jacqueline, et al.; "Mouse IL-17: A Cytokine Preferentially Expressed by alpha beta TCR+CD4-CD8-T Cells"; J. Interferon and Cytokine Research; 16:611-617 (1996).
Kennedy, Jacqueline, et al.; Definition: "Mus Musculus IL-17 (CTLA-8) mRNA, complete cds"; GenBank, Accession No. U43088 (Jul. 31, 1996).
Kennedy, Jacqueline; Definition: "IL-17"; GenPept, Accession No. AAB05222 (Jul. 31, 1996).
Knappe, Andrea, et al.; "The Interleukin-17 Gene of Herpesvirus Saimiri"; J. Virology, 72(7):5797-5801 (Jul. 1998).
Knappe, Andrea, et al.; Definition: "Herpesvirus saimiri C-488 DNA for ORF 12 to 25"; GenBank, Accession No. Y13183 (Nov. 23, 1997).
Lee, et al.; "IL-17E, a novel proinflammatory ligand for the IL-17 receptor homolog IL-17Rh1"; J. Biol. Chem., 276(2):1660-1664 (Jan. 12, 2001).
Letuve, Severine, et al.; "IL-17E upregulates the expression of proinflammatory cytokines in lung fibroblasts"; Journal of Allergy Clin. Immunol.; 117(3):590-596 (2006).
Marra, M., et al.; Definition: "mf68b10.r1 Soares mouse embryo NbME13.5 14.5 Mus musculus cDNA clone Image:419419 5', nRNA sequence."; GenBank, Accession No. W88186 (Sep. 12, 1996).
NCI-CGAP; Definition: "ql63c10.x1 Soares_NhHMPu_S1 Homo sapiens cDNA clone Image:1877010 3'similar to contains TAR.b1 TAR1 repetitive element; mRNA sequence."; GenBank, Accession No. AI275406 (Nov. 23, 1998).
Pan, Guohua, et al.; "Forced Expression of Murine IL-17E Induces Growth Retardation, Jaundice, a Th2-Biased Response, and Multiorgan Inflammation in Mice"; The Journal of Immunology; 167:6559-6567 (2001).

(Continued)

Primary Examiner — Dong Jiang

(57) ABSTRACT

CTLA-8 related antigens from mammals, reagents related thereto including purified proteins, specific antibodies, and nucleic acids encoding said antigens. Methods of using said reagents and diagnostic kits are also provided.

11 Claims, No Drawings

OTHER PUBLICATIONS

Parkhill, J., et al.; Swiss Prot. Accession No. Q9PPE4 (2001).

Rouvier, Eric, et al.; "CTLA-8, Cloned from an Activated T Cell, Bearing AU-Rich Messenger RNA Instability Sequences, and Homologous to a Herpesvirus Saimiri Gene"; J. Immunol.; 150(12):5445-5456 (Jun. 15, 1993).

Rouvier, Eric, et al.; Definition: "Mus musculus or Rattus rattus (clone 2.6) CTLA-8 mRNA sequence, complete cds"; GenBank, Accession No. L13839 (Jul. 27, 1993).

Rouvier, Eric, et al.; Definition: "homologous to the ORF13 of Herpesvirus Saimiri"; GenPept, Accession No. AAA37490 (Jul. 27, 1993).

Seow, Heng-Fong; "Pathogen interactions with cytokines and host defence: an overview"; Vet. Immunol. Immunopath., 63:139-148 (1998.).

Soto-Prior, A., et al., Definition: "RNU74047 rat lambda ZAPII library (C. P. Hamel) Rattus norvegicus cDNA clone pC0137, mRNA sequence"; GenBank, Accession No. U74047 (Sep. 5, 1997).

Soto-Prior, A., et al., "Identification of preferentially expressed cochlear genes by systematic sequencing of rat cochlea cDNA library."; Molecular Brain Research, 47:1-10 (1997).

Sun, Peter D., et al., "The Cystine-Knot Growth-Factor Superfamily"; Annu. Rev. Biophys. Biomol. Struct., 24:269-291 (1995).

Van Kooten, Cees, et al., "Interleukin-17 Activates Human Renal Epithelial Cells in Vitro and Is Expressed during Renal Allograft Rejection"; J. Am. Soc. Nephrol., 9:1526-1534 (1998).

Wilson, et al., "2.2Mb of contiguous nucleotide sequence from chromosome III C. elegans"; Nature, 368(6466)32-38 (Mar. 3, 1994).

Yao, Zhengbin, et al., "Herpesvirus Saimiri Encodes a New Cytokine, IL-17, Which Binds to a Novel Cytokine Receptor"; Immunity, 3:811-821 (Dec. 1995).

Yao, Zhengbin, et al., "Human IL-17: A Novel Cytokine Derived from T Cells"; J. Immunol., 155:5483-5486 (1995).

Yao, Zhengbin, et al., Definition: "Human IL-17 mRNA, complete cds"; GenBank, Accession No. HSU32659, (Jan. 16, 1996).

Yao, Zhengbin, et al., Definition: "IL-17"; GenPept, Accession No. AAC50341 (Jan. 16, 1996).

SEQUENCE LISTING

```
<160> NUMBER OF SEQ ID NOS: 34

<210> SEQ ID NO 1
<211> LENGTH: 543
<212> TYPE: DNA
<213> ORGANISM: Homo sapiens
<220> FEATURE:
<221> NAME/KEY: CDS
<222> LOCATION: (1)..(540)
<223> OTHER INFORMATION:
<220> FEATURE:
<221> NAME/KEY: mat_peptide
<222> LOCATION: (61)..()
<223> OTHER INFORMATION:

<400> SEQUENCE: 1 atg gac tgg cct cac aac ctg ctg ttt ctt ctt acc att tcc atc ttc      48
Met Asp Trp Pro His Asn Leu Leu Phe Leu Leu Thr Ile Ser Ile Phe
-20              -15                  -10                  -5 ctg ggg ctg ggc cag ccc agg agc ccc aaa agc aag agg aag ggg caa      96
Leu Gly Leu Gly Gln Pro Arg Ser Pro Lys Ser Lys Arg Lys Gly Gln
         -1   1                  5                   10 ggg cgg cct ggg ccc ctg gtc cct ggc cct cac cag gtg cca ctg gac     144
```

```
Gly Arg Pro Gly Pro Leu Val Pro Gly Pro His Gln Val Pro Leu Asp
            15                  20                  25 ctg gtg tca cgg atg aaa ccg tat gcc cgc atg gag gag tat gag agg        192
Leu Val Ser Arg Met Lys Pro Tyr Ala Arg Met Glu Glu Tyr Glu Arg
     30                  35                  40 aac atc gag gag atg gtg gcc cag ctg agg aac agc tca gag ctg gcc        240
Asn Ile Glu Glu Met Val Ala Gln Leu Arg Asn Ser Ser Glu Leu Ala
 45                  50                  55                  60 cag aga aag tgt gag gtc aac ttg cag ctg tgg atg tcc aac aag agg        288
Gln Arg Lys Cys Glu Val Asn Leu Gln Leu Trp Met Ser Asn Lys Arg
                 65                  70                  75 agc ctg tct ccc tgg ggc tac agc atc aac cac gac ccc agc cgt atc        336
Ser Leu Ser Pro Trp Gly Tyr Ser Ile Asn His Asp Pro Ser Arg Ile
             80                  85                  90 ccc gtg gac ctg ccg gag gca cgg tgc ctg tgt ctg ggc tgt gtg aac        384
Pro Val Asp Leu Pro Glu Ala Arg Cys Leu Cys Leu Gly Cys Val Asn
         95                 100                 105 ccc ttc acc atg cag gag gac cgc agc atg gtg agc gtg ccg gtg ttc        432
Pro Phe Thr Met Gln Glu Asp Arg Ser Met Val Ser Val Pro Val Phe
     110                 115                 120 agc cag gtt cct gtg cgc cgc cgc ctc tgc ccg cca ccg ccc cgc aca        480
Ser Gln Val Pro Val Arg Arg Arg Leu Cys Pro Pro Pro Pro Arg Thr
125                 130                 135                 140 ggg cct tgc cgc cag cgc gca gtc atg gag acc atc gct gtg ggc tgc        528
Gly Pro Cys Arg Gln Arg Ala Val Met Glu Thr Ile Ala Val Gly Cys
                145                 150                 155 acc tgc atc ttc tga                                                    543
Thr Cys Ile Phe
            160

<210> SEQ ID NO 2
<211> LENGTH: 180
<212> TYPE: PRT
<213> ORGANISM: Homo sapiens

<400> SEQUENCE: 2

Met Asp Trp Pro His Asn Leu Leu Phe Leu Leu Thr Ile Ser Ile Phe
-20                 -15                 -10                  -5

Leu Gly Leu Gly Gln Pro Arg Ser Pro Lys Ser Lys Arg Lys Gly Gln
             -1  1                   5                  10

Gly Arg Pro Gly Pro Leu Val Pro Gly Pro His Gln Val Pro Leu Asp
            15                  20                  25

Leu Val Ser Arg Met Lys Pro Tyr Ala Arg Met Glu Glu Tyr Glu Arg
     30                  35                  40

Asn Ile Glu Glu Met Val Ala Gln Leu Arg Asn Ser Ser Glu Leu Ala
 45                  50                  55                  60

Gln Arg Lys Cys Glu Val Asn Leu Gln Leu Trp Met Ser Asn Lys Arg
                 65                  70                  75

Ser Leu Ser Pro Trp Gly Tyr Ser Ile Asn His Asp Pro Ser Arg Ile
             80                  85                  90

Pro Val Asp Leu Pro Glu Ala Arg Cys Leu Cys Leu Gly Cys Val Asn
         95                 100                 105

Pro Phe Thr Met Gln Glu Asp Arg Ser Met Val Ser Val Pro Val Phe
     110                 115                 120

Ser Gln Val Pro Val Arg Arg Arg Leu Cys Pro Pro Pro Pro Arg Thr
125                 130                 135                 140

Gly Pro Cys Arg Gln Arg Ala Val Met Glu Thr Ile Ala Val Gly Cys
                145                 150                 155
```

```
Thr Cys Ile Phe
        160

<210> SEQ ID NO 3
<211> LENGTH: 543
<212> TYPE: DNA
<213> ORGANISM: Mus musculus
<220> FEATURE:
<221> NAME/KEY: CDS
<222> LOCATION: (1)..(540)
<223> OTHER INFORMATION:
<220> FEATURE:
<221> NAME/KEY: mat_peptide
<222> LOCATION: (67)..()
<223> OTHER INFORMATION:

<400> SEQUENCE: 3 atg gac tgg ccg cac agc ctg ctc ttc ctc ctg gcc atc tcc atc ttc      48
Met Asp Trp Pro His Ser Leu Leu Phe Leu Leu Ala Ile Ser Ile Phe
        -20                 -15                 -10 ctg gcg cca agc cac ccc cgg aac acc aaa ggc aaa aga aaa ggg caa      96
Leu Ala Pro Ser His Pro Arg Asn Thr Lys Gly Lys Arg Lys Gly Gln
         -5              -1  1               5                  10 ggg agg ccc agt ccc ttg gcc cct ggg cct cat cag gtg ccg ctg gac     144
Gly Arg Pro Ser Pro Leu Ala Pro Gly Pro His Gln Val Pro Leu Asp
                 15                  20                  25 ctg gtg tct cga gta aag ccc tac gct cga atg gaa gag tat gag cgg     192
Leu Val Ser Arg Val Lys Pro Tyr Ala Arg Met Glu Glu Tyr Glu Arg
             30                  35                  40 aac ctt ggg gag atg gtg gcc cag ctg agg aac agc tcc gag cca gcc     240
Asn Leu Gly Glu Met Val Ala Gln Leu Arg Asn Ser Ser Glu Pro Ala
         45                  50                  55 aag aag aaa tgt gaa gtc aat cta cag ctg tgg ttg tcc aac aag agg     288
Lys Lys Lys Cys Glu Val Asn Leu Gln Leu Trp Leu Ser Asn Lys Arg
     60                  65                  70 agc ctg tcc cca tgg ggc tac agc atc aac cac gac ccc agc cgc atc     336
Ser Leu Ser Pro Trp Gly Tyr Ser Ile Asn His Asp Pro Ser Arg Ile
75                  80                  85                  90 cct gcg gac ttg ccc gag gcg cgg tgc cta tgt ttg ggt tgc gtg aat     384
Pro Ala Asp Leu Pro Glu Ala Arg Cys Leu Cys Leu Gly Cys Val Asn
                 95                  100                 105 ccc ttc acc atg cag gag gac cgt agc atg gtg agc gtg cca gtg ttc     432
Pro Phe Thr Met Gln Glu Asp Arg Ser Met Val Ser Val Pro Val Phe
             110                 115                 120 agc cag gtg ccg gtg cgc cgc cgc ctc tgt cct caa cct cct cgc cct     480
Ser Gln Val Pro Val Arg Arg Arg Leu Cys Pro Gln Pro Pro Arg Pro
         125                 130                 135 ggg ccc tgc cgc cag cgt gtc gtc atg gag acc atc gct gtg ggt tgc     528
Gly Pro Cys Arg Gln Arg Val Val Met Glu Thr Ile Ala Val Gly Cys
     140                 145                 150 acc tgc atc ttc tga                                                  543
Thr Cys Ile Phe
155

<210> SEQ ID NO 4
<211> LENGTH: 180
<212> TYPE: PRT
<213> ORGANISM: Mus musculus

<400> SEQUENCE: 4

Met Asp Trp Pro His Ser Leu Leu Phe Leu Leu Ala Ile Ser Ile Phe
        -20                 -15                 -10

Leu Ala Pro Ser His Pro Arg Asn Thr Lys Gly Lys Arg Lys Gly Gln
         -5              -1  1               5                  10
```

```
Gly Arg Pro Ser Pro Leu Ala Pro Gly Pro His Gln Val Pro Leu Asp
             15                  20                  25

Leu Val Ser Arg Val Lys Pro Tyr Ala Arg Met Glu Glu Tyr Glu Arg
             30                  35                  40

Asn Leu Gly Glu Met Val Ala Gln Leu Arg Asn Ser Glu Pro Ala
             45                  50                  55

Lys Lys Lys Cys Glu Val Asn Leu Gln Leu Trp Leu Ser Asn Lys Arg
 60                  65                  70

Ser Leu Ser Pro Trp Gly Tyr Ser Ile Asn His Asp Pro Ser Arg Ile
 75                  80                  85                  90

Pro Ala Asp Leu Pro Glu Ala Arg Cys Leu Cys Leu Gly Cys Val Asn
                 95                 100                 105

Pro Phe Thr Met Gln Glu Asp Arg Ser Met Val Ser Val Pro Val Phe
             110                 115                 120

Ser Gln Val Pro Val Arg Arg Leu Cys Pro Gln Pro Arg Pro
             125                 130                 135

Gly Pro Cys Arg Gln Arg Val Val Met Glu Thr Ile Ala Val Gly Cys
     140                 145                 150

Thr Cys Ile Phe
155

<210> SEQ ID NO 5
<211> LENGTH: 454
<212> TYPE: DNA
<213> ORGANISM: Homo sapiens
<220> FEATURE:
<221> NAME/KEY: CDS
<222> LOCATION: (1)..(453)
<223> OTHER INFORMATION:

<400> SEQUENCE: 5 tgc gcg gac cgg ccg gag gag cta ctg gag cag ctg tac ggg cgc ctg      48
Cys Ala Asp Arg Pro Glu Glu Leu Leu Glu Gln Leu Tyr Gly Arg Leu
 1               5                  10                  15 gcg gcc ggc gtg ctc agt gcc ttc cac cac acg ctg cag ctg ggg ccg      96
Ala Ala Gly Val Leu Ser Ala Phe His His Thr Leu Gln Leu Gly Pro
             20                  25                  30 cgt gag cag gcg cgc aac gcg agc tgc ccg gca ggg ggc agg ccc gcc     144
Arg Glu Gln Ala Arg Asn Ala Ser Cys Pro Ala Gly Gly Arg Pro Ala
         35                  40                  45 gac cgc cgc ttc cgg acg ccc acc aac ctg cgc agc gtg tcg ccc tgg     192
Asp Arg Arg Phe Arg Thr Pro Thr Asn Leu Arg Ser Val Ser Pro Trp
     50                  55                  60 gcc tac aga atc tcc tac gac ccg gcg agg tac ccc agg tac ctg cct     240
Ala Tyr Arg Ile Ser Tyr Asp Pro Ala Arg Tyr Pro Arg Tyr Leu Pro
 65                  70                  75                  80 gaa gcc tac tgc ctg tgc cgg ggc tgc ctg acc ggg ctg ttc ggc gag     288
Glu Ala Tyr Cys Leu Cys Arg Gly Cys Leu Thr Gly Leu Phe Gly Glu
                 85                  90                  95 gag gac gtg cgc ttc cgc agc gcc cct gtc tac atg ccc acc gtc gtc     336
Glu Asp Val Arg Phe Arg Ser Ala Pro Val Tyr Met Pro Thr Val Val
             100                 105                 110 ctg cgc cgc acc ccc gcc tgc gcc ggc ggc cgt tcc gtc tac acc gag     384
Leu Arg Arg Thr Pro Ala Cys Ala Gly Gly Arg Ser Val Tyr Thr Glu
         115                 120                 125 gcc tac gtc acc atc ccc gtg ggc tgc acc tgc gtc ccc gag ccg gag     432
Ala Tyr Val Thr Ile Pro Val Gly Cys Thr Cys Val Pro Glu Pro Glu
     130                 135                 140 aag gac gca gac agc atc aac t                                       454
```

```
Lys Asp Ala Asp Ser Ile Asn
145                 150

<210> SEQ ID NO 6
<211> LENGTH: 151
<212> TYPE: PRT
<213> ORGANISM: Homo sapiens

<400> SEQUENCE: 6

Cys Ala Asp Arg Pro Glu Glu Leu Leu Glu Gln Leu Tyr Gly Arg Leu
1               5                   10                  15

Ala Ala Gly Val Leu Ser Ala Phe His His Thr Leu Gln Leu Gly Pro
            20                  25                  30

Arg Glu Gln Ala Arg Asn Ala Ser Cys Pro Ala Gly Gly Arg Pro Ala
        35                  40                  45

Asp Arg Arg Phe Arg Thr Pro Thr Asn Leu Arg Ser Val Ser Pro Trp
    50                  55                  60

Ala Tyr Arg Ile Ser Tyr Asp Pro Ala Arg Tyr Pro Arg Tyr Leu Pro
65                  70                  75                  80

Glu Ala Tyr Cys Leu Cys Arg Gly Cys Leu Thr Gly Leu Phe Gly Glu
                85                  90                  95

Glu Asp Val Arg Phe Arg Ser Ala Pro Val Tyr Met Pro Thr Val Val
            100                 105                 110

Leu Arg Arg Thr Pro Ala Cys Ala Gly Gly Arg Ser Val Tyr Thr Glu
        115                 120                 125

Ala Tyr Val Thr Ile Pro Val Gly Cys Thr Cys Val Pro Glu Pro Glu
    130                 135                 140

Lys Asp Ala Asp Ser Ile Asn
145                 150

<210> SEQ ID NO 7
<211> LENGTH: 1385
<212> TYPE: DNA
<213> ORGANISM: Homo sapiens
<220> FEATURE:
<221> NAME/KEY: CDS
<222> LOCATION: (59)..(664)
<223> OTHER INFORMATION:
<220> FEATURE:
<221> NAME/KEY: mat_peptide
<222> LOCATION: (110)..()
<223> OTHER INFORMATION:

<400> SEQUENCE: 7
gcccgggcag gtggcgacct cgctcagtcg gcttctcggt ccaagtcccc gggtctgg              58 atg ctg gta gcc ggc ttc ctg ctg gcg ctg ccg ccg agc tgg gcc gcg            106
Met Leu Val Ala Gly Phe Leu Leu Ala Leu Pro Pro Ser Trp Ala Ala
        -15                 -10                 -5 ggc gcc ccg agg gcg ggc agg cgc ccc gcg cgg ccg cgg ggc tgc gcg           154
Gly Ala Pro Arg Ala Gly Arg Arg Pro Ala Arg Pro Arg Gly Cys Ala
-1  1               5                   10                  15 gac cgg ccg gag gag cta ctg gag cag ctg tac ggg cgc ctg gcg gcc           202
Asp Arg Pro Glu Glu Leu Leu Glu Gln Leu Tyr Gly Arg Leu Ala Ala
                20                  25                  30 ggc gtg ctc agt gcc ttc cac cac acg ctg cag ctg ggg ccg cgt gag           250
Gly Val Leu Ser Ala Phe His His Thr Leu Gln Leu Gly Pro Arg Glu
            35                  40                  45 cag gcg cgc aac gcg agc tgc ccg gca ggg ggc agg ccc gcc gac cgc           298
Gln Ala Arg Asn Ala Ser Cys Pro Ala Gly Gly Arg Pro Ala Asp Arg
        50                  55                  60 cgc ttc cgg ccg ccc acc aac ctg cgc agc gtg tcg ccc tgg gcc tac           346
```

```
                Arg Phe Arg Pro Pro Thr Asn Leu Arg Ser Val Ser Pro Trp Ala Tyr
                            65                  70                  75 aga atc tcc tac gac ccg gcg agg tac ccc agg tac ctg cct gaa gcc            394
Arg Ile Ser Tyr Asp Pro Ala Arg Tyr Pro Arg Tyr Leu Pro Glu Ala
 80              85                  90                  95 tac tgc ctg tgc cgg ggc tgc ctg acc ggg ctg ttc ggc gag gag gac            442
Tyr Cys Leu Cys Arg Gly Cys Leu Thr Gly Leu Phe Gly Glu Glu Asp
                100                 105                 110 gtg cgc ttc cgc agc gcc cct gtc tac atg ccc acc gtc gtc ctg cgc            490
Val Arg Phe Arg Ser Ala Pro Val Tyr Met Pro Thr Val Val Leu Arg
            115                 120                 125 cgc acc ccc gcc tgc gcc ggc ggc cgt tcc gtc tac acc gag gcc tac            538
Arg Thr Pro Ala Cys Ala Gly Gly Arg Ser Val Tyr Thr Glu Ala Tyr
        130                 135                 140 gtc acc atc ccc gtg ggc tgc acc tgc gtc ccc gag ccg gag aag gac            586
Val Thr Ile Pro Val Gly Cys Thr Cys Val Pro Glu Pro Glu Lys Asp
    145                 150                 155 gca gac agc atc aac tcc agc atc gac aaa cag ggc gcc aag ctc ctg            634
Ala Asp Ser Ile Asn Ser Ser Ile Asp Lys Gln Gly Ala Lys Leu Leu
160                 165                 170                 175 ctg ggc ccc aac gac gcg ccc gct ggc ccc tgaggccggt cctgccccgg              684
Leu Gly Pro Asn Asp Ala Pro Ala Gly Pro
                180                 185 gaggtctccc cggcccgcat cccgaggcgc ccaagctgga gccgcctgga gggctcggtc          744
ggcgacctct gaagagagtg caccgagcaa accaagtgcc ggagcaccag cgccgccttt          804
ccatggagac tcgtaagcag cttcatctga cacgggcatc cctggcttgc ttttagctac          864
aagcaagcag cgtggctgga agctgatggg aaacgacccg gcacgggcat cctgtgtgcg          924
gcccgcatgg agggtttgga aaagttcacg gaggctccct gaggagcctc tcagatcggc          984
tgctgcgggt gcagggcgtg actcaccgct gggtgcttgc aaagagata gggacgcata         1044 tgcttttttaa agcaatctaa aaataataat aagtatagcg actatatacc tacttttaaa        1104
atcaactgtt ttgaatagag gcagagctat tttatattat caaatgagag ctactctgtt         1164
acatttctta acatataaac atcgtttttt acttcttctg gtagaatttt ttaaagcata         1224
attggaatcc ttggataaat tttgtagctg gtacactctg gcctgggtct ctgaattcag         1284
cctgtcaccg atggctgact gatgaaatgg acacgtctca tctgacccac tcttccttcc        1344
actgaaggtc ttcacgggcc tccaggcctc gtgccgaatt c                             1385

<210> SEQ ID NO 8
<211> LENGTH: 202
<212> TYPE: PRT
<213> ORGANISM: Homo sapiens

<400> SEQUENCE: 8

Met Leu Val Ala Gly Phe Leu Leu Ala Leu Pro Pro Ser Trp Ala Ala
        -15                 -10                  -5

Gly Ala Pro Arg Ala Gly Arg Arg Pro Ala Arg Pro Arg Gly Cys Ala
 -1  1               5                  10                  15

Asp Arg Pro Glu Glu Leu Leu Glu Gln Leu Tyr Gly Arg Leu Ala Ala
                 20                  25                  30

Gly Val Leu Ser Ala Phe His His Thr Leu Gln Leu Gly Pro Arg Glu
             35                  40                  45

Gln Ala Arg Asn Ala Ser Cys Pro Ala Gly Gly Arg Pro Ala Asp Arg
         50                  55                  60

Arg Phe Arg Pro Pro Thr Asn Leu Arg Ser Val Ser Pro Trp Ala Tyr
     65                  70                  75
```

```
Arg Ile Ser Tyr Asp Pro Ala Arg Tyr Pro Arg Tyr Leu Pro Glu Ala
 80                  85                  90                  95

Tyr Cys Leu Cys Arg Gly Cys Leu Thr Gly Leu Phe Gly Glu Glu Asp
            100                 105                 110

Val Arg Phe Arg Ser Ala Pro Val Tyr Met Pro Thr Val Val Leu Arg
        115                 120                 125

Arg Thr Pro Ala Cys Ala Gly Gly Arg Ser Val Tyr Thr Glu Ala Tyr
    130                 135                 140

Val Thr Ile Pro Val Gly Cys Thr Cys Val Pro Glu Pro Glu Lys Asp
        145                 150                 155

Ala Asp Ser Ile Asn Ser Ser Ile Asp Lys Gln Gly Ala Lys Leu Leu
160                 165                 170                 175

Leu Gly Pro Asn Asp Ala Pro Ala Gly Pro
                180                 185

<210> SEQ ID NO 9
<211> LENGTH: 133
<212> TYPE: DNA
<213> ORGANISM: Mus musculus
<220> FEATURE:
<221> NAME/KEY: CDS
<222> LOCATION: (1)..(132)
<223> OTHER INFORMATION:

<400> SEQUENCE: 9 ttt ccg aga tac ctg ccc gaa gcc tac tgc ctg tgc cga ggc tgt ctg      48
Phe Pro Arg Tyr Leu Pro Glu Ala Tyr Cys Leu Cys Arg Gly Cys Leu
 1               5                  10                  15 acc ggg ctc tac ggt gag gag gac ttc cgc ttt cgc agc gca ccc gtc      96
Thr Gly Leu Tyr Gly Glu Glu Asp Phe Arg Phe Arg Ser Ala Pro Val
            20                  25                  30 ttc tct ccg gcg gtg gtg ctg cgg cgc acg gcg gcc t                   133
Phe Ser Pro Ala Val Val Leu Arg Arg Thr Ala Ala
        35                  40

<210> SEQ ID NO 10
<211> LENGTH: 44
<212> TYPE: PRT
<213> ORGANISM: Mus musculus

<400> SEQUENCE: 10

Phe Pro Arg Tyr Leu Pro Glu Ala Tyr Cys Leu Cys Arg Gly Cys Leu
 1               5                  10                  15

Thr Gly Leu Tyr Gly Glu Glu Asp Phe Arg Phe Arg Ser Ala Pro Val
            20                  25                  30

Phe Ser Pro Ala Val Val Leu Arg Arg Thr Ala Ala
        35                  40

<210> SEQ ID NO 11
<211> LENGTH: 1143
<212> TYPE: DNA
<213> ORGANISM: Mus musculus
<220> FEATURE:
<221> NAME/KEY: CDS
<222> LOCATION: (1)..(615)
<223> OTHER INFORMATION:
<220> FEATURE:
<221> NAME/KEY: mat_peptide
<222> LOCATION: (73)..()
<223> OTHER INFORMATION:

<400> SEQUENCE: 11 atg ttg ggg aca ctg gtc tgg atg ctc ctc gtc ggc ttc ctg ctg gca      48
```

|  |  |  |  |  |  |  |  |  |  |  |  |  |  |  |
|---|---|---|---|---|---|---|---|---|---|---|---|---|---|---|
| Met | Leu | Gly | Thr | Leu | Val | Trp | Met | Leu | Leu | Val | Gly | Phe | Leu | Leu | Ala |
|  |  |  | -20 |  |  |  |  | -15 |  |  |  |  | -10 |  |  |

| ctg | gcg | ccg | ggc | cgc | gcg | gcg | ggc | gcg | ctg | agg | acc | ggg | agg | cgc | ccg | 96 |
|---|---|---|---|---|---|---|---|---|---|---|---|---|---|---|---|---|
| Leu | Ala | Pro | Gly | Arg | Ala | Ala | Gly | Ala | Leu | Arg | Thr | Gly | Arg | Arg | Pro |  |
|  |  | -5 |  |  |  | -1 | 1 |  |  |  | 5 |  |  |  |  |  |

| gcg | cgg | ccg | cgg | gac | tgc | gcg | gac | cgg | cca | gag | gag | ctc | ctg | gag | cag | 144 |
|---|---|---|---|---|---|---|---|---|---|---|---|---|---|---|---|---|
| Ala | Arg | Pro | Arg | Asp | Cys | Ala | Asp | Arg | Pro | Glu | Glu | Leu | Leu | Glu | Gln |  |
|  | 10 |  |  |  | 15 |  |  |  |  | 20 |  |  |  |  |  |  |

| ctg | tac | ggg | cgg | ctg | gcg | gcc | ggc | gtg | ctc | agc | gcc | ttc | cac | cac | acg | 192 |
|---|---|---|---|---|---|---|---|---|---|---|---|---|---|---|---|---|
| Leu | Tyr | Gly | Arg | Leu | Ala | Ala | Gly | Val | Leu | Ser | Ala | Phe | His | His | Thr |  |
| 25 |  |  |  | 30 |  |  |  |  | 35 |  |  |  |  | 40 |  |  |

| ctg | cag | ctc | ggg | ccg | cgc | gag | cag | gcg | cgc | aat | gcc | agc | tgc | ccg | gcc | 240 |
|---|---|---|---|---|---|---|---|---|---|---|---|---|---|---|---|---|
| Leu | Gln | Leu | Gly | Pro | Arg | Glu | Gln | Ala | Arg | Asn | Ala | Ser | Cys | Pro | Ala |  |
|  |  |  |  | 45 |  |  |  |  | 50 |  |  |  |  | 55 |  |  |

| ggg | ggc | agg | gcc | gcc | gac | cgc | cgc | ttc | cgg | cca | ccc | acc | aac | ctg | cgc | 288 |
|---|---|---|---|---|---|---|---|---|---|---|---|---|---|---|---|---|
| Gly | Gly | Arg | Ala | Ala | Asp | Arg | Arg | Phe | Arg | Pro | Pro | Thr | Asn | Leu | Arg |  |
|  |  |  | 60 |  |  |  |  | 65 |  |  |  |  | 70 |  |  |  |

| agc | gtg | tcg | ccc | tgg | gcg | tac | agg | att | tcc | tac | gac | cct | gct | cgc | ttt | 336 |
|---|---|---|---|---|---|---|---|---|---|---|---|---|---|---|---|---|
| Ser | Val | Ser | Pro | Trp | Ala | Tyr | Arg | Ile | Ser | Tyr | Asp | Pro | Ala | Arg | Phe |  |
|  |  | 75 |  |  |  |  | 80 |  |  |  |  | 85 |  |  |  |  |

| ccg | agg | tac | ctg | ccc | gaa | gcc | tac | tgc | ctg | tgc | cga | ggc | tgc | ctg | acc | 384 |
|---|---|---|---|---|---|---|---|---|---|---|---|---|---|---|---|---|
| Pro | Arg | Tyr | Leu | Pro | Glu | Ala | Tyr | Cys | Leu | Cys | Arg | Gly | Cys | Leu | Thr |  |
|  | 90 |  |  |  |  | 95 |  |  |  |  | 100 |  |  |  |  |  |

| ggg | ctc | tac | ggg | gag | gag | gac | ttc | cgc | ttt | cgc | agc | aca | ccc | gtc | ttc | 432 |
|---|---|---|---|---|---|---|---|---|---|---|---|---|---|---|---|---|
| Gly | Leu | Tyr | Gly | Glu | Glu | Asp | Phe | Arg | Phe | Arg | Ser | Thr | Pro | Val | Phe |  |
| 105 |  |  |  |  | 110 |  |  |  |  | 115 |  |  |  |  | 120 |  |

| tct | cca | gcc | gtg | gtg | ctg | cgg | cgc | aca | gcg | gcc | tgc | gcg | ggc | ggc | cgc | 480 |
|---|---|---|---|---|---|---|---|---|---|---|---|---|---|---|---|---|
| Ser | Pro | Ala | Val | Val | Leu | Arg | Arg | Thr | Ala | Ala | Cys | Ala | Gly | Gly | Arg |  |
|  |  |  |  | 125 |  |  |  |  | 130 |  |  |  |  | 135 |  |  |

| tct | gtg | tac | gcc | gaa | cac | tac | atc | acc | atc | ccg | gtg | ggc | tgc | acc | tgc | 528 |
|---|---|---|---|---|---|---|---|---|---|---|---|---|---|---|---|---|
| Ser | Val | Tyr | Ala | Glu | His | Tyr | Ile | Thr | Ile | Pro | Val | Gly | Cys | Thr | Cys |  |
|  |  | 140 |  |  |  |  | 145 |  |  |  |  | 150 |  |  |  |  |

| gtg | ccc | gag | ccg | gac | aag | tcc | gcg | gac | agt | gcg | aac | tcc | agc | atg | gac | 576 |
|---|---|---|---|---|---|---|---|---|---|---|---|---|---|---|---|---|
| Val | Pro | Glu | Pro | Asp | Lys | Ser | Ala | Asp | Ser | Ala | Asn | Ser | Ser | Met | Asp |  |
|  |  | 155 |  |  |  |  | 160 |  |  |  |  | 165 |  |  |  |  |

| aag | ctg | ctg | ctg | ggg | ccc | gcc | gac | agg | cct | gcg | ggg | cgc | tgatgccggg | 625 |
|---|---|---|---|---|---|---|---|---|---|---|---|---|---|---|
| Lys | Leu | Leu | Leu | Gly | Pro | Ala | Asp | Arg | Pro | Ala | Gly | Arg |  |  |
| 170 |  |  |  |  | 175 |  |  |  |  | 180 |  |  |  |  |

| gactgcccgc | catggcccag | cttcctgcat | gcatcaggtc | ccctggccct | gacaaaaccc | 685 |
|---|---|---|---|---|---|---|
| acccccatgat | ccctggccgc | tgcctaattt | ttccaaaagg | acagctacat | aagctttaaa | 745 |
| tatattttc | aaagtagaca | ctacatatct | acaactattt | tgaatagtgg | cagaaactat | 805 |
| tttcatatta | gtaatttaga | gcaagcatgt | tgttttaaa | cttctttgat | atacaagcac | 865 |
| atcacacaca | tcccgttttc | ctctagtagg | attcttgagt | gcataattgt | agtgctcaga | 925 |
| tgaacttcct | tctgctgcac | tgtgccctgt | ccctgagtct | ctcctgtggc | ccaagcttac | 985 |
| taaggtgata | atgagtgctc | cggatctggg | cacctaaggt | ctccaggtcc | ctggagaggg | 1045 |
| agggatgtgg | gggggctagg | aaccaagcgc | ccctttgttc | tttagcttat | ggatggtctt | 1105 |
| aactttataa | agattaaagt | ttttggtgtt | attctttc |  |  | 1143 |

<210> SEQ ID NO 12
<211> LENGTH: 205
<212> TYPE: PRT
<213> ORGANISM: Mus musculus

<400> SEQUENCE: 12

|  |  |  |  |  |  |  |  |  |  |  |  |  |  |  |
|---|---|---|---|---|---|---|---|---|---|---|---|---|---|---|
| Met | Leu | Gly | Thr | Leu | Val | Trp | Met | Leu | Leu | Val | Gly | Phe | Leu | Leu | Ala |
|  |  |  | -20 |  |  |  |  | -15 |  |  |  |  | -10 |  |  |

```
Leu Ala Pro Gly Arg Ala Ala Gly Ala Leu Arg Thr Gly Arg Arg Pro
         -5              -1  1               5

Ala Arg Pro Arg Asp Cys Ala Asp Arg Pro Glu Glu Leu Leu Glu Gln
         10              15              20

Leu Tyr Gly Arg Leu Ala Ala Gly Val Leu Ser Ala Phe His His Thr
25              30              35              40

Leu Gln Leu Gly Pro Arg Glu Gln Ala Arg Asn Ala Ser Cys Pro Ala
             45              50              55

Gly Gly Arg Ala Ala Asp Arg Arg Phe Arg Pro Thr Asn Leu Arg
             60              65              70

Ser Val Ser Pro Trp Ala Tyr Arg Ile Ser Tyr Asp Pro Ala Arg Phe
         75              80              85

Pro Arg Tyr Leu Pro Glu Ala Tyr Cys Leu Cys Arg Gly Cys Leu Thr
         90              95              100

Gly Leu Tyr Gly Glu Glu Asp Phe Arg Phe Arg Ser Thr Pro Val Phe
105             110             115             120

Ser Pro Ala Val Val Leu Arg Arg Thr Ala Ala Cys Ala Gly Gly Arg
                 125             130             135

Ser Val Tyr Ala Glu His Tyr Ile Thr Ile Pro Val Gly Cys Thr Cys
         140             145             150

Val Pro Glu Pro Asp Lys Ser Ala Asp Ser Ala Asn Ser Ser Met Asp
         155             160             165

Lys Leu Leu Leu Gly Pro Ala Asp Arg Pro Ala Gly Arg
         170             175             180

<210> SEQ ID NO 13
<211> LENGTH: 504
<212> TYPE: DNA
<213> ORGANISM: Homo sapiens
<220> FEATURE:
<221> NAME/KEY: CDS
<222> LOCATION: (19)..(501)
<223> OTHER INFORMATION:
<220> FEATURE:
<221> NAME/KEY: mat_peptide
<222> LOCATION: (67)..()
<223> OTHER INFORMATION:

<400> SEQUENCE: 13
tgagtgtgca gtgccagc atg tac cag gtg gtt gca ttc ttg gca atg gtc        51
                    Met Tyr Gln Val Val Ala Phe Leu Ala Met Val
                        -15                     -10 atg gga acc cac acc tac agc cac tgg ccc agc tgc tgc ccc agc aaa        99
Met Gly Thr His Thr Tyr Ser His Trp Pro Ser Cys Cys Pro Ser Lys
-5              -1  1               5                   10 ggg cag gac acc tct gag gag ctg ctg agg tgg agc act gtg cct gtg       147
Gly Gln Asp Thr Ser Glu Glu Leu Leu Arg Trp Ser Thr Val Pro Val
             15              20              25 cct ccc cta gag cct gct agg ccc aac cgc cac cca gag tcc tgt agg       195
Pro Pro Leu Glu Pro Ala Arg Pro Asn Arg His Pro Glu Ser Cys Arg
         30              35              40 gcc agt gaa gat gga ccc ctc aac agc agg gcc atc tcc ccc tgg aga       243
Ala Ser Glu Asp Gly Pro Leu Asn Ser Arg Ala Ile Ser Pro Trp Arg
         45              50              55 tat gag ttg gac aga gac ttg aac cgg ctc ccc cag gac ctg tac cac       291
Tyr Glu Leu Asp Arg Asp Leu Asn Arg Leu Pro Gln Asp Leu Tyr His
60              65              70              75 gcc cgt tgc ctg tgc ccg cac tgc gtc agc cta cag aca ggc tcc cac       339
Ala Arg Cys Leu Cys Pro His Cys Val Ser Leu Gln Thr Gly Ser His
             80              85              90
```

| | | | | | | | | | | | | | | | |
|---|---|---|---|---|---|---|---|---|---|---|---|---|---|---|---|
| atg | gac | ccc | cgg | ggc | aac | tcg | gag | ctg | ctc | tac | cac | aac | cag | act | gtc | 387 |
| Met | Asp | Pro | Arg | Gly | Asn | Ser | Glu | Leu | Leu | Tyr | His | Asn | Gln | Thr | Val |
| | | 95 | | | | | 100 | | | | | 105 | | | |

| | | | | | | | | | | | | | | | |
|---|---|---|---|---|---|---|---|---|---|---|---|---|---|---|---|
| ttc | tac | cgg | cgg | cca | tgc | cat | ggc | gag | aag | ggc | acc | cac | aag | ggc | tac | 435 |
| Phe | Tyr | Arg | Arg | Pro | Cys | His | Gly | Glu | Lys | Gly | Thr | His | Lys | Gly | Tyr |
| 110 | | | | | 115 | | | | | 120 | | | | | |

| | | | | | | | | | | | | | | | |
|---|---|---|---|---|---|---|---|---|---|---|---|---|---|---|---|
| tgc | ctg | gag | cgc | agg | ctg | tac | cgt | gtt | tcc | tta | gct | tgt | gtg | tgt | gtg | 483 |
| Cys | Leu | Glu | Arg | Arg | Leu | Tyr | Arg | Val | Ser | Leu | Ala | Cys | Val | Cys | Val |
| | 125 | | | | | 130 | | | | | 135 | | | | |

| | | | | | |
|---|---|---|---|---|---|
| cgg | ccc | cgt | gtg | atg | ggc tag | 504 |
| Arg | Pro | Arg | Val | Met | Gly |
| 140 | | | | 145 | |

<210> SEQ ID NO 14
<211> LENGTH: 161
<212> TYPE: PRT
<213> ORGANISM: Homo sapiens

<400> SEQUENCE: 14

Met Tyr Gln Val Val Ala Phe Leu Ala Met Val Met Gly Thr His Thr
     -15             -10              -5               -1

Tyr Ser His Trp Pro Ser Cys Cys Pro Ser Lys Gly Gln Asp Thr Ser
 1               5              10                  15

Glu Glu Leu Leu Arg Trp Ser Thr Val Pro Val Pro Pro Leu Glu Pro
            20              25              30

Ala Arg Pro Asn Arg His Pro Glu Ser Cys Arg Ala Ser Glu Asp Gly
         35              40              45

Pro Leu Asn Ser Arg Ala Ile Ser Pro Trp Arg Tyr Glu Leu Asp Arg
 50              55              60

Asp Leu Asn Arg Leu Pro Gln Asp Leu Tyr His Ala Arg Cys Leu Cys
 65              70              75              80

Pro His Cys Val Ser Leu Gln Thr Gly Ser His Met Asp Pro Arg Gly
             85              90              95

Asn Ser Glu Leu Leu Tyr His Asn Gln Thr Val Phe Tyr Arg Arg Pro
           100             105             110

Cys His Gly Glu Lys Gly Thr His Lys Gly Tyr Cys Leu Glu Arg Arg
         115             120             125

Leu Tyr Arg Val Ser Leu Ala Cys Val Cys Val Arg Pro Arg Val Met
     130             135             140

Gly
145

<210> SEQ ID NO 15
<211> LENGTH: 620
<212> TYPE: DNA
<213> ORGANISM: Mus musculus
<220> FEATURE:
<221> NAME/KEY: CDS
<222> LOCATION: (1)..(432)
<223> OTHER INFORMATION:

<400> SEQUENCE: 15

| | | | | | | | | | | | | | | | |
|---|---|---|---|---|---|---|---|---|---|---|---|---|---|---|---|
| cgg | cac | agg | cgg | cac | aaa | gcc | cgg | aga | gtg | gct | gaa | gtg | gag | ctc | tgc | 48 |
| Arg | His | Arg | Arg | His | Lys | Ala | Arg | Arg | Val | Ala | Glu | Val | Glu | Leu | Cys |
| 1 | | | | 5 | | | | | 10 | | | | | 15 | |

| | | | | | | | | | | | | | | | |
|---|---|---|---|---|---|---|---|---|---|---|---|---|---|---|---|
| atc | tgt | atc | ccc | ccc | aga | gcc | tct | gag | cca | cac | cca | cca | cgc | aga | atc | 96 |
| Ile | Cys | Ile | Pro | Pro | Arg | Ala | Ser | Glu | Pro | His | Pro | Pro | Arg | Arg | Ile |
| | | | 20 | | | | | 25 | | | | | 30 | | |

| | | | | | | | | | | | | | | | |
|---|---|---|---|---|---|---|---|---|---|---|---|---|---|---|---|
| ctg | cag | ggc | cag | caa | gga | tgg | cct | ctc | aac | agc | agg | gcc | atc | tct | cct | 144 |
| Leu | Gln | Gly | Gln | Gln | Gly | Trp | Pro | Leu | Asn | Ser | Arg | Ala | Ile | Ser | Pro |
| | 35 | | | | | 40 | | | | | 45 | | | | |

```
tgg agc tat gag ttg gac agg gac ttg aat cgg gtc ccc cag gac tgg      192
Trp Ser Tyr Glu Leu Asp Arg Asp Leu Asn Arg Val Pro Gln Asp Trp
 50                  55                  60 tac cac gct cga tgc ctg tgc cca cac tgc gtc acg cta cag aca ggc      240
Tyr His Ala Arg Cys Leu Cys Pro His Cys Val Thr Leu Gln Thr Gly
 65                  70                  75                  80 tcc cac atg gac ccg ctg ggc aac tcc gtc cca ctt tac cac aac cag      288
Ser His Met Asp Pro Leu Gly Asn Ser Val Pro Leu Tyr His Asn Gln
                 85                  90                  95 acg gtc ttc tac cgg cgg cca tgc atg gcg agg aag gta ccc atc gcc      336
Thr Val Phe Tyr Arg Arg Pro Cys Met Ala Arg Lys Val Pro Ile Ala
            100                 105                 110 gct act gct tgg agc gca ggt cta ccg agt ctc ctt ggc ttg tgt gtg      384
Ala Thr Ala Trp Ser Ala Gly Leu Pro Ser Leu Leu Gly Leu Cys Val
        115                 120                 125 tgt gcg gcc ccg ggt cat ggc tta gtc atg ctc acc atc tgc ctg agg      432
Cys Ala Ala Pro Gly His Gly Leu Val Met Leu Thr Ile Cys Leu Arg
    130                 135                 140 tgaatgccgg gtgggagaga gggccaggtg tacatcacct gccaatgcgg gccgggttca    492
agcctgcaaa gcctacctga agcagcaggt cccgggacag gatggagact tggggagaaa    552
tctgactttt gcactttttg gagcattttg ggaagagcag gttcgcttgt gctgtagaga    612
tgctgttg                                                              620

<210> SEQ ID NO 16
<211> LENGTH: 144
<212> TYPE: PRT
<213> ORGANISM: Mus musculus

<400> SEQUENCE: 16

Arg His Arg Arg His Lys Ala Arg Arg Val Ala Glu Val Glu Leu Cys
 1               5                  10                  15

Ile Cys Ile Pro Pro Arg Ala Ser Glu Pro His Pro Pro Arg Arg Ile
            20                  25                  30

Leu Gln Gly Gln Gln Gly Trp Pro Leu Asn Ser Arg Ala Ile Ser Pro
        35                  40                  45

Trp Ser Tyr Glu Leu Asp Arg Asp Leu Asn Arg Val Pro Gln Asp Trp
 50                  55                  60

Tyr His Ala Arg Cys Leu Cys Pro His Cys Val Thr Leu Gln Thr Gly
 65                  70                  75                  80

Ser His Met Asp Pro Leu Gly Asn Ser Val Pro Leu Tyr His Asn Gln
                 85                  90                  95

Thr Val Phe Tyr Arg Arg Pro Cys Met Ala Arg Lys Val Pro Ile Ala
            100                 105                 110

Ala Thr Ala Trp Ser Ala Gly Leu Pro Ser Leu Leu Gly Leu Cys Val
        115                 120                 125

Cys Ala Ala Pro Gly His Gly Leu Val Met Leu Thr Ile Cys Leu Arg
    130                 135                 140

<210> SEQ ID NO 17
<211> LENGTH: 985
<212> TYPE: DNA
<213> ORGANISM: Mus musculus
<220> FEATURE:
<221> NAME/KEY: CDS
<222> LOCATION: (1)..(507)
<223> OTHER INFORMATION:
<220> FEATURE:
<221> NAME/KEY: mat_peptide
<222> LOCATION: (49)..()
```

<223> OTHER INFORMATION:

<400> SEQUENCE: 17

```
atg tac cag gct gtt gca ttc ttg gca atg atc gtg gga acc cac acc        48
Met Tyr Gln Ala Val Ala Phe Leu Ala Met Ile Val Gly Thr His Thr
    -15                 -10                 -5                  -1 gtc agc ttg cgg atc cag gag ggc tgc agt cac ttg ccc agc tgc tgc        96
Val Ser Leu Arg Ile Gln Glu Gly Cys Ser His Leu Pro Ser Cys Cys
1               5                   10                  15 ccc agc aaa gag caa gaa ccc ccg gag gag tgg ctg aag tgg agc tct       144
Pro Ser Lys Glu Gln Glu Pro Pro Glu Glu Trp Leu Lys Trp Ser Ser
            20                  25                  30 gca tct gtg tcc ccc cca gag cct ctg agc cac acc cac cac gca gaa       192
Ala Ser Val Ser Pro Pro Glu Pro Leu Ser His Thr His His Ala Glu
        35                  40                  45 tcc tgc agg gcc agc aag gat ggc ccc ctc aac agc agg gcc atc tct       240
Ser Cys Arg Ala Ser Lys Asp Gly Pro Leu Asn Ser Arg Ala Ile Ser
    50                  55                  60 cct tgg agc tat gag ttg gac agg gac ttg aat cgg gtc ccc cag gac       288
Pro Trp Ser Tyr Glu Leu Asp Arg Asp Leu Asn Arg Val Pro Gln Asp
65                  70                  75                  80 ctg tac cac gct cga tgc ctg tgc cca cac tgc gtc agc cta cag aca       336
Leu Tyr His Ala Arg Cys Leu Cys Pro His Cys Val Ser Leu Gln Thr
                85                  90                  95 ggc tcc cac atg gac ccg ctg ggc aac tcc gtc cca ctt tac cac aac       384
Gly Ser His Met Asp Pro Leu Gly Asn Ser Val Pro Leu Tyr His Asn
            100                 105                 110 cag acg gtc ttc tac cgg cgg cca tgc cat ggt gag gaa ggt acc cat       432
Gln Thr Val Phe Tyr Arg Arg Pro Cys His Gly Glu Glu Gly Thr His
        115                 120                 125 cgc cgc tac tgc ttg gag cgc agg ctc tac cga gtc tcc ttg gct tgt       480
Arg Arg Tyr Cys Leu Glu Arg Arg Leu Tyr Arg Val Ser Leu Ala Cys
    130                 135                 140 gtg tgt gtg cgg ccc cgg gtc atg gct tagtcatgct caccacctgc             527
Val Cys Val Arg Pro Arg Val Met Ala
145                 150 ctgaggctga tgcccggttg ggagagaggg ccaggtgtac aatcaccttg ccaatgcggg      587
ccgggttcaa gccctccaaa gccctacctg aagcagcagg ctcccgggac aagatggagg      647
acttggggag aaactctgac ttttgcactt ttggaagca cttttgggaa ggagcaggtt       707
ccgcttgtgc tgctagagga tgctgttgtg gcatttctac tcaggaacgg actccaaagg     767
cctgctgacc ctgaagcca tactcctggc tcctttcccc tgaatccccc aactcctggc      827
acaggcactt tctccacctc tcccccttg ccttttgttg tgtttgtttg tgcatgccaa      887
ctctgcgtgc agccaggtgt aattgccttg aaggatggtt ctgaggtgaa agctgttatc     947
gaaagtgaag agatttatcc aaataaacat ctgtgttt                             985
```

<210> SEQ ID NO 18
<211> LENGTH: 169
<212> TYPE: PRT
<213> ORGANISM: Mus musculus

<400> SEQUENCE: 18

```
Met Tyr Gln Ala Val Ala Phe Leu Ala Met Ile Val Gly Thr His Thr
    -15                 -10                 -5                  -1

Val Ser Leu Arg Ile Gln Glu Gly Cys Ser His Leu Pro Ser Cys Cys
1               5                   10                  15

Pro Ser Lys Glu Gln Glu Pro Pro Glu Glu Trp Leu Lys Trp Ser Ser
            20                  25                  30
```

```
Ala Ser Val Ser Pro Pro Glu Pro Leu Ser His Thr His His Ala Glu
        35                  40                  45

Ser Cys Arg Ala Ser Lys Asp Gly Pro Leu Asn Ser Arg Ala Ile Ser
 50                  55                  60

Pro Trp Ser Tyr Glu Leu Asp Arg Asp Leu Asn Arg Val Pro Gln Asp
 65                  70                  75                  80

Leu Tyr His Ala Arg Cys Leu Cys Pro His Cys Val Ser Leu Gln Thr
                 85                  90                  95

Gly Ser His Met Asp Pro Leu Gly Asn Ser Val Pro Leu Tyr His Asn
                100                 105                 110

Gln Thr Val Phe Tyr Arg Arg Pro Cys His Gly Glu Glu Gly Thr His
            115                 120                 125

Arg Arg Tyr Cys Leu Glu Arg Arg Leu Tyr Arg Val Ser Leu Ala Cys
        130                 135                 140

Val Cys Val Arg Pro Arg Val Met Ala
145                 150
```

<210> SEQ ID NO 19
<211> LENGTH: 521
<212> TYPE: DNA
<213> ORGANISM: Homo sapiens
<220> FEATURE:
<221> NAME/KEY: misc_feature
<222> LOCATION: (281)..(281)
<223> OTHER INFORMATION: unknown amino
<220> FEATURE:
<221> NAME/KEY: misc_feature
<222> LOCATION: (367)..(367)
<223> OTHER INFORMATION: unkonwn amino
<220> FEATURE:
<221> NAME/KEY: misc_feature
<222> LOCATION: (437)..(437)
<223> OTHER INFORMATION: unknown amino
<220> FEATURE:
<221> NAME/KEY: misc_feature
<222> LOCATION: (462)..(462)
<223> OTHER INFORMATION: unknown amino
<220> FEATURE:
<221> NAME/KEY: misc_feature
<222> LOCATION: (468)..(468)
<223> OTHER INFORMATION: unknown amino

<400> SEQUENCE: 19

```
gacacggatg aggaccgcta tccacagaag ctggccttcg ccgagtgcct gtgcagaggc    60
tgtatcgatg cacggacggg ccgcgagaca gctgcgctca actccgtgcg gctgctccag   120
agcctgctgg tgctgcgccg ccggccctgc tcccgcgacg gctcggggct ccccacacct   180
ggggcctttg ccttccacac cgagttcatc cacgtccccg tcggctgcac ctgcgtgctg   240
ccccgttcaa gtgtgaccgc caaggccgtg gggcccttag ntgacaccgt gtgctcccca   300
gagggacccc tatttatggg aattatggta ttatatgctt cccacatact tggggctggc   360
atcccgngct gagacagccc cctgttctat tcagctatat ggggagaaga gtagactttc   420
agctaagtga aaagtgnaac gtgctgactg tctgctgtcg tnctactnat gctagcccga   480
gtgttcactc tgagcctgtt aaatataggc ggttatgtac c                       521
```

<210> SEQ ID NO 20
<211> LENGTH: 521
<212> TYPE: DNA
<213> ORGANISM: Homo sapiens
<220> FEATURE:
<221> NAME/KEY: CDS
<222> LOCATION: (1)..(369)
<223> OTHER INFORMATION:

```
<220> FEATURE:
<221> NAME/KEY: misc_feature
<222> LOCATION: (281)..(281)
<223> OTHER INFORMATION: unkown amino
<220> FEATURE:
<221> NAME/KEY: misc_feature
<222> LOCATION: (367)..(367)
<223> OTHER INFORMATION: unknown amino
<220> FEATURE:
<221> NAME/KEY: misc_feature
<222> LOCATION: (437)..(437)
<223> OTHER INFORMATION: unknown amino
<220> FEATURE:
<221> NAME/KEY: misc_feature
<222> LOCATION: (462)..(462)
<223> OTHER INFORMATION: unknown amino
<220> FEATURE:
<221> NAME/KEY: misc_feature
<222> LOCATION: (468)..(468)
<223> OTHER INFORMATION: unknown amino

<400> SEQUENCE: 20 gac acg gat gag gac cgc tat cca cag aag ctg gcc ttc gcc gag tgc     48
Asp Thr Asp Glu Asp Arg Tyr Pro Gln Lys Leu Ala Phe Ala Glu Cys
1               5                   10                  15 ctg tgc aga ggc tgt atc gat gca cgg acg ggc cgc gag aca gct gcg     96
Leu Cys Arg Gly Cys Ile Asp Ala Arg Thr Gly Arg Glu Thr Ala Ala
            20                  25                  30 ctc aac tcc gtg cgg ctg ctc cag agc ctg ctg gtg ctg cgc cgc cgg    144
Leu Asn Ser Val Arg Leu Leu Gln Ser Leu Leu Val Leu Arg Arg Arg
        35                  40                  45 ccc tgc tcc cgc gac ggc tcg ggg ctc ccc aca cct ggg gcc ttt gcc    192
Pro Cys Ser Arg Asp Gly Ser Gly Leu Pro Thr Pro Gly Ala Phe Ala
 50                  55                  60 ttc cac acc gag ttc atc cac gtc ccc gtc ggc tgc acc tgc gtg ctg    240
Phe His Thr Glu Phe Ile His Val Pro Val Gly Cys Thr Cys Val Leu
65                  70                  75                  80 ccc cgt tca agt gtg acc gcc aag gcc gtg ggg ccc tta gnt gac acc    288
Pro Arg Ser Ser Val Thr Ala Lys Ala Val Gly Pro Leu Xaa Asp Thr
                85                  90                  95 gtg tgc tcc cca gag gga ccc cta ttt atg gga att atg gta tta tat    336
Val Cys Ser Pro Glu Gly Pro Leu Phe Met Gly Ile Met Val Leu Tyr
            100                 105                 110 gct tcc cac ata ctt ggg gct ggc atc ccg ngc tgagacagcc cctgttcta   389
Ala Ser His Ile Leu Gly Ala Gly Ile Pro Xaa
        115                 120 ttcagctata tggggagaag agtagacttt cagctaagtg aaaagtgnaa cgtgctgact  449
gtctgctgtc gtnctactna tgctagcccg agtgttcact ctgagcctgt taaatatagg  509
cggttatgta cc                                                      521

<210> SEQ ID NO 21
<211> LENGTH: 123
<212> TYPE: PRT
<213> ORGANISM: Homo sapiens
<220> FEATURE:
<221> NAME/KEY: misc_feature
<222> LOCATION: (94)..(94)
<223> OTHER INFORMATION: The 'Xaa' at location 94 stands for Asp, Gly,
      Ala, or Val.
<220> FEATURE:
<221> NAME/KEY: misc_feature
<222> LOCATION: (123)..(123)
<223> OTHER INFORMATION: The 'Xaa' at location 123 stands for Ser, Gly,
      Arg, or Cys.
<220> FEATURE:
<221> NAME/KEY: misc_feature
<222> LOCATION: (281)..(281)
<223> OTHER INFORMATION: unkown amino
```

```
<220> FEATURE:
<221> NAME/KEY: misc_feature
<222> LOCATION: (367)..(367)
<223> OTHER INFORMATION: unknown amino
<220> FEATURE:
<221> NAME/KEY: misc_feature
<222> LOCATION: (437)..(437)
<223> OTHER INFORMATION: unknown amino
<220> FEATURE:
<221> NAME/KEY: misc_feature
<222> LOCATION: (462)..(462)
<223> OTHER INFORMATION: unknown amino
<220> FEATURE:
<221> NAME/KEY: misc_feature
<222> LOCATION: (468)..(468)
<223> OTHER INFORMATION: unknown amino

<400> SEQUENCE: 21

Asp Thr Asp Glu Asp Arg Tyr Pro Gln Lys Leu Ala Phe Ala Glu Cys
1               5                   10                  15

Leu Cys Arg Gly Cys Ile Asp Ala Arg Thr Gly Arg Glu Thr Ala Ala
            20                  25                  30

Leu Asn Ser Val Arg Leu Leu Gln Ser Leu Leu Val Leu Arg Arg Arg
        35                  40                  45

Pro Cys Ser Arg Asp Gly Ser Gly Leu Pro Thr Pro Gly Ala Phe Ala
    50                  55                  60

Phe His Thr Glu Phe Ile His Val Pro Val Gly Cys Thr Cys Val Leu
65                  70                  75                  80

Pro Arg Ser Ser Val Thr Ala Lys Ala Val Gly Pro Leu Xaa Asp Thr
                85                  90                  95

Val Cys Ser Pro Glu Gly Pro Leu Phe Met Gly Ile Met Val Leu Tyr
            100                 105                 110

Ala Ser His Ile Leu Gly Ala Gly Ile Pro Xaa
        115                 120

<210> SEQ ID NO 22
<211> LENGTH: 1107
<212> TYPE: DNA
<213> ORGANISM: Homo sapiens
<220> FEATURE:
<221> NAME/KEY: CDS
<222> LOCATION: (115)..(705)
<223> OTHER INFORMATION:
<220> FEATURE:
<221> NAME/KEY: mat_peptide
<222> LOCATION: (166)..()
<223> OTHER INFORMATION:

<400> SEQUENCE: 22
gtgtggcctc aggtataaga gcggctgctg ccaggtgcat ggccaggtgc acctgtggga      60
ttgccgccag gtgtgcaggc cgctccaagc ccagcctgcc ccgctgccgc cacc atg     117
                                                              Met acg ctc ctc ccc ggc ctc ctg ttt ctg acc tgg ctg cac aca tgc ctg     165
Thr Leu Leu Pro Gly Leu Leu Phe Leu Thr Trp Leu His Thr Cys Leu
    -15             -10                 -5                  -1 gcc cac cat gac ccc tcc ctc agg ggg cac ccc cac agt cac ggt acc     213
Ala His His Asp Pro Ser Leu Arg Gly His Pro His Ser His Gly Thr
1               5                   10                  15 cca cac tgc tac tcg gct gag gaa ctg ccc ctc ggc cag gcc ccc        261
Pro His Cys Tyr Ser Ala Glu Glu Leu Pro Leu Gly Gln Ala Pro Pro
            20                  25                  30 cac ctg ctg gct cga ggt gcc aag tgg ggg cag gct ttg cct gta gcc     309
His Leu Leu Ala Arg Gly Ala Lys Trp Gly Gln Ala Leu Pro Val Ala
        35                  40                  45
```

```
ctg gtg tcc agc ctg gag gca gca agc cac agg ggg agg cac gag agg     357
Leu Val Ser Ser Leu Glu Ala Ala Ser His Arg Gly Arg His Glu Arg
     50                  55                  60 ccc tca gct acg acc cag tgc ccg gtg ctg cgg ccg gag gag gtg ttg     405
Pro Ser Ala Thr Thr Gln Cys Pro Val Leu Arg Pro Glu Glu Val Leu
 65                  70                  75                  80 gag gca gac acc cac cag cgc tcc atc tca ccc tgg aga tac cgt gtg     453
Glu Ala Asp Thr His Gln Arg Ser Ile Ser Pro Trp Arg Tyr Arg Val
                 85                  90                  95 gac acg gat gag gac cgc tat cca cag aag ctg gcc ttc gcc gag tgc     501
Asp Thr Asp Glu Asp Arg Tyr Pro Gln Lys Leu Ala Phe Ala Glu Cys
             100                 105                 110 ctg tgc aga ggc tgt atc gat gca cgg acg ggc cgc gag aca gct gcg     549
Leu Cys Arg Gly Cys Ile Asp Ala Arg Thr Gly Arg Glu Thr Ala Ala
         115                 120                 125 ctc aac tcc gtg cgg ctg ctc cag agc ctg ctg gtg ctg cgc cgc cgg     597
Leu Asn Ser Val Arg Leu Leu Gln Ser Leu Leu Val Leu Arg Arg Arg
     130                 135                 140 ccc tgc tcc cgc gac ggc tcg ggg ctc ccc aca cct ggg gcc ttt gcc     645
Pro Cys Ser Arg Asp Gly Ser Gly Leu Pro Thr Pro Gly Ala Phe Ala
145                 150                 155                 160 ttc cac acc gag ttc atc cac gtc ccc gtc ggc tgc acc tgc gtg ctg     693
Phe His Thr Glu Phe Ile His Val Pro Val Gly Cys Thr Cys Val Leu
                 165                 170                 175 ccc cgt tca gtg tgaccgccga ggccgtgggg cccctagact ggacacgtgt         745
Pro Arg Ser Val
             180 gctccccaga gggcaccccc tatttatgtg tatttattgg tatttatatg cctcccccaa   805 cactacccct tgggtctggg cattcccgct gtctggagga cagccccca ctgttctcct    865 catctccagc ctcagtagtt gggggtagaa ggagctcagc acctcttcca gcccttaaag   925 ctgcagaaaa ggtgtcacac ggctgcctgt accttggctc cctgtcctgc tcccggcttc   985 ccttacccta tcactggcct caggcccccg caggctgcct cttcccaacc tccttggaag  1045 taccccctgtt tcttaaacaa ttatttaagt gtacgtgtat tattaaactg atgaacacat 1105 cc                                                                1107
```

<210> SEQ ID NO 23
<211> LENGTH: 197
<212> TYPE: PRT
<213> ORGANISM: Homo sapiens

<400> SEQUENCE: 23

```
Met Thr Leu Leu Pro Gly Leu Leu Phe Leu Thr Trp Leu His Thr Cys
        -15                 -10                  -5

Leu Ala His His Asp Pro Ser Leu Arg Gly His Pro His Ser His Gly
 -1  1               5                  10                  15

Thr Pro His Cys Tyr Ser Ala Glu Glu Leu Pro Leu Gly Gln Ala Pro
                 20                  25                  30

Pro His Leu Leu Ala Arg Gly Ala Lys Trp Gly Gln Ala Leu Pro Val
             35                  40                  45

Ala Leu Val Ser Ser Leu Glu Ala Ala Ser His Arg Gly Arg His Glu
         50                  55                  60

Arg Pro Ser Ala Thr Thr Gln Cys Pro Val Leu Arg Pro Glu Glu Val
     65                  70                  75

Leu Glu Ala Asp Thr His Gln Arg Ser Ile Ser Pro Trp Arg Tyr Arg
 80                  85                  90                  95

Val Asp Thr Asp Glu Asp Arg Tyr Pro Gln Lys Leu Ala Phe Ala Glu
```

```
                    100                 105                 110
Cys Leu Cys Arg Gly Cys Ile Asp Ala Arg Thr Gly Arg Glu Thr Ala
            115                 120                 125

Ala Leu Asn Ser Val Arg Leu Leu Gln Ser Leu Leu Val Leu Arg Arg
        130                 135                 140

Arg Pro Cys Ser Arg Asp Gly Ser Gly Leu Pro Thr Pro Gly Ala Phe
    145                 150                 155

Ala Phe His Thr Glu Phe Ile His Val Pro Val Gly Cys Thr Cys Val
160                 165                 170                 175

Leu Pro Arg Ser Val
            180

<210> SEQ ID NO 24
<211> LENGTH: 403
<212> TYPE: DNA
<213> ORGANISM: Homo sapiens
<220> FEATURE:
<221> NAME/KEY: misc_feature
<222> LOCATION: (390)..(390)
<223> OTHER INFORMATION: unknown amino

<400> SEQUENCE: 24
gagaaagagc ttcctgcaca aagtaagcca ccagcgcaac atgacagtga agaccctgca      60
tggcccagcc atggtcaagt acttgctgct gtcgatattg ggcttgcct ttctgagtga     120 ggcggcagct cggaaaatcc ccaaagtagg acatactttt ttccaaaagc ctgagagttg     180
cccgcctgtg ccaggaggta gtatgaagct tgacattggc atcatcaatg aaaaccagcg     240
cgtttccatg tcacgtaaca tcgagagccg ctccacctcc ccctggaatt acactgtcac     300
ttgggacccc aaccggtacc cctcgaagtt gtacaggccc aagtgtagga acttgggctg     360
tatcaatgct caaggaaagg aagacatctn catgaattcc gtc                       403

<210> SEQ ID NO 25
<211> LENGTH: 403
<212> TYPE: DNA
<213> ORGANISM: Homo sapiens
<220> FEATURE:
<221> NAME/KEY: misc_feature
<222> LOCATION: (390)..(390)
<223> OTHER INFORMATION: unknown amino
<220> FEATURE:
<221> NAME/KEY: CDS
<222> LOCATION: (71)..(403)
<223> OTHER INFORMATION:
<220> FEATURE:
<221> NAME/KEY: mat_peptide
<222> LOCATION: (131)..()
<223> OTHER INFORMATION:

<400> SEQUENCE: 25
gagaaagagc ttcctgcaca aagtaagcca ccagcgcaac atgacagtga agaccctgca      60
tggcccagcc atg gtc aag tac ttg ctg ctg tcg ata ttg ggc ttg gcc      109
            Met Val Lys Tyr Leu Leu Leu Ser Ile Leu Gly Leu Ala
                -20             -15                 -10 ttt ctg agt gag gcg gca gct cgg aaa atc ccc aaa gta gga cat act      157
Phe Leu Ser Glu Ala Ala Ala Arg Lys Ile Pro Lys Val Gly His Thr
        -5              -1  1               5 ttt ttc caa aag cct gag agt tgc ccg cct gtg cca gga ggt agt atg      205
Phe Phe Gln Lys Pro Glu Ser Cys Pro Pro Val Pro Gly Gly Ser Met
10                  15                  20                  25 aag ctt gac att ggc atc atc aat gaa aac cag cgc gtt tcc atg tca      253
Lys Leu Asp Ile Gly Ile Ile Asn Glu Asn Gln Arg Val Ser Met Ser
                30                  35                  40
```

```
cgt aac atc gag agc cgc tcc acc tcc ccc tgg aat tac act gtc act      301
Arg Asn Ile Glu Ser Arg Ser Thr Ser Pro Trp Asn Tyr Thr Val Thr
             45                  50                  55 tgg gac ccc aac cgg tac ccc tcg aag ttg tac agg ccc aag tgt agg      349
Trp Asp Pro Asn Arg Tyr Pro Ser Lys Leu Tyr Arg Pro Lys Cys Arg
             60                  65                  70 aac ttg ggc tgt atc aat gct caa gga aag gaa gac atc tnc atg aat      397
Asn Leu Gly Cys Ile Asn Ala Gln Gly Lys Glu Asp Ile Xaa Met Asn
 75                  80                  85 tcc gtc                                                              403
Ser Val
 90

<210> SEQ ID NO 26
<211> LENGTH: 111
<212> TYPE: PRT
<213> ORGANISM: Homo sapiens
<220> FEATURE:
<221> NAME/KEY: misc_feature
<222> LOCATION: (87)..(87)
<223> OTHER INFORMATION: The 'Xaa' at location 87 stands for Tyr, Cys,
      Ser, or Phe.
<220> FEATURE:
<221> NAME/KEY: misc_feature
<222> LOCATION: (390)..(390)
<223> OTHER INFORMATION: unknown amino

<400> SEQUENCE: 26

Met Val Lys Tyr Leu Leu Leu Ser Ile Leu Gly Leu Ala Phe Leu Ser
-20                 -15                 -10                  -5

Glu Ala Ala Ala Arg Lys Ile Pro Lys Val Gly His Thr Phe Phe Gln
             -1  1                   5                      10

Lys Pro Glu Ser Cys Pro Pro Val Pro Gly Gly Ser Met Lys Leu Asp
             15                  20                  25

Ile Gly Ile Ile Asn Glu Asn Gln Arg Val Ser Met Ser Arg Asn Ile
             30                  35                  40

Glu Ser Arg Ser Thr Ser Pro Trp Asn Tyr Thr Val Thr Trp Asp Pro
45                  50                  55                  60

Asn Arg Tyr Pro Ser Lys Leu Tyr Arg Pro Lys Cys Arg Asn Leu Gly
                 65                  70                  75

Cys Ile Asn Ala Gln Gly Lys Glu Asp Ile Xaa Met Asn Ser Val
             80                  85                  90

<210> SEQ ID NO 27
<211> LENGTH: 784
<212> TYPE: DNA
<213> ORGANISM: Homo sapiens
<220> FEATURE:
<221> NAME/KEY: CDS
<222> LOCATION: (3)..(281)
<223> OTHER INFORMATION:

<400> SEQUENCE: 27 tc gtg ccg tat ctt ttt aaa aaa att att ctt cac ttt ttt gcc tcc       47
   Val Pro Tyr Leu Phe Lys Lys Ile Ile Leu His Phe Phe Ala Ser
    1               5                  10                  15 tat tac ttg tta ggg aga ccc aat ggt agt ttt att cct tgg gga tac      95
Tyr Tyr Leu Leu Gly Arg Pro Asn Gly Ser Phe Ile Pro Trp Gly Tyr
             20                  25                  30 ata gta aat act tca tta aag tcg agt aca gaa ttt gat gaa aag tgt     143
Ile Val Asn Thr Ser Leu Lys Ser Ser Thr Glu Phe Asp Glu Lys Cys
             35                  40                  45 gga tgt gtg gga tgt act gcc gcc ttc aga agt cca cac act gcc tgg     191
```

```
Gly Cys Val Gly Cys Thr Ala Ala Phe Arg Ser Pro His Thr Ala Trp
        50                  55                  60 agg gag aga act gct gtt tat tca ctg att aag cat ttg ctg tgt acc         239
Arg Glu Arg Thr Ala Val Tyr Ser Leu Ile Lys His Leu Leu Cys Thr
 65                  70                  75 aac tac ttt tca tgt ctt atc tta att ctc ata aca gtc att                 281
Asn Tyr Phe Ser Cys Leu Ile Leu Ile Leu Ile Thr Val Ile
 80                  85                  90 tgatattta aaaaccccca gaaatctgag aaagagataa agtggtttgc tcaaggttat         341
agaacagact accatgtgtt gtatttcaga ttttaattca tgtttgtctg attttaagtt        401
ttgttcgctt gccagggtac cccacaaaaa tgccaggcag gcattttca tgatgcactt         461 gagatacctg aaatgacagg gtagcatcac acctgagagg ggtaaaggat gggaacctac        521
cttccatggc cgctgcttgg cagtctcttg ctgcatgcta gcagagccac tgtatatgtg       581
ccgaggctct gagaattaac tgcttaaaga actgccttct ggagggagaa gagcacaaga       641
tcacaattaa ccatatacac atcttactgt gcgaggtcat tgagcaatac aggagggatt      701
ttatacattt tagcaactat cttcaaaacc tgagctatag ttgtattctg ccccccttcct      761 ctgggcaaaa gtgtaaaagt ttg                                               784

<210> SEQ ID NO 28
<211> LENGTH: 93
<212> TYPE: PRT
<213> ORGANISM: Homo sapiens

<400> SEQUENCE: 28

Val Pro Tyr Leu Phe Lys Lys Ile Ile Leu His Phe Phe Ala Ser Tyr
 1               5                  10                  15

Tyr Leu Leu Gly Arg Pro Asn Gly Ser Phe Ile Pro Trp Gly Tyr Ile
             20                  25                  30

Val Asn Thr Ser Leu Lys Ser Ser Thr Glu Phe Asp Glu Lys Cys Gly
         35                  40                  45

Cys Val Gly Cys Thr Ala Ala Phe Arg Ser Pro His Thr Ala Trp Arg
     50                  55                  60

Glu Arg Thr Ala Val Tyr Ser Leu Ile Lys His Leu Leu Cys Thr Asn
 65                  70                  75                  80

Tyr Phe Ser Cys Leu Ile Leu Ile Leu Ile Thr Val Ile
                 85                  90

<210> SEQ ID NO 29
<211> LENGTH: 460
<212> TYPE: DNA
<213> ORGANISM: Homo sapiens
<220> FEATURE:
<221> NAME/KEY: CDS
<222> LOCATION: (1)..(189)
<223> OTHER INFORMATION:

<400> SEQUENCE: 29 gtg act gta ttg tgg gga cag gaa gca caa att ccc atg tgg atc act          48
Val Thr Val Leu Trp Gly Gln Glu Ala Gln Ile Pro Met Trp Ile Thr
 1               5                  10                  15 agg aga gat aat aag tgg ggt cat ttc acc cct tgg tcc cct gct tcc          96
Arg Arg Asp Asn Lys Trp Gly His Phe Thr Pro Trp Ser Pro Ala Ser
             20                  25                  30 aga ccc aaa gag gcc tac atg gca ttg tgc ttc ctt ctt agt tgt agg         144
Arg Pro Lys Glu Ala Tyr Met Ala Leu Cys Phe Leu Leu Ser Cys Arg
         35                  40                  45 agg tgt gag ata caa tca ttt gcc tct gac ttt gag ggt tgg tcc             189
Arg Cys Glu Ile Gln Ser Phe Ala Ser Asp Phe Glu Gly Trp Ser
```

```
Arg Cys Glu Ile Gln Ser Phe Ala Ser Asp Phe Glu Gly Trp Ser
     50                  55                  60 tagcatgccc ctgaccagta gccccttaaa tacttcattg atatggaagg tctctgaatc   249
ttcgtgggct taatctacca ctctctgaag ttcttatgtc tttcaaaggc ctctaaaatc   309
tctgccatgt cttgctcatc cagttgttag catgatgtca ttgatacagt ggactttgga   369
atctaagtgg ggagacactg gtaagtgacc aattacttca cctgtggtgt gcaagccaga   429
tcaggaagcc tctacctgca cgacaacaca t                                  460

<210> SEQ ID NO 30
<211> LENGTH: 63
<212> TYPE: PRT
<213> ORGANISM: Homo sapiens

<400> SEQUENCE: 30

Val Thr Val Leu Trp Gly Gln Glu Ala Gln Ile Pro Met Trp Ile Thr
1               5                   10                  15

Arg Arg Asp Asn Lys Trp Gly His Phe Thr Pro Trp Ser Pro Ala Ser
            20                  25                  30

Arg Pro Lys Glu Ala Tyr Met Ala Leu Cys Phe Leu Leu Ser Cys Arg
        35                  40                  45

Arg Cys Glu Ile Gln Ser Phe Ala Ser Asp Phe Glu Gly Trp Ser
    50                  55                  60

<210> SEQ ID NO 31
<211> LENGTH: 150
<212> TYPE: PRT
<213> ORGANISM: Rattus sp.

<400> SEQUENCE: 31

Met Cys Leu Met Leu Leu Leu Leu Asn Leu Glu Ala Thr Val Lys
1               5                   10                  15

Ala Ala Val Leu Ile Pro Gln Ser Ser Val Cys Pro Asn Ala Glu Ala
            20                  25                  30

Asn Asn Phe Leu Gln Asn Val Lys Val Asn Leu Lys Val Ile Asn Ser
        35                  40                  45

Leu Ser Ser Lys Ala Ser Ser Arg Arg Pro Ser Asp Tyr Leu Asn Arg
    50                  55                  60

Ser Thr Ser Pro Trp Thr Leu Ser Arg Asn Glu Asp Pro Asp Arg Tyr
65                  70                  75                  80

Pro Ser Val Ile Trp Glu Ala Gln Cys Arg His Gln Arg Cys Val Asn
                85                  90                  95

Ala Glu Gly Lys Leu Asp His His Met Asn Ser Val Leu Ile Gln Gln
            100                 105                 110

Glu Ile Leu Val Leu Lys Arg Glu Pro Glu Lys Cys Pro Phe Thr Phe
        115                 120                 125

Arg Val Glu Lys Met Leu Val Gly Val Gly Cys Thr Cys Val Ser Ser
    130                 135                 140

Ile Val Arg His Ala Ser
145                 150

<210> SEQ ID NO 32
<211> LENGTH: 147
<212> TYPE: PRT
<213> ORGANISM: Mus musculus

<400> SEQUENCE: 32

Met Leu Leu Leu Leu Leu Ser Leu Ala Ala Thr Val Lys Ala Ala Ala
```

-continued

```
                1               5                  10                 15
Ile Ile Pro Gln Ser Ser Ala Cys Pro Asn Thr Glu Ala Lys Asp Phe
                20                 25                 30

Leu Gln Asn Val Lys Val Asn Leu Lys Val Phe Asn Ser Leu Gly Ala
                35                 40                 45

Lys Val Ser Ser Arg Arg Pro Ser Asp Tyr Leu Asn Arg Ser Thr Ser
 50                 55                 60

Pro Trp Thr Leu His Arg Asn Glu Asp Pro Asp Arg Tyr Pro Ser Val
 65                 70                 75                 80

Ile Trp Glu Ala Gln Cys Arg His Gln Arg Cys Val Asn Ala Glu Gly
                85                 90                 95

Lys Leu Asp His His Met Asn Ser Val Leu Ile Gln Gln Glu Ile Leu
                100                105                110

Val Leu Lys Arg Glu Pro Glu Ser Cys Pro Phe Thr Phe Arg Val Glu
                115                120                125

Lys Met Leu Val Gly Val Gly Cys Thr Cys Val Ala Ser Ile Val Arg
                130                135                140

Gln Ala Ala
145

<210> SEQ ID NO 33
<211> LENGTH: 155
<212> TYPE: PRT
<213> ORGANISM: Homo sapiens

<400> SEQUENCE: 33

Met Thr Pro Gly Lys Thr Ser Leu Val Ser Leu Leu Leu Leu Leu Ser
 1               5                  10                 15

Leu Glu Ala Ile Val Lys Ala Gly Ile Thr Ile Pro Arg Asn Pro Gly
                20                 25                 30

Cys Pro Asn Ser Glu Asp Lys Asn Phe Pro Arg Thr Val Met Val Asn
                35                 40                 45

Leu Asn Ile His Asn Arg Asn Thr Asn Thr Pro Lys Arg Ser Ser
 50                 55                 60

Asp Tyr Tyr Asn Arg Ser Thr Ser Pro Trp Asn Leu His Arg Asn Glu
 65                 70                 75                 80

Asp Pro Glu Arg Tyr Pro Ser Val Ile Trp Glu Ala Lys Cys Arg His
                85                 90                 95

Leu Gly Cys Ile Asn Ala Asp Gly Asn Val Asp Tyr His Met Asn Ser
                100                105                110

Val Pro Ile Gln Gln Glu Ile Leu Val Leu Arg Arg Glu Pro Pro His
                115                120                125

Cys Pro Asn Ser Phe Arg Leu Glu Lys Ile Leu Val Ser Val Gly Cys
                130                135                140

Thr Cys Val Thr Pro Ile Val His His Val Ala
145                150                155

<210> SEQ ID NO 34
<211> LENGTH: 151
<212> TYPE: PRT
<213> ORGANISM: viral

<400> SEQUENCE: 34

Met Thr Phe Arg Lys Thr Ser Leu Val Leu Leu Leu Leu Leu Ser Ile
 1               5                  10                 15

Asp Cys Ile Val Lys Ser Glu Ile Thr Ser Ala Gln Thr Pro Arg Cys
                20                 25                 30
```

-continued

```
Leu Ala Ala Asn Asn Ser Phe Pro Arg Ser Val Met Val Thr Leu Ser
        35              40              45

Ile Arg Asn Trp Asn Thr Ser Ser Lys Arg Ala Ser Asp Tyr Tyr Asn
    50              55              60

Arg Ser Thr Ser Pro Trp Thr Leu His Arg Asn Glu Asp Gln Asp Arg
65              70              75                              80

Tyr Pro Ser Val Ile Trp Glu Ala Lys Cys Arg Tyr Leu Gly Cys Val
            85              90              95

Asn Ala Asp Gly Asn Val Asp Tyr His Met Asn Ser Val Pro Ile Gln
            100             105             110

Gln Glu Ile Leu Val Val Arg Lys Gly His Gln Pro Cys Pro Asn Ser
        115             120             125

Phe Arg Leu Glu Lys Met Leu Val Thr Val Gly Cys Thr Cys Val Thr
        130             135             140

Pro Ile Val His Asn Val Asp
145             150
```

NUCLEIC ACIDS ENCODING MURINE IL-174

The present application is a divisional of U.S. patent application Ser. No. 11/604,559; filed Nov. 27, 2006, now U.S. Pat. No. 7,625,720, which is a Continuation of commonly assigned, co-pending application Ser. No. 10/742,220; filed Dec. 19, 2003; which is a Divisional of Ser. No. 10/366,791; filed Feb. 14, 2003, now U.S. Pat. No. 7,005,501, which is a Divisional of Ser. No. 09/480,297; filed Jan. 10, 2000, now U.S. Pat. No. 6,562,578, which claims benefit of U.S. Provisional Patent Application No. 60/115,506; filed Jan. 11, 1999, each of which is incorporated herein by reference.

FIELD OF THE INVENTION

The present invention relates to compositions related to proteins which function in controlling physiology, development, and differentiation of mammalian cells, e.g., cells of a mammalian immune system. In particular, it provides nucleic acids, proteins, antibodies, and mimetics which regulate cellular physiology, development, differentiation, or function of various cell types, including hematopoietic cells.

BACKGROUND OF THE INVENTION

The immune system of vertebrates consists of a number of organs and several different cell types. Two major cell types include the myeloid and lymphoid lineages. Among the lymphoid cell lineage are B cells, which were originally characterized as differentiating in fetal liver or adult bone marrow, and T cells, which were originally characterized as differentiating in the thymus. See, e.g., Paul (ed. 1998) *Fundamental Immunology* (4th ed.) Raven Press, New York.

In many aspects of the development of an immune response or cellular differentiation, soluble proteins known as cytokines play a critical role in regulating cellular interactions. These cytokines apparently mediate cellular activities in many ways. They have been shown, in many cases, to modulate proliferation, growth, and differentiation of hematopoietic stem cells into the vast number of progenitors composing the lineages responsible for an immune response.

However, the cellular molecules which are expressed by different developmental stages of cells in these maturation pathways are still incompletely identified. Moreover, the roles and mechanisms of action of signaling molecules which induce, sustain, or modulate the various physiological, developmental, or proliferative states of these cells is poorly understood. Clearly, the immune system and its response to various stresses had relevance to medicine, e.g., infectious diseases, cancer related responses and treatment, allergic and transplantation rejection responses. See, e.g., Thorn, et al. *Harrison's Principles of Internal Medicine* McGraw/Hill, New York.

Medical science relies, in large degree, to appropriate recruitment or suppression of the immune system in effecting cures for insufficient or improper physiological responses to environmental factors. However, the lack of understanding of how the immune system is regulated or differentiates has blocked the ability to advantageously modulate the normal defensive mechanisms to biological challenges. Medical conditions characterized by abnormal or inappropriate regulation of the development or physiology of relevant cells thus remain unmanageable. The discovery and characterization of specific cytokines will contribute to the development of therapies for a broad range of degenerative or other conditions which affect the immune system, hematopoietic cells, as well as other cell types. The present invention provides solutions to some of these and many other problems.

SUMMARY OF THE INVENTION

The present invention is based, in part, upon the discovery of cDNA clones encoding various cytokine-like proteins which exhibit significant sequence similarity to the cytokine designated CTLA-8.

The invention embraces isolated genes encoding the proteins of the invention, variants of the encoded proteins, e.g., mutations (muteins) of the natural sequences, species and allelic variants, fusion proteins, chemical mimetics, antibodies, and other structural or functional analogs. Various uses of these different nucleic acid or protein compositions are also provided.

In certain nucleic acid embodiments, the invention provides an isolated or recombinant polynucleotide comprising sequence from: a) a mammalian IL-173, which: encodes at least 8 contiguous amino acids of SEQ ID NO: 6, 8, 10, or 12; encodes at least two distinct segments of at least 5 contiguous amino acids of SEQ ID NO: 6, 8, 10, or 12; or comprises one or more segments at least 21 contiguous nucleotides of SEQ ID NO: 5, 7, 9, or 11; b) a mammalian IL-174, which: encodes at least 8 contiguous amino acids of SEQ ID NO: 14, 16, or 18; encodes at least two distinct segments of at least 5 contiguous amino acids of SEQ ID NO: 14, 16, or 18; or comprises one or more segments at least 21 contiguous nucleotides of SEQ ID NO: 14, 16, or 18; c) a mammalian IL-176, which: encodes at least 8 contiguous amino acids of SEQ ID NO: 28; encodes at least two distinct segments of at least 5 contiguous amino acids of SEQ ID NO: 28; or comprises one or more segments at least 21 contiguous nucleotides of SEQ ID NO: 27; or d) a mammalian IL-177, which: encodes at least 8 contiguous amino acids of SEQ ID NO: 30; encodes at least two distinct segments of at least 5 contiguous amino acids of SEQ ID NO: 30; or comprises one or more segments at least 21 contiguous nucleotides of SEQ ID NO: 29. Other embodiments include such a polynucleotide in an expression vector, comprising sequence: a) (IL-173) which: encodes at least 12 contiguous amino acids of SEQ ID NO: 6, 8, 10, or 12; encodes at least two distinct segments of at least 7 and 10 contiguous amino acids of SEQ ID NO: 6, 8, 10, or 12; or comprises at least 27 contiguous nucleotides of SEQ ID NO: 5, 7, 9, 11; b) (IL-174) which: encodes at least 12 contiguous amino acids of SEQ ID NO: 14, 16, or 18; encodes at least two distinct segments of at least 7 and 10 contiguous amino acids of SEQ ID NO: 14, 16, or 18; or comprises at least 27 contiguous nucleotides of SEQ ID NO: 13, 15, or 17; c) (IL-176) which: encodes at least 12 contiguous amino acids of SEQ ID NO: 28; encodes at least two distinct segments of at least 7 and 10 contiguous amino acids of SEQ ID NO: 28; or comprises at least 27 contiguous nucleotides of SEQ ID NO: 27; or d) (IL-177) which: encodes at least 12 contiguous amino acids of SEQ ID NO: 30; encodes at least two distinct segments of at least 7 and 10 contiguous amino acids of SEQ ID NO: 30; or comprises at least 27 contiguous nucleotides of SEQ ID NO: 29. Certain embodiments will include those polynucleotides: a) (IL-173) which: encode at least 16 contiguous amino acid residues of SEQ ID NO: 6, 8, 10, or 12; encode at least two distinct segments of at least 10 and 13 contiguous amino acid residues of SEQ ID NO: 6, 8, 10, or 12; comprise at least 33 contiguous nucleotides of SEQ ID NO: 5, 7, 9, or 11; or comprise the entire mature coding portion of SEQ ID NO: 5, 7, 9, or 11; b) (IL-174) which: encode at least 16 contiguous amino acid residues of SEQ ID NO: 14, 16, or 18; encode at least two distinct segments of at least 10 and 13 contiguous amino acid residues of SEQ ID NO: 14, 16, or 18; comprise at least 33 contiguous nucleotides of SEQ ID NO: 13, 15, or 17; or comprise the entire mature coding portion of SEQ ID NO: 13, 15, or 17; c) (IL-176) which: encode at least 16 contiguous amino acids of SEQ ID NO: 28; encode at least two distinct segments of at least 10 and 14 contiguous amino acid residues of SEQ ID NO: 28; comprise at least 33 contiguous nucleotides of SEQ ID NO: 27; or comprise the entire mature coding portion of SEQ ID NO: 27; or d) (IL-177) which: encode at least 16 contiguous amino acids of SEQ ID NO: 30; encode at least two distinct segments of at least 10 and 14 contiguous amino acid residues of SEQ ID NO: 30; comprise at least 33 contiguous nucleotides of SEQ ID NO: 29; or comprise the entire mature coding portion of SEQ ID NO: 29.

Various methods are provided, e.g., making: a) a polypeptide comprising expressing the described expression vector, thereby producing the polypeptide; b) a duplex nucleic acid comprising contacting a described polynucleotide with a complementary nucleic acid, thereby resulting in production of the duplex nucleic acid; or c) a described polynucleotide comprising amplifying using a PCR method.

Alternatively, the invention provides an isolated or recombinant polynucleotide which hybridizes under stringent wash conditions of at least 55° C. and less than 400 mM salt to: a) the described (IL-173) polynucleotide which consists of the coding portion of SEQ ID NO: 5, 7, 9, or 11; b) the described (IL-174) polynucleotide which consists of the coding portion of SEQ ID NO: 13, 15, or 17; the described (IL-176) polynucleotide which consists of the coding portion of SEQ ID NO: 27; or d) the described (IL-177) polynucleotide which consists of the coding portion of SEQ ID NO: 29. Other embodiments include such described polynucleotide: a) wherein the wash conditions are at least 65° C. and less than 300 mM salt; or b) which comprises at least 50 contiguous nucleotides of the coding portion of: SEQ ID NO: 5, 7, 9, or 11 (IL-173); SEQ ID NO: 13, 15, or 17 (IL-174); SEQ ID NO: 27 (IL-176); or SEQ ID NO: 29 (IL-177).

Certain kits are provided, e.g., comprising a described polynucleotide, and: a) instructions for the use of the polynucleotide for detection; b) instructions for the disposal of the polynucleotide or other reagents of the kit; or c) both a and b.

Various cells are provided also, e.g., a cell containing the described expression vector, wherein the cell is: a prokaryotic cell; a eukaryotic cell; a bacterial cell; a yeast cell; an insect cell; a mammalian cell; a mouse cell; a primate cell; or a human cell.

Polypeptide embodiments include, e.g., an isolated or recombinant antigenic polypeptide: a) (IL-173) comprising at least: i) one segment of 8 identical contiguous amino acids from SEQ ID NO: 6, 8, 10, or 12; or ii) two distinct segments of at least 5 contiguous amino acids from SEQ ID NO: 6, 8, 10, or 12; b) (IL-174) comprising at least: i) one segment of 8 identical contiguous amino acids from SEQ ID NO: 14, 16, or 18; or ii) two distinct segments of at least 5 contiguous amino acids from SEQ ID NO: 14, 16, or 18; c) (IL-176) comprising at least: i) one segment of 8 identical contiguous amino acids from SEQ ID NO: 28; or ii) two distinct segments of at least 5 contiguous amino acids from SEQ ID NO: 28; or d) (IL-177) comprising at least: i) one segment of 8 identical contiguous amino acids from SEQ ID NO: 30; or ii) two distinct segments of at least 5 contiguous amino acids from SEQ ID NO: 30. Additional embodiments include such a described polypeptide, wherein: a) the segment of 8 identical contiguous amino acids is at least 14 contiguous amino acids; or b) one of the segments of at least 5 contiguous amino acids comprises at least 7 contiguous amino acids. Other embodiments include a described polypeptide, wherein: A) (IL-173) the polypeptide: a) comprises a mature sequence of SEQ ID NO: 6, 8, 10, or 12; b) binds with selectivity to a polyclonal antibody generated against an immunogen of a mature SEQ ID NO: 6, 8, 10, or 12; c) comprises a plurality of distinct polypeptide segments of 10 contiguous amino acids of SEQ ID NO: 6, 8, 10, or 12; d) is a natural allelic variant of SEQ ID NO: 6, 8, 10, or 12; e) has a length at least 30 amino acids; or f) exhibits at least two non-overlapping epitopes which are selective for the mature SEQ ID NO: 6, 8, 10, or 12; B) (IL-174) the polypeptide: a) comprises mature SEQ ID NO: 14, 16, or 18; b) binds with selectivity to a polyclonal antibody generated against an immunogen of mature SEQ ID NO: 14, 16, or 18; c) comprises a plurality of distinct polypeptide segments of 10 contiguous amino acids of SEQ ID NO: 14, 16, or 18; d) has a length at least 30 amino acids; or e) exhibits at least two non-overlapping epitopes which are selective for mature SEQ ID NO: 14, 16, or 18; C) (IL-176) the polypeptide: a) comprises SEQ ID NO: 28; b) binds with selectivity to a polyclonal antibody generated against an immunogen of SEQ ID NO: 28; c) comprises a plurality of distinct polypeptide segments of 10 contiguous amino acids of SEQ ID NO: 28; d) has a length at least 30 amino acids; or e) exhibits at least two non-overlapping epitopes which are selective for primate protein of SEQ ID NO: 28; or D) (IL-177) the polypeptide: a) comprises SEQ ID NO: 30; b) binds with selectivity to a polyclonal antibody generated against an immunogen of SEQ ID NO: 30; c) comprises a plurality of distinct polypeptide segments of 10 contiguous amino acids of SEQ ID NO: 30; d) has a length at least 30 amino acids; or e) exhibits at least two non-overlapping epitopes which are selective for primate protein of SEQ ID NO: 30. Various other embodiments include such a described polypeptide, which: a) is in a sterile composition; b) is not glycosylated; c) is denatured; d) is a synthetic polypeptide; e) is attached to a solid substrate; f) is a fusion protein with a detection or purification tag; g) is a 5-fold or less substitution from a natural sequence; or h) is a deletion or insertion variant from a natural sequence.

Methods of using described polypeptides are also provided, e.g.: a) to label the polypeptide, comprising labeling the polypeptide with a radioactive label; b) to separate the polypeptide from another polypeptide in a mixture, comprising running the mixture on a chromatography matrix, thereby separating the polypeptides; c) to identify a compound that binds selectively to the polypeptide, comprising incubating the compound with the polypeptide under appropriate conditions; thereby causing the compound to bind to the polypeptide; or d) to conjugate the polypeptide to a matrix, comprising derivatizing the polypeptide with a reactive reagent, and conjugating the polypeptide to the matrix.

Antibodies are also provided, including a binding compound comprising an antigen binding portion from an antibody which binds with selectivity to such a described polypeptide, wherein the polypeptide: a) (IL-173) comprises the mature polypeptide of SEQ ID NO: 6, 8, 10, or 12; b) (IL-174) comprises SEQ ID NO: 14, 16, or 18; c) (IL-176) comprises SEQ ID NO: 28; or d) (IL-177) comprises SEQ ID NO: 30. Certain embodiments embrace such a binding compound, wherein the antibody is a polyclonal antibody which is raised against the polypeptide of: a) (IL-173) SEQ ID NO: 6, 8, 10, or 12; b) (IL-174) SEQ ID NO: 14, 16, or 18; c) (IL-176) SEQ ID NO: 28; or d) (IL-177) SEQ ID NO: 30. Other embodiments include such a described binding compound, wherein the: a) antibody: i) is immunoselected; ii) binds to a denatured protein; or iii) exhibits a Kd to the polypeptide of at least 30 mM; or b) the binding compound: i) is attached to a solid substrate, including a bead or plastic membrane; ii) is in a sterile composition; or iii) is detectably labeled, including a radioactive or fluorescent label.

Methods are provided, e.g., producing an antigen:antibody complex, comprising contacting a polypeptide comprising sequence from SEQ ID NO: 6, 8, 10, 12, 14, 16, 18, 28, or 30 with a described binding compound under conditions which allow the complex to form. Preferably, the binding compound is an antibody, and the polypeptide is in a biological sample.

Kits are provided, e.g., comprising a described binding compound and: a) a polypeptide of SEQ ID NO: 6, 8, 10, 12, 14, 16, 18, 28, or 30; b) instructions for the use of the binding compound for detection; or c) instructions for the disposal of the binding compound or other reagents of the kit.

And a method is provided of evaluating the selectivity of binding of an antibody to a protein of SEQ ID NO: 6, 8, 10, 12, 14, 16, 18, 28, or 30, comprising contacting a described antibody to the protein and to another cytokine; and comparing binding of the antibody to the protein and the cytokine.

DETAILED DESCRIPTION OF THE PREFERRED EMBODIMENTS

Outline
I. General
II. Nucleic Acids
   A. natural isolates; methods
   B. synthetic genes
   C. methods to isolate
III. Purified CTLA-8 homolog proteins
   A. physical properties
   B. biological properties
IV. Making CTLA-8 homolog proteins; Mimetics
   A. recombinant methods
   B. synthetic methods
   C. natural purification
V. Physical Variants
   A. sequence variants, fragments
   B. post-translational variants
      1. glycosylation
      2. others
VI. Functional Variants
   A. analogs; fragments
      1. agonists
      2. antagonists
   B. mimetics
      1. protein
      2. chemicals
   C. species variants
VII. Antibodies
   A. polyclonal
   B. monoclonal
   C. fragments, binding compositions
VIII. Uses
   A. diagnostic
   B. therapeutic
IX. Kits
   A. nucleic acid reagents
   B. protein reagents
   C. antibody reagents I. General The present invention provides DNA sequence encoding various mammalian proteins which exhibit structural features characteristic of cytokines, particularly related to the cytokine designated CTLA-8 (also referred to as IL-17). Rat, mouse, human forms and a viral homolog of the CTLA-8 have been described and their sequences available from GenBank. See Rouvier, et al. (1993) *J. Immunol.* 150:5445-5456; Yao, et al. (1995) *Immunity* 3:811-821; Yao, et al. (1995) *J. Immunol.* 155:5483-5486; and Kennedy, et al. (1996) *J. Interferon and Cytokine Res.* 16:611-617. The CTLA-8 has activities implicated in arthritis, kidney graft rejection, tumorigenicity, virus-host interactions, and innate immunity; and appears to exhibit certain regulatory functions similar to IL-6. See PubMed (search for IL-17); Chabaud, et al. (1998) *J. Immunol.* 63:139-148; Amin, et al. (1998) *Curr. Opin. Rheumatol.* 10:263-268; Van Kooten, et al. (1998) *J. Am. Soc. Nephrol.* 9:1526-1534; Fossiez, et al. (1998) *Int. Rev. Immunol.* 16:541-551; Knappe, et al. (1998) *J. Virol.* 72:5797-5801; Seow (1998) *Vet. Immuno. Immunopathol.* 63:139-48; and Teunissen, et al. (1998) *J. Invest. Dermatol.* 111:645-649. A report on the signaling through the NFκB transcription factor implicates a signal pathway which is used in innate immunity. Shalom-Barak, et al. (1998) *J. Biol. Chem.* 273:27467-27473.

The newly presented cDNA sequences exhibit various features which are characteristic of mRNAs encoding cytokines, growth factors, and oncogenes. Because the IL-17 is the first member of this newly recognized family of cytokines related to TGF-β, Applicants have designated the family IL-170, with the new members IL-172, IL-173, IL-174, IL-176, IL-177; and IL-171 and IL-175. The fold for this family is predicted to be that of the TGF-β family of cytokines. The TGF-β family of cytokines, and the IL-170 family share the common feature of a cystine knot motif, characterized by a particular spacing of cysteine residues. See, e.g., Sun and Davies (1995) *Ann. Rev. Biophys. Biomolec. Struct.* 24:269-291; McDonald, et al. (1993) *Cell* 73:421-424; and Isaacs (1995) *Curr. Op. Struct. Biol.* 5:391-395. In particular, the structures suggest a number of conserved cysteines, which correspond to, and are numbered, in human IL-172 (SEQ ID NO: 2), cysteines at 101, 103, 143, 156, and 158. The first cysteine corresponds to the position in Table 7 of human IL-172 (SEQ ID NO: 2) val19. The fourth cysteine corresponds to that at mouse IL-172 (SEQ ID NO: 4) cys141; at human IL-173 (SEQ ID NO: 6) cys119; at mouse IL-174 (SEQ ID NO: 16) cys104; and at human IL-171 (SEQ ID NO: 21) cys50. The disulfide linkages should be cysteines 2 with 5; and 3 with 6; and 1 with 4. Functional significance of the fold similarity suggests formation of dimers for the IL-170 family. As a consequence, IL-170 dimers would bring together two cell surface receptors, through which signal transduction will occur.

These new proteins are designated CTLA-8 related, or generally IL-170, proteins. The natural proteins should be capable of mediating various physiological responses which would lead to biological or physiological responses in target cells, e.g., those responses characteristic of cytokine signaling. Initial studies had localized the message encoding this protein to various cell lines of hematopoietic cells. Genes encoding the original CTLA-8 (IL-17) antigen have been mapped to mouse chromosome 1A and human chromosome 2q31. Murine CTLA-8 was originally cloned by Rouvier, et al. (1993) *J. Immunol.* 150:5445-5456. The human IL-173 has been mapped to chromosome 13q11. Similar sequences for proteins in other mammalian species should also be available.

Purified CTLA-8, when cultured with synoviocytes, is able to induce the secretion of IL-6 from these cells. This induction is reversed upon the addition of a neutralizing antibody raised against human CTLA-8. Endothelial, epithelial, fibroblast and carcinoma cells also exhibit responses to treatment with CTLA-8. This data suggests that CTLA-8 may be implicated in inflammatory fibrosis, e.g., psoriasis, scleropdermia, lung fibrosis, or cirrhosis. CTLA-8 may also cause proliferation of carcinomas or other cancer cells inasmuch as IL-6 often acts as a growth factor for such cells. As such, the newly discovered other related family members are likely to have similar or related biological activities.

The descriptions below are directed, for exemplary purposes, to a murine or human IL-170 proteins, but are likewise applicable to related embodiments from other species.

II. Nucleic Acids

Tables 1-6 disclose the nucleotide and amino acid sequences of various new IL-170 family member sequences. The described nucleotide sequences and the related reagents are useful in constructing DNA clones useful for extending the clones in both directions for full length or flanking sequence determination, expressing IL-170 polypeptides, or, e.g., isolating a homologous gene from another natural source. Typically, the sequences will be useful in isolating other genes, e.g., allelic variants, from mouse, and similar procedures will be applied to isolate genes from other species, e.g., warm blooded animals, such as birds and mammals. Cross hybridization will allow isolation of genes from other species. A number of different approaches should be available to successfully isolate a suitable nucleic acid clone from other sources.

TABLE 1

```
Nucleotide sequence encoding a primate, e.g., human,
IL-172 polypeptide and predicted amino acid sequence. Also can use
complementary nucleic acid sequences for many purposes. Predicted
signal cleavage site indicated, but may be a few residues on either
side; putative glycosylation site at residues 55-57. SEQ ID NO: 1
and 2.
ATG GAC TGG CCT CAC AAC CTG CTG TTT CTT CTT ACC ATT TCC ATC TTC
48
Met Asp Trp Pro His Asn Leu Leu Phe Leu Leu Thr Ile Ser Ile Phe
-20              -15               -10                    -5

CTG GGG CTG GGC CAG CCC AGG AGC CCC AAA AGC AAG AGG AAG GGG CAA
96
Leu Gly Leu Gly Gln Pro Arg Ser Pro Lys Ser Lys Arg Lys Gly Gln
                  1             5                 10

GGG CGG CCT GGG CCC CTG GTC CCT GGC CCT CAC CAG GTG CCA CTG GAC
144
Gly Arg Pro Gly Pro Leu Val Pro Gly Pro His Gln Val Pro Leu Asp
             15                20                  25

CTG GTG TCA CGG ATG AAA CCG TAT GCC CGC ATG GAG GAG TAT GAG AGG
192
Leu Val Ser Arg Met Lys Pro Tyr Ala Alg Met Glu Glu Tyr Glu Arg
         30                  35                  40

AAC ATC GAG GAG ATG GTG GCC CAG CTG AGG AAC AGC TCA GAG CTG GCC
240
Asn Ile Glu Glu Met Val Ala Gln Leu Arg Asn Ser Ser Glu Leu Ala
 45                 50                  55                    60

CAG AGA AAG TGT GAG GTC AAC TTG CAG CTG TGG ATG TCC AAC AAG AGG
288
Gln Arg Lys Cys Glu Val Asn Leu Gln Leu Trp Met Ser Asn Lys Arg
             65                  70                     75

AGC CTG TCT CCC TGG GGC TAC AGC ATC AAC CAC GAC CCC AGC CGT ATC
336
Ser Leu Ser Pro Trp Gly Tyr Ser Ile Asn His Asp Pro Ser Arg Ile
             80                  85                  90

CCC GTG GAC CTG CCG GAG GCA CGG TGC CTG TGT CTG GGC TGT GTG AAC
384
Pro Val Asp Leu Pro Glu Ala Arg Cys Leu Cys Leu Gly Cys Val Asn
             95                 100                 105

CCC TTC ACC ATG CAG GAG GAC CGC AGC ATG GTG AGC GTG CCG GTG TTC
432
Pro Phe Thr Met Gln Glu Asp Arg Ser Met Val Ser Val Pro Val Phe
         110                 115                 120

AGC CAG GTT CCT GTG CGC CGC CGC CTC TGC CCG CCA CCG CCC CGC ACA
480
Ser Gln Val Pro Val Arg Arg Arg Leu Cys Pro Pro Pro Arg Thr
125                 130                 135                 140

GGG CCT TGC CGC CAG CGC GCA GTC ATG GAG ACC ATC GCT GTG GGC TGC
528
Gly Pro Cys Arg Gln Arg Ala Val Met Glu Thr Ile Ala Val Gly Cys
                 145                 150                 155

ACC TGC ATC TTC TGA
543
Thr Cys Ile Phe
             160
```

TABLE 1-continued

MDWPHNLLFLLTISIFLGLG QPRSPKSKRKGQGRPGPLVPGPHQVPLDLVSRNKPYARMEEYERNI

EEMVAQLRNSSELAQRKCEVNLQLWMSNKRSLSPWGYSINHDPSRIPVDLPEARCLCLGCVNPFTMQ

EDRSMVSVPVFSQVPVRRRLCPPPPRTGPCRQRAVMETIAVGCTCIF

Particularly interesting segments include, e.g., those which
begin or end with gln1; val19; pro20; pro22; lys34; pro35; leu78;
ser79; glu98; ala99; phe110; thr111; cys143; or arg144.

Nucleotide sequence encoding a rodent, e.g., mouse, IL-172
polypeptide and predicted among acid sequence. Also can use
complementary nucleic acid sequences for many purposes. Predicted
signal cleavage site indicated, but may be a few residues on either
side; putative glycosylation site at residues 53-55. SEQ ID NO: 3
and 4.

```
ATG GAC TGG CCG CAC AGC CTG CTC TTC CTC CTG GCC ATC TCC ATC TTC
48
Met Asp Trp Pro His Ser Leu Leu Phe Leu Leu Ala Ile Ser Ile Phe
-22     -20             -15                 -10

CTG GCG CCA AGC CAC CCC CGG AAC ACC AAA GGC AAA AGA AAA GGG CAA
96
Leu Ala Pro Ser His Pro Arg Asn Thr Lys Gly Lys Arg Lys Gly Gln
        -5                  1           5                   10

GGG AGG CCC AGT CCC TTG GCC CCT GGG CCT CAT CAG GTG CCG CTG GAC
144
Gly Arg Pro Ser Pro Leu Ala Pro Gly Pro His Gln Val Pro Leu Asp
                15                  20                  25

CTG GTG TCT CGA GTA AAG CCC TAC GCT CGA ATG GAA GAG TAT GAG CGG
192
Leu Val Ser Arg Val Lys Pro Tyr Ala Arg Met Glu Glu Tyr Glu Arg
                30                  35                  40

AAC CTT GGG GAG ATG GTG GCC CAG CTG AGG AAC AGC TCC GAG CCA GCC
240
Asn Leu Gly Glu Met Val Ala Gln Leu Arg Asn Ser Ser Glu Pro Ala
            45                  50                  55

AAG AAG AAA TGT GAA GTC AAT CTA CAG CTG TGG TTG TCC AAC AAG AGG
288
Lys Lys Lys Cys Glu Val Asn Leu Gln Leu Trp Leu Ser Asn Lys Arg
        60                  65                  70

AGC CTG TCC CCA TGG GGC TAC AGC ATC AAC CAC GAC CCC AGC CGC ATC
336
Ser Leu Ser Pro Trp Gly Tyr Ser Ile Asn His Asp Pro Ser Arg Ile
75                  80                  85                  90

CCT GCG GAC TTG CCC GAG GCG CGG TGC CTA TGT TTG GGT TGC GTG AAT
384
Pro Ala Asp Leu Pro Glu Ala Arg Cys Leu Cys Leu Gly Cys Val Asn
                95                  100                 105

CCC TTC ACC ATG CAG GAG GAC CGT AGC ATG GTG AGC GTG CCA GTG TTC
432
Pro Phe Thr Met Gln Glu Asp Arg Ser Met Val Ser Val Pro Val Phe
            110                 115                 120

AGC CAG GTG CCG GTG CGC CGC CGC CTC TGT CCT CAA CCT CCT CGC CCT
480
Ser Gln Val Pro Val Arg Arg Arg Leu Cys Pro Gln Pro Pro Arg Pro
        125                 130                 135

GGG CCC TGC CGC CAG CGT GTC GTC ATG GAG ACC ATC GCT GTG GGT TGC
528
Gly Pro Cys Arg Gln Arg Val Val Met Glu Thr Ile Ala Val Giy Cys
    140                 145                 150

ACC TGC ATC TTC TGA
543
Thr Cys Ile Phe
155
```

TABLE 1-continued

MDWPHSLLFLLAISIFLAPSHP RNTKGKRKGQGRPSPLAPGPHQVPLDLVSRVKPYARMEEYERNL

GEMVAQLRNSSEPAKKKCEVNLQLWLSNKRSLSPWGYSINHDPSRIPADLPEARCLCLGCVNPFTMQ

EDRSMVSVPVFSQVPVRRRLCPQPPRPGPCRQRVVMETIAVGCTCIF

Particularly interesting segments include, e.g., those which begin or end with arg1; ala17; pro18; pro20; his21; lys32; pro33; leu76; ser77; glu96; ala97; phe108; thr109; cys141; or arg142.

TABLE 2

Nucleotide sequence encoding a primate, e.g., human, IL-173 polypeptide and predicted amino acid sequence. Also can use complementary nucleic acid sequences for many purposes. SEQ ID NO: 5 and 6.

```
TGC GCG GAC CGG CCG GAG GAG CTA CTG GAG CAG CTG TAC GGG CGC CTG
                                                                48
Cys Ala Asp Arg Pro Glu Glu Leu Leu Glu Gln Leu Tyr Gly Arg Leu
  1               5                  10                  15

GCG GCC GGC GTG CTC AGT GCC TTC CAC CAC ACG CTG CAG CTG GGG CCG
                                                                96
Ala Ala Gly Val Leu Ser Ala Phe His His Thr Leu Gln Leu Gly Pro
              20                  25                  30

CGT GAG CAG GCG CGC AAC GCG AGC TGC CCG GCA GGG GGC AGG CCC GCC
                                                                144
Arg Glu Gln Ala Arg Asn Ala Ser Cys Pro Ala Gly Gly Arg Pro Ala
          35                  40                  45

GAC CGC CGC TTC CGG ACG CCC ACC AAC CTG CGC AGC GTG TCG CCC TGG
                                                                192
Asp Arg Arg Phe Arg Thr Pro Thr Asn Leu Arg Ser Val Ser Pro Trp
      50                  55                  60

GCC TAC AGA ATC TCC TAC GAC CCG GCG AGG TAC CCC AGG TAC CTG CCT
                                                                240
Ala Tyr Arg Ile Ser Tyr Asp Pro Ala Arg Tyr Pro Arg Tyr Leu Pro
  65                  70                  75                  80

GAA GCC TAC TGC CTG TGC CGG GGC TGC CTG ACC GGG CTG TTC GGC GAG
                                                                288
Glu Ala Tyr Cys Leu Cys Arg Gly Cys Leu Thr Gly Leu Phe Gly Glu
              85                  90                  95

GAG GAC GTG CGC TTC CGC AGC GCC CCT GTC TAC ATG CCC ACC GTC GTC
                                                                336
Glu Asp Val Arg Phe Arg Ser Ala Pro Val Tyr Met Pro Thr Val Val
          100                 105                 110

CTG CGC CGC ACC CCC GCC TGC GCC GGC GGC CGT TCC GTC TAC ACC GAG
                                                                384
Leu Arg Arg Thr Pro Ala Cys Ala Gly Gly Arg Ser Val Tyr Thr Glu
      115                 120                 125

GCC TAC GTC ACC ATC CCC GTG GGC TGC ACC TGC GTC CCC GAG CCG GAG
                                                                432
Ala Tyr Val Thr Ile Pro Val Gly Cys Thr Cys Val Pro Glu Pro Glu
  130                 135                 140

AAG GAC GCA GAC AGC ATC AAC T
                              454
Lys Asp Ala Asp Ser Ile Asn
145                 150
```

CADRPEELLEQLYGRLAAGVLSAFHHTLQLGPREQARNASCPAGGRPADRRFRTPTNLRSVSPWAYR

ISYDPARYPRYLPEAYCLCRGCLTGLFGEEDVRFRSAPVYMPTVVLRRTPACAGGRSVYTEAYVTIP

VGCTCVPEPEKDADSIN

TABLE 2-continued

Supplementary nucleotide sequence encoding a primate, e.g., human, IL-173 polypeptide and predicted among acid sequence. Also can use complementary nucleic acid sequences for many purposes. SEQ ID NO: 7 and 8.

```
gcccgggcag gtggcgacct cgctcagtcg gcttctcggt ccaagtcccc gggtctgg      58 atg ctg gta gcc ggc ttc ctg ctg gcg ctg ccg ccg agc tgg gcc gcg     106
Met Leu Val Ala Gly Phe Leu Leu Ala Leu Pro Pro Ser Trp Ala Ala
    -15              -10                  -5 ggc gcc ccg agg gcg ggc agg cgc ccc gcg cgg ccg cgg ggc tgc gcg     154
Gly Ala Pro Arg Ala Gly Arg Arg Pro Ala Arg Pro Arg Gly Cys Ala
 -1   1              5                  10                  15 gac cgg ccg gag gag cta ctg gag cag ctg tac ggg cgc ctg gcg gcc     202
Asp Arg Pro Glu Glu Leu Leu Glu Gln Leu Tyr Gly Arg Leu Ala Ala
                 20                  25                  30 ggc gtg ctc agt gcc ttc cac cac acg ctg cag ctg ggg ccg cgt gag     250
Gly Val Leu Ser Ala Phe His His Thr Leu Gln Leu Gly Pro Alg Glu
             35                  40                  45 cag gcg cgc aac gcg agc tgc ccg gca ggg ggc agg ccc gcc gac cgc     298
Gln Ala Arg Asn Ala Ser Cys Pro Ala Gly Gly Arg Pro Ala Asp Arg
         50                  55                  60 cgc ttc cgg ccg ccc acc aac ctg cgc agc gtg tcg ccc tgg gcc tac     346
Arg Phe Arg Pro Pro Thr Asn Leu Arg Ser Val Ser Pro Trp Ala Tyr
     65                  70                  75 aga atc tcc tac gac ccg gcg agg tac ccc agg tac ctg cct gaa gcc     394
Arg Ile Ser Tyr Asp Pro Ala Arg Tyr Pro Arg Tyr Leu Pro Glu Ala
 80                  85                  90                  95 tac tgc ctg tgc cgg ggc tgc ctg acc ggg ctg ttc ggc gag gag gac     442
Tyr Cys Leu Cys Arg Gly Cys Leu Thr Gly Leu Phe Gly Glu Glu Asp
                    100                 105                 110 gtg cgc ttc cgc agc gcc cct gtc tac atg ccc acc gtc gtc ctg cgc     490
Val Arg Phe Arg Ser Ala Pro Val Tyr Met Pro Thr Val Val Leu Arg
                115                 120                 125 cgc acc ccc gcc tgc gcc ggc ggc cgt tcc gtc tac acc gag gcc tac     538
Arg Thr Pro Ala Cys Ala Gly Gly Arg Ser Val Tyr Thr Glu Ala Tyr
            130                 135                 140 gtc acc atc ccc gtg ggc tgc acc tgc gtc ccc gag ccg gag aag gac     586
Val Thr Ile Pro Val Gly Cys Thr Cys Val Pro Glu Pro Glu Lys Asp
145                 150                 155 gca gac agc atc aac tcc agc atc gac aaa cag ggc gcc aag ctc ctg     634
Ala Asp Ser Ile Asn Ser Ser Ile Asp Lys Gln Gly Ala Lys Leu Leu
160                 165                 170                 175 ctg ggc ccc aac gac gcg ccc gct ggc ccc tgaggccggt cctgccccgg       684
Leu Gly Pro Asn Asp Ala Pro Ala Gly Pro
                180                 185 gaggtctccc cggccgcat cccgaggcgc caagctgga gccgctgga gggctcggtc      744 ggcgacctct gaagagagtg caccgagcaa accaagtgcc ggagcaccag cgccgccttt    804
ccatggagac tcgtaagcag cttcatctga cacgggcatc cctggcttgc ttttagctac    864
aagcaagcag cgtggctgga agctgatggg aaacgacccg gcacgggcat cctgtgtgcg    924
gcccgcatgg agggtttgga aaagttcacg gaggctccct gaggagcctc tcagatcggc    984
tgctgcgggt gcaggcgtg actcaccgct gggtgcttgc caaagagata gggacgcata    1044
tgctttttaa agcaatctaa aaataataat aagtatagcg actatatacc tacttttaaa   1104
atcaactgtt ttgaatagag gcagagctat tttatattat caaatgagag ctactctgtt   1164
acatttctta acatataaac atcgttttt acttcttctg gtagaatttt ttaaagcata   1224
```

TABLE 2-continued

```
attggaatcc ttggataaat tttgtagctg gtacactctg gcctgggtct ctgaattcag   1284
cctgtcaccg atggctgact gatgaaatgg acacgtctca tctgacccac tcttccttcc   1344
actgaaggtc ttcacgggcc tccaggcctc gtgccgaatt c                       1385
```

MLVAGFLLALPPSWAAGAPRAGRRPARPRGCADRPEELLEQLYGRLAAGVLSAFHHTLQLGPREQAR

NASCPAGGRPADRRFRPPTNLRSVSPWAYRISYDPARYPRYLPEAYCLCRGCLTGLFGEEDVRFRSA

PVYMPTVVLRRTPACAGGRSVYTEAYVTIPVGCTCVPEPEKDADSINSSIDKQGAKLLLGPNDAPAG

P

Important predicted motifs include, e.g., cAMP PK at 50-53, 66-69, 72-75, and 113-116; Ca Phos at 82-84 and 166-168; myristoly sites at 57-61 and 164-166; phosphorylation sites at 50, 53, 72, 75, 80, 82, 113, and 116.

Nucleotide sequence encoding a rodent, e.g., rat, IL-173 polypeptide and predicted amino acid sequence. Also can use complementary nucleic acid sequences for many purposes. SEQ ID NO: 9 and 10.

```
TTT CCG AGA TAC CTG CCC GAA GCC TAC TGC CTG TGC CGA GGC TGT CTG     48
Phe Pro Arg Tyr Leu Pro Glu Ala Tyr Cys Leu Cys Arg Gly Cys Leu
 1               5                  10                  15

ACC GGG CTC TAC GGT GAG GAG GAC TTC CGC TTT CGC AGC GCA CCC GTC     96
Thr Gly Leu Tyr Gly Glu Glu Asp Phe Arg Phe Arg Ser Ala Pro Val
             20                  25                  30

TTC TCT CCG GCG GTG GTG CTG CGG CGC ACG GCG GCC T                  133
Phe Ser Pro Ala Val Val Leu Arg Arg Thr Ala Ala
         35                  40
```

FPRYLPEAYCLCRGCLTGLYGEEDFRFRSAPVFSPAVVLRRTAA

Supplementary nucleotide sequence encoding a rodent, e.g., mouse, IL-173 polypeptide and predicted amino acid sequence. Also can use complementary nucleic acid sequences for many purposes. SEQ ID NO: 11 and 12.

```
atg ttg ggg aca ctg gtc tgg atg ctc ctc gtc ggc ttc ctg ctg gca     48
Met Leu Gly Thr Leu Val Trp Met Leu Leu Val Gly Phe Leu Leu Ala
            -20                 -15                 -10 ctg gcg ccg ggc cgc gcg gcg ggc gcg ctg agg acc ggg agg cgc ccg     96
Leu Ala Pro Gly Arg Ala Ala Gly Ala Leu Arg Thr Gly Arg Arg Pro
            -5              -1   1               5 gcg cgg ccg cgg gac tgc gcg gac cgg cca gag gag ctc ctg gag cag    144
Ala Arg Pro Arg Asp Cys Ala Asp Arg Pro Glu Glu Leu Leu Glu Gln
        10                  15                  20 ctg tac ggg cgg ctg gcg gcc ggc gtg ctc agc gcc ttc cac cac acg    192
Leu Tyr Gly Arg Leu Ala Ala Gly Val Leu Ser Ala Phe His His Thr
    25                  30                  35                  40 ctg cag ctc ggg ccg cgc gag cag gcg cgc aat gcc agc tgc ccg gcc    240
Leu Gln Leu Gly Pro Arg Glu Gln Ala Arg Asn Ala Ser Cys Pro Ala
                45                  50                  55 ggg ggc agg gcc gcc gac cgc cgc ttc cgg cca ccc acc aac ctg cgc    288
Gly Gly Arg Ala Ala Asp Arg Arg Phe Arg Pro Pro Thr Asn Leu Arg
            60                  65                  70 agc gtg tcg ccc tgg gcg tac agg att tcc tac gac cct gct cgc ttt    336
Ser Val Ser Pro Trp Ala Tyr Arg Ile Ser Tyr Asp Pro Ala Arg Phe
        75                  80                  85 ccg agg tac ctg ccc gaa gcc tac tgc ctg tgc cga ggc tgc ctg acc    384
Pro Arg Tyr Leu Pro Glu Ala Tyr Cys Leu Cys Arg Gly Cys Leu Thr
    90                  95                  100 ggg ctc tac ggg gag gag gac ttc cgc ttt cgc agc aca ccc gtc ttc    432
Gly Leu Tyr Gly Glu Glu Asp Phe Arg Phe Arg Ser Thr Pro Val Phe
105                 110                 115                 120 tct cca gcc gtg gtg ctg cgg cgc aca gcg gcc tgc gcg ggc ggc cgc    480
Ser Pro Ala Val Val Leu Arg Arg Thr Ala Ala Cys Ala Gly Gly Arg
            125                 130                 135
```

TABLE 2-continued

```
tct gtg tac gcc gaa cac tac atc acc atc ccg gtg ggc tgc acc tgc    528
Ser Val Tyr Ala Glu His Tyr Ile Thr Ile Pro Val Gly Cys Thr Cys
            140                 145                 150 gtg ccc gag ccg gac aag tcc gcg gac agt gcg aac tcc agc atg gac    576
Val Pro Glu Pro Asp Lys Ser Ala Asp Ser Ala Asn Ser Ser Met Asp
            155                 160                 165 aag ctg ctg ctg ggg ccc gcc gac agg cct gcg ggg cgc tgatgccggg    625
Lys Leu Leu Leu Gly Pro Ala Asp Arg Pro Ala Gly Arg
            170                 175                 180 gactgcccgc catggcccag cttcctgcat gcatcaggtc ccctggccct gacaaaaccc   685 acccccatgat ccctggccgc tgcctaattt ttccaaaagg acagctacat aagctttaaa    745
tatatttttc aaagtagaca ctacatatct acaactattt tgaatagtgg cagaaactat    805
tttcatatta gtaatttaga gcaagcatgt tgtttttaaa cttctttgat atacaagcac    865
atcacacaca tcccgttttc ctctagtagg attcttgagt gcataattgt agtgctcaga    925
tgaacttcct tctgctgcac tgtgcccgt ccctgagtct ctcctgtggc ccaagcttac    985
taaggtgata atgagtgctc cggatctggg cacctaaggt ctccaggtcc ctggagaggg    1045
agggatgtgg gggggctagg aaccaagcgc cctttgttc tttagcttat ggatggtctt    1105
aactttataa agattaaagt ttttggtgtt attctttc    1143
```

MLGTLVWMLLVGFLLALAPGRAAGALRTGRRPARPRDCADRPEELLEQLYGRLAAG

VLSAFHHTLQLGPREQARNASCPAGGRAADRRFRPPTNLRSVSPWAYRISYDPARF

PRYLPEAYCLCRGCLTGLYGEEDFRFRSTPVFSPAVVLRRTAACAGGRSVYAEHYI

TIPVGCTCVPEPDKSADSANSSMDKLLLGPADRPAGR

Important predicted motifs include, e.g., cAMP PK sites at 50-53, 66-69, 72-75, and 113-116; Ca phosphorylation sites at 82-84, 159-161, and 166-168; myristoly sites at 57-61 and 101-105; N-glycosyl sites at 51-53 and 164-166; phosphorylation sites at 50, 53, 72, 75, 80, 82, 113, and 116; and PKC phosphorylation sites at 4-6

TABLE 3

Nucleotide sequence encoding a primate, e.g., human, IL-174 polypeptide and predicted amino acid sequence. Also can use complementary nucleic acid sequences for many purposes. SEQ ID NO: 13 and 14.

```
tgagtgtgca gtgccagc atg tac cag gtg gtt gca ttc ttg gca atg gtc    51
                    Met Tyr Gln Val Val Ala Phe Leu Ala Met Val
                        -15                 -10 atg gga acc cac acc tac agc cac tgg ccc agc tgc tgc ccc agc aaa    99
Met Gly Thr His Thr Tyr Ser His Trp Pro Ser Cys Cys Pro Ser Lys
 -5              -1  1                   5                  10 ggg cag gac acc tct gag gag ctg ctg agg tgg agc act gtg cct gtg    147
Gly Gln Asp Thr Ser Glu Glu Leu Leu Arg Trp Ser Thr Val Pro Val
            15                  20                  25 cct ccc cta gag cct gct agg ccc aac cgc cac cca gag tcc tgt agg    195
Pro Pro Leu Glu Pro Ala Arg Pro Asn Arg His Pro Glu Ser Cys Arg
            30                  35                  40 gcc agt gaa gat gga ccc ctc aac agc agg gcc atc tcc ccc tgg aga    243
Ala Ser Glu Asp Gly Pro Leu Asn Ser Arg Ala Ile Ser Pro Trp Arg
            45                  50                  55 tat gag ttg gac aga gac ttg aac cgg ctc ccc cag gac ctg tac cac    291
Tyr Glu Leu Asp Arg Asp Leu Asn Arg Leu Pro Gln Asp Leu Tyr His
 60                  65                  70                  75 gcc cgt tgc ctg tgc ccg cac tgc gtc agc cta cag aca ggc tcc cac    339
Ala Arg Cys Leu Cys Pro His Cys Val Ser Leu Gln Thr Gly Ser His
            80                  85                  90
```

TABLE 3-continued

```
atg gac ccc cgg ggc aac tcg gag ctg ctc tac cac aac cag act gtc    387
Met Asp Pro Arg Gly Asn Ser Glu Leu Leu Tyr His Asn Gln Thr Val
             95                 100                 105 ttc tac cgg cgg cca tgc cat ggc gag aag ggc acc cac aag ggc tac    435
Phe Tyr Arg Arg Pro Cys His Gly Glu Lys Gly Thr His Lys Gly Tyr
        110                 115                 120 tgc ctg gag cgc agg ctg tac cgt gtt tcc tta gct tgt gtg tgt gtg    483
Cys Leu Glu Arg Arg Leu Tyr Arg Val Ser Leu Ala Cys Val Cys Val
125                 130                 135 cgg ccc cgt gtg atg ggc tag                                        504
Arg Pro Arg Val Met Gly
140                 145
```

MYQVVAFLAMVMGTHTYSHWPSCCPSKGQDTSEELLRWSTVPVPPLEPARPNRHPESCRASEDGPLN

SRAISPWRYELDRDLNRLPQDLYHARCLCPHCVSLQTGSHMDPRGNSELLYHNQTVFYRRPCHGERG

THKGYCLERRLYRVSLACVCVRPRVMG

Important predicted motifs include, e.g., cAMP PK sites at 21-24, 53-56, and 95-98; Ca phosphorylation sites at 15-17, 16-18, and 45-47; myristoly sites at 12-16, 115-119, and 118-122; N-glycosyl site at 104-107; phosphorylation sites at 21, 23, 43, 53, 56, 95, 98, and 131; PKC phosphorylation sites at 41-43 and 119-121; and tyrosine kinase site at 95-102.

Nucleotide sequence encoding a rodent, e.g., mouse, IL-174 polypeptide and predicted amino acid sequence. Also can use complementary nucleic acid sequences for many purposes. SEQ ID NO: 15 and 16.

```
CGG CAC AGG CGG CAC AAA GCC CGG AGA GTG GCT GAA GTG GAG CTC TGC    48
Arg His Arg Arg His Lys Ala Arg Arg Val Ala Glu Val Glu Leu Cys
 1               5                  10                  15

ATC TGT ATC CCC CCC AGA GCC TCT GAG CCA CAC CCA CCA CGC AGA ATC    96
Ile Cys Ile Pro Pro Arg Ala Ser Glu Pro His Pro Pro Arg Arg Ile
            20                  25                  30

CTG CAG GGC CAG CAA GGA TGG CCT CTC AAC AGC AGG GCC ATC TCT CCT    144
Leu Gln Gly Gln Gln Gly Trp Pro Leu Asn Ser Arg Ala Ile Ser Pro
        35                  40                  45

TGG AGC TAT GAG TTG GAC AGG GAC TTG AAT CGG GTC CCC CAG GAC TGG    192
Trp Ser Tyr Glu Leu Asp Arg Asp Leu Asn Arg Val Pro Gln Asp Trp
50                  55                  60

TAC CAC GCT CGA TGC CTG TGC CCA CAC TGC GTC ACG CTA CAG ACA GGC    240
Tyr His Ala Arg Cys Leu Cys Pro His Cys Val Thr Leu Gln Thr Gly
65                  70                  75                  80

TCC CAC ATG GAC CCG CTG GGC AAC TCC GTC CCA CTT TAC CAC AAC CAG    288
Ser His Met Asp Pro Leu Gly Asn Ser Val Pro Leu Tyr His Asn Gln
                85                  90                  95

ACG GTC TTC TAC CGG CGG CCA TGC ATG GCG AGG AAG GTA CCC ATC GCC    336
Thr Val Phe Tyr Arg Arg Pro Cys Met Ala Arg Lys Val Pro Ile Ala
                    100                 105                 110

GCT ACT GCT TGG AGC GCA GGT CTA CCG AGT CTC CTT GGC TTG TGT GTG    384
Ala Thr Ala Trp Ser Ala Gly Leu Pro Ser Leu Leu Gly Leu Cys Val
        115                 120                 125

TGT GCG GCC CCG GGT CAT GGC TTA GTC ATG CTC ACC ATC TGC CTG AGG    432
Cys Ala Ala Pro Gly His Gly Leu Val Met Leu Thr Ile Cys Leu Arg
130                 135                 140

TGAATGCCGG GTGGGAGAGA GGGCCAGGTG TACATCACCT GCCAATGCGG GCCGGGTTCA    492

AGCCTGCAAA GCCTACCTGA AGCAGCAGGT CCCGGGACAG GATGGAGACT TGGGGAGAAA    552

TCTGACTTTT GCACTTTTTG GAGCATTTTG GGAAGAGCAG GTTCGCTTGT GCTGTAGAGA    612

TGCTGTTG                                                             620
```

TABLE 3-continued

RHRRHKARRVAEVELCICIPPRASEPHPPRRILQGQQGWPLNSRAISPWSYELDRDLNRVPQDWYHA

RCLCPHCVTLQTGSHMDPLGNSVPLYHNQTVFYRRPCMARKVPIAATAWSAGLPSLLGLCVCAAPGH

GLVMLTICLR

Supplementary nucleotide sequence encoding a rodent, e.g., mouse,
IL-174 polypeptide and predicted amino acid sequence. Also can use
complementary nucleic acid sequences for many purposes. SEQ ID NO:
17 and 18.

| | | | | | | | | | | | | | | | | |
|---|---|---|---|---|---|---|---|---|---|---|---|---|---|---|---|---|
| atg | tac | cag | gct | gtt | gca | ttc | ttg | gca | atg | atc | gtg | gga | acc | cac | acc | 48 |
| Met | Tyr | Gln | Ala | Val | Ala | Phe | Leu | Ala | Met | Ile | Val | Gly | Thr | His | Thr | |
| | -15 | | | -10 | | | | -5 | | | | -1 | | | | |

| gtc | agc | ttg | cgg | atc | cag | gag | ggc | tgc | agt | cac | ttg | ccc | agc | tgc | tgc | 96 |
|---|---|---|---|---|---|---|---|---|---|---|---|---|---|---|---|---|
| Val | Ser | Leu | Arg | Ile | Gln | Glu | Gly | Cys | Ser | His | Leu | Pro | Ser | Cys | Cys | |
| 1 | | | | 5 | | | | | 10 | | | | | 15 | | |

| ccc | agc | aaa | gag | caa | gaa | ccc | ccg | gag | gag | tgg | ctg | aag | tgg | agc | tct | 144 |
|---|---|---|---|---|---|---|---|---|---|---|---|---|---|---|---|---|
| Pro | Ser | Lys | Glu | Gln | Glu | Pro | Pro | Glu | Glu | Trp | Leu | Lys | Trp | Ser | Ser | |
| | | | 20 | | | | | 25 | | | | 30 | | | | |

| gca | tct | gtg | tcc | ccc | cca | gag | cct | ctg | agc | cac | acc | cac | cac | gca | gaa | 192 |
|---|---|---|---|---|---|---|---|---|---|---|---|---|---|---|---|---|
| Ala | Ser | Val | Ser | Pro | Pro | Glu | Pro | Leu | Ser | His | Thr | His | His | Ala | Glu | |
| | | 35 | | | | | 40 | | | | | 45 | | | | |

| tcc | tgc | agg | gcc | agc | aag | gat | ggc | ccc | ctc | aac | agc | agg | gcc | atc | tct | 240 |
|---|---|---|---|---|---|---|---|---|---|---|---|---|---|---|---|---|
| Ser | Cys | Arg | Ala | Ser | Lys | Asp | Gly | Pro | Leu | Asn | Ser | Arg | Ala | Ile | Ser | |
| | 50 | | | | | 55 | | | | | 60 | | | | | |

| cct | tgg | agc | tat | gag | ttg | gac | agg | gac | ttg | aat | cgg | gtc | ccc | cag | gac | 288 |
|---|---|---|---|---|---|---|---|---|---|---|---|---|---|---|---|---|
| Pro | Trp | Ser | Tyr | Glu | Leu | Asp | Arg | Asp | Leu | Asn | Arg | Val | Pro | Gln | Asp | |
| 65 | | | | | 70 | | | | | 75 | | | | | 80 | |

| ctg | tac | cac | gct | cga | tgc | ctg | tgc | cca | cac | tgc | gtc | agc | cta | cag | aca | 336 |
|---|---|---|---|---|---|---|---|---|---|---|---|---|---|---|---|---|
| Leu | Tyr | His | Ala | Arg | Cys | Leu | Cys | Pro | His | Cys | Val | Ser | Leu | Gln | Thr | |
| | | | | 85 | | | | | 90 | | | | | 95 | | |

| ggc | tcc | cac | atg | gac | ccg | ctg | ggc | aac | tcc | gtc | cca | ctt | tac | cac | aac | 384 |
|---|---|---|---|---|---|---|---|---|---|---|---|---|---|---|---|---|
| Gly | Ser | His | Met | Asp | Pro | Leu | Gly | Asn | Ser | Val | Pro | Leu | Tyr | His | Asn | |
| | | | 100 | | | | | 105 | | | | | 110 | | | |

| cag | acg | gtc | ttc | tac | cgg | cgg | cca | tgc | cat | ggt | gag | gaa | ggt | acc | cat | 432 |
|---|---|---|---|---|---|---|---|---|---|---|---|---|---|---|---|---|
| Gln | Thr | Val | Phe | Tyr | Arg | Arg | Pro | Cys | His | Gly | Glu | Glu | Gly | Thr | His | |
| | | | 115 | | | | | 120 | | | | | 125 | | | |

| cgc | cgc | tac | tgc | ttg | gag | cgc | agg | ctc | tac | cga | gtc | tcc | ttg | gct | tgt | 480 |
|---|---|---|---|---|---|---|---|---|---|---|---|---|---|---|---|---|
| Arg | Arg | Tyr | Cys | Leu | Glu | Arg | Arg | Leu | Tyr | Arg | Val | Ser | Leu | Ala | Cys | |
| | | 130 | | | | | 135 | | | | | 140 | | | | |

| gtg | tgt | gtg | cgg | ccc | cgg | gtc | atg | gct | tagtcatgct caccacctgc | | | | | | | 527 |
|---|---|---|---|---|---|---|---|---|---|---|---|---|---|---|---|---|
| Val | Cys | Val | Arg | Pro | Arg | Val | Met | Ala | | | | | | | | |
| 145 | | | | 150 | | | | | | | | | | | | |

| ctgaggctga tgcccggttg ggagagaggg ccaggtgtac aatcaccttg ccaatgcggg | 587 |
|---|---|
| ccgggttcaa gccctccaaa gccctacctg aagcagcagg ctcccgggac aagatggagg | 647 |
| acttggggag aaactctgac ttttgcactt ttggaagca ttttgggaa ggagcaggtt | 707 |
| ccgcttgtgc tgctagagga tgctgttgtg gcatttctac tcaggaacgg actccaaagg | 767 |
| cctgctgacc ctggaagcca tactcctggc tcctttcccc tgaatccccc aactcctggc | 827 |
| acaggcactt tctccacctc tcccccttttg cctttgttg tgtttgtttg tgcatgccaa | 887 |
| ctctgcgtgc agccaggtgt aattgccttg aaggatggtt ctgaggtgaa agctgttatc | 947 |
| gaaagtgaag agatttatcc aaataaacat ctgtgttt | 985 |

TABLE 3-continued

MYQAVAFLAMIVGTHTVSLRIQEGCSHLPSCCPSKEQEPPEEWLKWSSASVSPPEPLSHTHHAESCR

ASKDGPLNSRAISPWSYELDRDLNRVPQDLYHARCLCPHCVSLQTGSHMDPLGNSVPLYHNQTVFYR

RPCHGEEGTHRRYCLERRLYRVSLACVCVRPRVMA

Important predicted motifs include, e.g., cAMP PK sites at 29-32 and 61-64; Ca phosphorylation sites at 18-20, 53-55, and 67-69; myristoly site at 123-127; N-glycosylation site at 112-114; and phosphorylation sites at 29, 31, 51, 53, 61, 64, 139, and 141; and PKC phosphorylation sites at 2-4, 49-51, and 127-129.

TABLE 4

Nucleotide sequence encoding a primate, e.g., human, IL-171 under IUPAC code. Also can use complementary nucleic acid sequences for many purposes. SEQ ID NO: 19

```
GACACGGATG AGGACCGCTA TCCACAGAAG CTGGCCTTCG CCGAGTGCCT GTGCAGAGGC      60

TGTATCGATG CACGGACGGG CCGCGAGACA GCTGCGCTCA ACTCCGTGCG GCTGCTCCAG     120

AGCCTGCTGG TGCTGCGCCG CCGGCCCTGC TCCCGCGACG GCTCGGGGCT CCCCACACCT     180

GGGGCCTTTG CCTTCCACAC CGAGTTCATC CACGTCCCCG TCGGCTGCAC CTGCGTGCTG     240

CCCCGTTCAA GTGTGACCGC CAAGGCCGTG GGGCCCTTAG NTGACACCGT GTGCTCCCCA     300

GAGGGACCCC TATTTATGGG AATTATGGTA TTATATGCTT CCCACATACT TGGGGCTGGC     360

ATCCCGNGCT GAGACAGCCC CCTGTTCTAT TCAGCTATAT GGGGAGAAGA GTAGACTTTC     420

AGCTAAGTGA AAAGTGNAAC GTGCTGACTG TCTGCTGTCG TNCTACTNAT GCTAGCCCGA     480

GTGTTCACTC TGAGCCTGTT AAATATAGGC GGTTATGTAC C                         521
```

SEQ ID NO: 20 and 21 are PATENTIN translatable cDNA and polypeptide sequences:

```
GAC ACG GAT GAG GAC CGC TAT CCA CAG AAG CTG GCC TTC GCC GAG TGC        48
Asp Thr Asp Glu Asp Arg Tyr Pro Gln Lys Leu Ala Phe Ala Glu Cys
 1               5                  10                  15

CTG TGC AGA GGC TGT ATC GAT GCA CGG ACG GGC CGC GAG ACA GCT GCG        96
Leu Cys Arg Gly Cys Ile Asp Ala Arg Thr Gly Arg Glu Thr Ala Ala
             20                  25                  30

CTC AAC TCC GTG CGG CTG CTC CAG AGC CTG CTG GTG CTG CGC CGC CGG       144
Leu Asn Ser Val Arg Leu Leu Gln Ser Leu Leu Val Leu Arg Arg Arg
         35                  40                  45

CCC TGC TCC CGC GAC GGC TCG GGG CTC CCC ACA CCT GGG GCC TTT GCC       192
Pro Cys Ser Arg Asp Gly Ser Gly Leu Pro Thr Pro Gly Ala Phe Ala
     50                  55                  60

TTC CAC ACC GAG TTC ATC CAC GTC CCC GTC GGC TGC ACC TGC GTG CTG       240
Phe His Thr Glu Phe Ile His Val Pro Val Gly Cys Thr Cys Val Leu
 65                  70                  75                  80

CCC CGT TCA AGT GTG ACC GCC AAG GCC GTG GGG CCC TTA GnT GAC ACC       288
Pro Arg Ser Ser Val Thr Ala Lys Ala Val Gly Pro Leu Xaa Asp Thr
             85                  90                  95

GTG TGC TCC CCA GAG GGA CCC CTA TTT ATG GGA ATT ATG GTA TTA TAT       336
Val Cys Ser Pro Glu Gly Pro Leu Phe Met Gly Ile Met Val Leu Tyr
         100                 105                 110

GCT TCC CAC ATA CTT GGG GCT GGC ATC CCG nGC TGAGACAGCC CCTGTTCTA      389
Ala Ser His Ile Leu Gly Ala Gly Ile Pro Xaa
         115                 120

TTCAGCTATA TGGGGAGAAG AGTAGACTTT CAGCTAAGTG AAAAGTGCAA CGTGCTGACT     449

GTCTGCTGTC GTCCTACTCA TGCTAGCCCG AGTGTTCACT CTGAGCCTGT AAATATAGG      509

CGGTTATGTA CC                                                         521
```

TABLE 4-continued

DTDEDRYPQKLAFAECLCRGCIDARTGRETAALNSVRLLQSLLVLRRRPCSRDGSGLPTPGAFAFHT

EFIHVPVGCTCVLPRSSVTAKAVGPLXDTVCSPEGPLFMGIMVLYASHILGAGIPX

Supplementary nucleotide sequence encoding a primate, e.g., human, IL-171. Also can use complementary nucleic acid sequences for many purposes. SEQ ID NO: 22 and 23:

```
gtgtggcctc aggtataaga gcggctgctg ccaggtgcat ggccaggtgc acctgtggga        60
ttgccgccag gtgtgcaggc cgctccaagc ccagcctgcc ccgctgccgc cacc atg        117
                                                              Met acg ctc ctc ccc ggc ctc ctg ttt ctg acc tgg ctg cac aca tgc ctg        165
Thr Leu Leu Pro Gly Leu Leu Phe Leu Thr Trp Leu His Thr Cys Leu
    -15             -10                 -5                  -1 gcc cac cat gac ccc tcc ctc agg ggg cac ccc cac agt cac ggt acc        213
Ala His His Asp Pro Ser Leu Arg Gly His Pro His Ser His Gly Thr
 1           5                  10                  15 cca cac tgc tac tcg gct gag gaa ctg ccc ctc ggc cag gcc ccc cca        261
Pro His Cys Tyr Ser Ala Glu Glu Leu Pro Leu Gly Gln Ala Pro Pro
             20                  25                  30 cac ctg ctg gct cga ggt gcc aag tgg ggg cag gct ttg cct gta gcc        309
His Leu Leu Ala Arg Gly Ala Lys Trp Gly Gln Ala Leu Pro Val Ala
         35                  40                  45 ctg gtg tcc agc ctg gag gca gca agc cac agg ggg agg cac gag agg        357
Leu Val Ser Ser Leu Glu Ala Ala Ser His Arg Gly Arg His Glu Arg
     50                  55                  60 ccc tca gct acg acc cag tgc ccg gtg ctg cgg ccg gag gag gtg ttg        405
Pro Ser Ala Thr Thr Gln Cys Pro Val Leu Arg Pro Glu Glu Val Leu
 65                  70                  75                  80 gag gca gac acc cac cag cgc tcc atc tca ccc tgg aga tac cgt gtg        453
Glu Ala Asp Thr His Gln Arg Ser Ile Ser Pro Trp Arg Tyr Arg Val
                 85                  90                  95 gac acg gat gag gac cgc tat cca cag aag ctg gcc ttc gcc gag tgc        501
Asp Thr Asp Glu Asp Arg Tyr Pro Gln Lys Leu Ala Phe Ala Glu Cys
             100                 105                 110 ctg tgc aga ggc tgt atc gat gca cgg acg ggc cgc gag aca gct gcg        549
Leu Cys Arg Gly Cys Ile Asp Ala Arg Thr Gly Arg Glu Thr Ala Ala
         115                 120                 125 ctc aac tcc gtg cgg ctg ctc cag agc ctg ctg gtg ctg cgc cgc cgg        597
Leu Asn Ser Val Arg Leu Leu Gln Ser Leu Leu Val Leu Arg Arg Arg
     130                 135                 140 ccc tgc tcc cgc gac ggc tcg ggg ctc ccc aca cct ggg gcc ttt gcc        645
Pro Cys Ser Arg Asp Gly Ser Gly Leu Pro Thr Pro Gly Ala Phe Ala
145                 150                 155                 160 ttc cac acc gag ttc atc cac gtc ccc gtc ggc tgc acc tgc gtg ctg        693
Phe His Thr Glu Phe Ile His Val Pro Val Gly Cys Thr Cys Val Leu
                 165                 170                 175 ccc cgt tca gtg tgaccgccga ggccgtgggg cccctagact ggacacgtgt            745
Pro Arg Ser Val
             180 gctccccaga gggcaccccc tatttatgtg tatttattgg tatttatatg cctcccccaa      805 cactacccct ggggtctggg cattcccgtg tctggagga cagcccccca ctgttctcct       865 catctccagc ctcagtagtt ggggtagaa ggagctcagc acctcttcca gcccttaaag       925 ctgcagaaaa ggtgtcacac ggctgcctgt accttggctc cctgtcctgc tcccggcttc      985 ccttacccta tcactggcct caggccccg caggctgcct cttcccaacc tccttggaag      1045 taccctgtt tcttaaacaa ttatttaagt gtacgtgtat tattaaactg atgaacacat      1105 cc                                                                    1107
```

TABLE 4-continued

MTLLPGLLFLTWLHTCLAHHDPSLRGHPHSHGTPHCYSAEELPLGQAPPHLLARGAKWGQALPVALV

SSLEAASHRGRHERPSATTQCPVLRPEEVLEADTHQRSISPWRYRVDTDEDRYPQKLAFAECLCRGC

IDARTGRETAALNSVRLLQSLLVLRRRPCSRDGSGLPTPGAFAFHTEFIHVPVGCTCVLPRSV

TABLE 5

Nucleotide sequence encoding a primate, e.g., human, IL-175 sequence under IUPAC cgde. Also can use complementary nucleic acid sequences for many purposes. SEQ ID NO: 24:

```
GAGAAAGAGC TTCCTGCACA AAGTAAGCCA CCAGCGCAAC ATGACAGTGA AGACCCTGCA    60

TGGCCCAGCC ATGGTCAAGT ACTTGCTGCT GTCGATATTG GGCTTGCCT TTCTGAGTGA   120

GGCGGCAGCT CGGAAAATCC CCAAAGTAGG ACATACTTTT TTCCAAAAGC CTGAGAGTTG   180

CCCGCCTGTG CCAGGAGGTA GTATGAAGCT TGACATTGGC ATCATCAATG AAAACCAGCG   240

CGTTTCCATG TCACGTAACA TCGAGAGCCG CTCCACCTCC CCCTGGAATT ACACTGTCAC   300

TTGGGACCCC AACCGGTACC CCTCGAAGTT GTACAGGCCC AAGTGTAGGA ACTTGGGCTG   360

TATCAATGCT CAAGGAAAGG AAGACATCTN CATGAATTCC GTC                     403
```

SEQ ID NO: 25 and 26 are PATENTIN translatable cDNA and polypeptide sequences. Predicted signal cleavage site indicated, but may be a few residues on either side; putative glycosylation site at residues 53-55:

```
GAGAAAGAGC TTCCTGCACA AAGTAAGCCA CCAGCGCAAC ATGACAGTGA AGACCCTGCA
60

TGGCCCAGCC ATG GTC AAG TAC TTG CTG CTG TCG ATA TTG GGG CTT GCC
109
            Met Val Lys Tyr Leu Leu Leu Ser Ile Leu Gly Leu Ala
                -20              -15                  -10

TTT CTG AGT GAG GCG GCA GCT CGG AAA ATC CCC AAA GTA GGA CAT ACT
157
Phe Leu Ser Glu Ala Ala Ala Arg Lys Ile Pro Lys Val Gly His Thr
        -5                   1               5

TTT TTC CAA AAG CCT GAG AGT TGC CCG CCT GTG CCA GGA GGT AGT ATG
205
Phe Phe Gln Lys Pro Glu Ser Cys Pro Pro Val Pro Gly Gly Ser Met
 10              15                  20              25

AAG CTT GAC ATT GGC ATC ATC AAT GAA AAC CAG CGC GTT TCC ATG TCA
253
Lys Leu Asp Ile Gly Ile Ile Asn Glu Asn Gln Arg Val Ser Met Ser
                30                  35                  40

CGT AAC ATC GAG AGC CGC TCC ACC TCC CCC TGG AAT TAC ACT GTC ACT
301
Arg Asn Ile Glu Ser Arg Ser Thr Ser Pro Trp Asn Tyr Thr Val Thr
            45                  50                  55

TGG GAC CCC AAC CGG TAC CCC TCG AAG TTG TAC AGG CCC AAG TGT AGG
349
Trp Asp Pro Asn Arg Tyr Pro Ser Lys Leu Tyr Arg Pro Lys Cys Arg
            60                  65                  70

AAC TTG GGC TGT ATC AAT GCT CAA GGA AAG GAA GAC ATC TCC ATG AAT
397
Asn Leu Gly Cys Ile Asn Ala Gln Gly Lys Glu Asp Ile Ser Met Asn
        75                  80                  85

TCC GTC
403
Ser Val
 90
```

TABLE 5-continued

MVKYLLLSILGLAFLSEAAARKIPKVGHTFFQKPESCPPVPGGSMKLDIGIINENQRVSMSRNIESR

STSPWNYTVTWDPNRYPSKLYRPKCRNLGCINAQGKEDIXMNSV

Particularly interesting segments include, e.g., those which
begin or end with arg1; cys17; pro18, pro19; val20; thr49; ser50;
arg69; pro70; and the end of the sequence available.

TABLE 6

Nucleotide sequence encoding a primate, e.g., human,
IL-176. Also can use complementary nucleic acid sequences for
many purposes. SEQ ID NO: 27 and 28:

```
tc gtg ccg tat ctt ttt aaa aaa att att ctt cac ttt ttt gcc tcc      47
   Val Pro Tyr Leu Phe Lys Lys Ile Ile Leu His Phe Phe Ala Ser
    1               5                   10                  15 tat tac ttg tta ggg aga ccc aat ggt agt ttt att cct tgg gga tac     95
Tyr Tyr Leu Leu Gly Arg Pro Asn Gly Ser Phe Ile Pro Trp Gly Tyr
            20                  25                  30 ata gta aat act tca tta aag tcg agt aca gaa ttt gat gaa aag tgt    143
Ile Val Asn Thr Ser Leu Lys Ser Ser Thr Glu Phe Asp Glu Lys Cys
        35                  40                  45 gga tgt gtg gga tgt act gcc gcc ttc aga agt cca cac act gcc tgg    191
Gly Cys Val Gly Cys Thr Ala Ala Phe Arg Ser Pro His Thr Ala Trp
    50                  55                  60 agg gag aga act gct gtt tat tca ctg att aag cat ttg ctg tgt acc    239
Arg Glu Arg Thr Ala Val Tyr Ser Leu Ile Lys His Leu Leu Cys Thr
65                  70                  75 aac tac ttt tca tgt ctt atc tta att ctc ata aca gtc att            281
Asn Tyr Phe Ser Cys Leu Ile Leu Ile Leu Ile Thr Val Ile
 80                  85                  90 tgatatttta aaaaccccca gaaatctgag aaagagataa agtggtttgc tcaaggttat  341
agaacagact accatgtgtt gtatttcaga ttttaattca tgtttgtctg atttttaagtt 401 ttgttcgctt gccagggtac cccacaaaaa tgccaggcag gcattttca tgatgcactt   461 gagatacctg aaatgacagg gtagcatcac acctgagagg ggtaaaggat gggaacctac  521
cttccatggc cgctgcttgg cagtctcttg ctgcatgcta gcagagccac tgtatatgtg  581
ccgaggctct gagaattaac tgcttaaaga actgccttct ggagggagaa gagcacaaga  641
tcacaattaa ccatatacac atcttactgt gcgaggtcat tgagcaatac aggagggatt  701
ttatacattt tagcaactat cttcaaaacc tgagctatag ttgtattctg cccccttcct  761
ctgggcaaaa gtgtaaaagt ttg                                          784
```

VPYLFKKIILHFFASYYLLGRPNGSFIPWGYIVNTSLKSSTEFDEKCGCVGCTAAFRSPHTAWRERT

AVYSLIKHLLCTNYFSCLILILITVI

Nucleotide sequence encoding a primate, e.g., human, IL-177. Also
can use complementary nucleic acid sequences for many purposes.
SEQ ID NO: 29 and 30:

```
gtg act gta ttg tgg gga cag gaa gca caa att ccc atg tgg atc act     48
Val Thr Val Leu Trp Gly Gln Glu Ala Gln Ile Pro Met Trp Ile Thr
 1               5                   10                  15 agg aga gat aat aag tgg ggt cat ttc acc cct tgg tcc cct gct tcc     96
Arg Arg Asp Asn Lys Trp Gly His Phe Thr Pro Trp Ser Pro Ala Ser
            20                  25                  30 aga ccc aaa gag gcc tac atg gca ttg tgc ttc ctt ctt agt tgt agg    144
Arg Pro Lys Glu Ala Tyr Met Ala Leu Cys Phe Leu Leu Ser Cys Arg
        35                  40                  45 agg tgt gag ata caa tca ttt gcc tct gac ttt gag ggt tgg tcc        189
Arg Cys Glu Ile Gln Ser Phe Ala Ser Asp Phe Glu Gly Trp Ser
    50                  55                  60
```

TABLE 6-continued

```
tagcatgccc ctgaccagta gccccttaaa tacttcattg atatggaagg tctctgaatc 249 ttcgtgggct taatctacca ctctctgaag ttcttatgtc tttcaaaggc ctctaaaatc 309 tctgccatgt cttgctcatc cagttgttag catgatgtca ttgatacagt ggactttgga 369 atctaagtgg ggagacactg gtaagtgacc aattacttca cctgtggtgt gcaagccaga 429 tcaggaagcc tctacctgca cgacaacaca t                              460
```

VTVLWGQEAQIPMWITRRDNKWGHFTPWSPASRPKEAYMALCFLLSCRRCEIQSFASDFEGWS

Purified protein or polypeptides are useful for generating antibodies by standard methods, as described above. Synthetic peptides or purified protein can be presented to an immune system to generate a specific binding composition, e.g., monoclonal or polyclonal antibodies. See, e.g., Coligan (1991) *Current Protocols in Immunology* Wiley/Greene; and Harlow and Lane (1989) *Antibodies: A Laboratory Manual* Cold Spring Harbor Press.

For example, the specific binding composition could be used for screening of an expression library made from a cell line which expresses an IL-170 protein. The screening can be standard staining of surface expressed protein, or by panning. Screening of intracellular expression can also be performed by various staining or immunofluorescence procedures. The binding compositions could be used to affinity purify or sort out cells expressing the protein.

This invention contemplates use of isolated DNA or fragments to encode a biologically active corresponding IL-170 protein or polypeptide. In addition, this invention covers isolated or recombinant DNA which encodes a biologically active protein or polypeptide and which is capable of hybridizing under appropriate conditions with the DNA sequences described herein. Said biologically active protein or polypeptide can be an intact antigen, or fragment, and have an amino acid sequence as disclosed in Tables 1-6. Further, this invention covers the use of isolated or recombinant DNA, or fragments thereof, which encode proteins which are homologous to an IL-170 protein or which were isolated using cDNA encoding an IL-170 protein as a probe. The isolated DNA can have the respective regulatory sequences in the 5' and 3' flanks, e.g., promoters, enhancers, poly-A addition signals, and others.

TABLE 7

```
Alignment gf various CTLA-8/IL-170 family members. The
rat CTLA-8 sequence is SEQ ID NO: 31 (see GB L13B39; 293329/30);
mouse CTLA-8 sequence is SEQ ID NO: 32 (see GB 1469917/8); human
CTLA-8 is SEQ ID NO: 33 (see GB 1332659; 115222/3); and Herpes
Saimiri virus ORF13 is SEQ ID NO: 34 (see GB Y13183; 2370235)
CLUSTAL X (1.64b) multiple sequence alignment
174_Mu   ---------MYQAVAFLAMIVGTHTVSLRI----QEGCSHLPSCCPSKEQEPPEEWLKWS 174_Hu   ---------MYQVVAFLAMVMGTHTY---------S---HWPSCCPSKGQDTSEELLRWS 172_Mu   ------MDWPHNLLFLLTISIFLGLGQPRSPKSKRKGQGRPGPLVPGPHQVPLDLVSRMK 172_Hu   ------MDWPHSLLFLLAISIFLAPSHPRNTKGKRKGQGRPSPLAPGPHQVPLDLVSRVK 173_Mu   --MLGTLVWMLLVGFLLALAPGRAAGALRT--GRRP--ARPRDCADRPEELLEQLYGRLA 173_Hu   ---------MLVAGFLLALPPSWAAGAPRA--GRRP--ARPRGCADRPEELLEQLYGRLA 17_Hu    --MTPGKTSLVSLLLLLSLEAIVKAGITIP---------RNPGCPNSEDKNFPRTVMVNL 17_Ms    --MTFRKTSLV-LLLLLSIDCIVKSEITSA---------QTPRCLAANN-SFPRSVMVTL 17_Rt    --------MCLMLLLLLNLEATVKAAVLIP---------QSSVCPNAEANNFLQNVKVNL 17_Mu    -----------MLLLLLSLAATVKAAAIIP---------QSSACPNTEAKDFLQNVKVNL 175_Mu   -------MVKYLLLSILGLAFLSEAAARKIPKVGHTFFQKPESCPPVPGGSMKLDIGIIN 171_Mu   MTLLPGLLFLTWLHTCLAMHDPSLRGHPHSHGTPHCYSAEELPLGQAPPHLLARGAKWGQ
                                  *          .

174_Mu   S---------ASVSPP-EPLSHTHHAES---CRASKD-GPLNSRAISPWSYELDRDLNRV

174_Hu   T---------VPVPPL-EPARPNRMPES---CRASED-GPLNSRAISPWRYELDRDLNRL

172_Hu   P-YARMEEYERNIEEMVAQLRNSSELAQ-RKCEVNLQLWMSNKRSLSPWGYSINHDPSRI

172_Mu   P-YARMEEYERNLGEMVAQLRNSSEPAK-KKCEVNLQLWLSNKRSLSPWGYSINHDPSRI

173_Mu   AGVLSAFHHTLQLGPR-EQARNASCPAGGRAADRRFR-PPTNLRSVSPWAYRISYDPARF

173_Hu   AGVLSAFHHTLQLGPR-EQARNASCPAGGRPADRRFR-PPTNLRSVSPWAYRISYDPARY
```

TABLE 7-continued

```
17_Mu    N-----------------IHNRNTNTN-----P-KRSSDYYNRSTSPWNLHRNEDPERY

17_Hs    S-----------------IRNWNTSS--------KRASDYYNRSTSPWTLHRNEDQDRY

17_Rt    K-----------------VINSLSSKA-----SSRRPSDYLNRSTSPWTLSRNEDPDRY

17_Mu    K-----------------VFNSLGAKV-----SSRRPSDYLNRSTSPWTLHRNEDPDRY

175_Mu   E-----------------N--QRVSMS--------R--NIESRSTSPWNYTVTWDPNRY

171_Hu   ALPVALVSSLEAASHRGRHERPSATTQCPVLRPEEVLEADTHQRSISPWRYRVDTDEDRY
                                                   *:  ***         * *

174_Mu   PQDLYHARCLCPHCVSLQTGSHMDPLGNSVPLYHNQTVFYRR--PCHGEEGTHRRYCLER

174_Hu   PQDLYHARCLCPHCVSLQTGSHMDPRGNSELLYRNQTVFYRR--PCHGEKGTHKGYCLER

172_Hu   PVDLPEARCLCLGCVNPFTM-QEDRSMVSVPVFS-QVPVRRR--LCPPPP--RTGPCRQR

172_Mu   PADLPEARCLCLGCVNPFTM-QEDRSMVSVPVFS-QVPVRRR--LCPQPP--RPGPCRQR

173_Mu   PRYLPEAYCLCRGCLTGLYG-EEDFRFRSTPVFS-PAVVLRRTAACAG------GRSVYA

173_Hu   PRYLPEAYCLCRGCLTGLFG-EEDVRFRSAPVYM-PTVVLRRTPACAG------GRSVYT

17_Hu    PSVIWEAKCRHLGCINADGN--VDYHMNSVPIQQEILVLRREPPHCPN---------SFR

17_Hs    PSVIWEAKCRYLGCVNADGN--VDYHMNSVPIQQEILVVRKGHQPCPN---------SFR

17_Rt    PSVIWEAQCRHQRCVNAEGK--LDHHMNSVLIQQEILVLKREPEKCPF---------TFR

17_Mu    PSVIWEAQCRHQRCVNAEGK--LDHHMNSVLIQQEILVLKREPESCPF---------TFR

175_Hu   PSEVVQAQCRNLGCINAQGK--EDISMNSVPIQQETLVVRRKHQGCSV---------SFQ

171_Hu   PQKLAFAECLCRGCIDARTG-RETAALNSVRLLQSLLVLRRRPCSRDGSGLPTPGAFAFH
                   *  : * *    *:                    *   :      . :

174_Mu   RLYR-VSLACVCVRPRVMA------------------------

174_Hu   RLYR-VSLACVCVRPRVMG------------------------

172_Hu   AVMETIAVGCTCIF-----------------------------

172_Mu   VVMETIAVGCTCIF-----------------------------

173_Mu   EHYITIPVGCTCVPEPDKSADSANSSMDK----LLLGPADRPAGR

173_Hu   EAYVTIPVGCTCVPEPEKDADSINSSIDKQGAKLLLGPNDAPAGP

17_Hu    LEKILVSVGCTCVTPIVHHVA----------------------

17_Hs    LEKMLVTVGCTCVTPIVHNVD----------------------

17_Rt    VEKMLVGVGCTCVSSIVRHAS----------------------

17_Mu    VEKMLVGVGCTCVASIVRQAA----------------------

175_Hu   LEKVLVTVGCTCVTPVIHHVQ----------------------

171_Mu   TEFIHVPVGCTCVLPRSV-------------------------
                :  :.*.*:
Particularly intersting segments include, e.g., those
corresponding to the segments of IL-172 or IL-175, indicated above,
with the other family members.
```

An "isolated" nucleic acid is a nucleic acid, e.g., an RNA, DNA, or a mixed polymer, which is substantially separated from other components which naturally accompany a native sequence, e.g., ribosomes, polymerases, and flanking genomic sequences from the originating species. The term embraces a nucleic acid sequence which has been removed from its naturally occurring environment, and includes recombinant or cloned DNA isolates and chemically synthesized analogs or analogs biologically synthesized by heterologous systems. A substantially pure molecule includes isolated forms of the molecule. Alternatively, a purified species may be separated from host components from a recombinant expression system. The size of homology of such a nucleic acid will typically be less than large vectors, e.g., less than tens of kB, typically less than several kB, and preferably in the 2-6 kB range.

An isolated nucleic acid will generally be a homogeneous composition of molecules, but will, in some embodiments, contain minor heterogeneity. This heterogeneity is typically found at the polymer ends or portions not critical to a desired biological function or activity.

A "recombinant" nucleic acid is defined either by its method of production or its structure. In reference to its method of production, e.g., a product made by a process, the process is use of recombinant nucleic acid techniques, e.g., involving human intervention in the nucleotide sequence, typically selection or production. Alternatively, it can be a nucleic acid made by generating a sequence comprising fusion of two fragments which are not naturally contiguous to each other, but is meant to exclude products of nature, e.g., naturally occurring mutants. Thus, for example, products made by transforming cells with any unnaturally occurring vector is encompassed, as are nucleic acids comprising sequence derived using any synthetic oligonucleotide process. Such is often done to replace a codon with a redundant codon encoding the same or a conservative amino acid, while typically introducing or removing a sequence recognition site. Alternatively, it is performed to join together nucleic acid segments of desired functions to generate a single genetic entity comprising a desired combination of functions not found in the commonly available natural forms. Restriction enzyme recognition sites are often the target of such artificial manipulations, but other site specific targets, e.g., promoters, DNA replication sites, regulation sequences, control sequences, or other useful features may be incorporated by design. A similar concept is intended for a recombinant, e.g., fusion, polypeptide. Specifically included are synthetic nucleic acids which, by genetic code redundancy, encode polypeptides similar to fragments of these antigens, and fusions of sequences from various different species variants.

A significant "fragment" in a nucleic acid context is a contiguous segment of at least about 17 nucleotides, generally at least 20 nucleotides, more generally at least 23 nucleotides, ordinarily at least 26 nucleotides, more ordinarily at least 29 nucleotides, often at least 32 nucleotides, more often at least 35 nucleotides, typically at least 38 nucleotides, more typically at least 41 nucleotides, usually at least 44 nucleotides, more usually at least 47 nucleotides, preferably at least 50 nucleotides, more preferably at least 53 nucleotides, and in particularly preferred embodiments will be at least 56 or more nucleotides. Said fragments may have termini at any location, but especially at boundaries between structural domains.

In other embodiments, the invention provides polynucleotides (or polypeptides) which comprise a plurality of distinct, e.g., nonoverlapping, segments of the specified length. Typically, the plurality will be at least two, more usually at least three, and preferably 5, 7, or even more. While the length minima are provided, longer lengths, of various sizes, may be appropriate, e.g., one of length 7, and two of length 12.

A DNA which codes for an IL-170 protein will be particularly useful to identify genes, mRNA, and cDNA species which code for related or homologous proteins, as well as DNAs which code for homologous proteins from different species. There are likely homologues in other species, including primates. Various CTLA-8 proteins should be homologous and are encompassed herein. However, even proteins that have a more distant evolutionary relationship to the antigen can readily be isolated under appropriate conditions using these sequences if they are sufficiently homologous. Primate CTLA-8 protein proteins are of particular interest.

This invention further covers recombinant DNA molecules and fragments having a DNA sequence identical to or highly homologous to the isolated DNAs set forth herein. In particular, the sequences will often be operably linked to DNA segments which control transcription, translation, and DNA replication.

Alternatively, recombinant clones derived from the genomic sequences, e.g., containing introns, will be useful for transgenic studies, including, e.g., transgenic cells and organisms, and for gene therapy. See, e.g., Goodnow (1992) "Transgenic Animals" in Roitt (ed.) *Encyclopedia of Immunology* Academic Press, San Diego, pp. 1502-1504; Travis (1992) *Science* 256:1392-1394; Kuhn, et al. (1991) *Science* 254:707-710; Capecchi (1989) *Science* 244:1288; Robertson (ed. 1987) *Teratocarcinomas and Embryonic Stem Cells: A Practical Approach* IRL Press, Oxford; Rosenberg (1992) *J. Clinical Oncology* 10:180-199; and Cournoyer and Caskey (1993) *Ann. Rev. Immunol.* 11:297-329.

Homologous nucleic acid sequences, when compared, exhibit significant similarity. The standards for homology in nucleic acids are either measures for homology generally used in the art by sequence comparison or based upon hybridization conditions. The hybridization conditions are described in greater detail below.

Substantial homology in the nucleic acid sequence comparison context means either that the segments, or their complementary strands, when compared, are identical when optimally aligned, with appropriate nucleotide insertions or deletions, in at least about 50% of the nucleotides, generally at least 56%, more generally at least 59%, ordinarily at least 62%, more ordinarily at least 65%, often at least 68%, more often at least 71%, typically at least 74%, more typically at least 77%, usually at least 80%, more usually at least about 85%, preferably at least about 90%, more preferably at least about 95 to 98% or more, and in particular embodiments, as high at about 99% or more of the nucleotides. Alternatively, substantial homology exists when the segments will hybridize under selective hybridization conditions, to a strand, or its complement, typically using a sequence derived from Table 2, 3, or 6. Typically, selective hybridization will occur when there is at least about 55% homology over a stretch of at least about 14 nucleotides, preferably at least about 65%, more preferably at least about 75%, and most preferably at least about 90%. See, Kanehisa (1984) *Nuc. Acids Res.* 12:203-213. The length of homology comparison, as described, may be over longer stretches, and in certain embodiments will be over a stretch of at least about 17 nucleotides, usually at least about 20 nucleotides, more usually at least about 24 nucleotides, typically at least about 28 nucleotides, more typically at least about 40 nucleotides, preferably at least about 50 nucleotides, and more preferably at least about 75 to 100 or more nucleotides.

Stringent conditions, in referring to homology in the hybridization context, will be stringent combined conditions of salt, temperature, organic solvents, and other parameters, typically those controlled in hybridization reactions. Stringent temperature conditions will usually include temperatures in excess of about 30° C., more usually in excess of about 37° C., typically in excess of about 45° C., more typically in excess of about 55° C., preferably in excess of about 65° C., and more preferably in excess of about 70° C. Stringent salt conditions will ordinarily be less than about 1000 mM, usually less than about 500 mM, more usually less than about 400 mM, typically less than about 300 mM, preferably less than about 200 mM, and more preferably less than about 150 mM. However, the combination of parameters is much more important than the measure of any single parameter. See, e.g., Wetmur and Davidson (1968) *J. Mol. Biol.* 31:349-370. Hybridization under stringent conditions should give a background of at least 2-fold over background, preferably at least 3-5 or more.

Alternatively, for sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optical alignment of sequences for comparison can be conducted, e.g., by the local homology algorithm of Smith and Waterman (1981) *Adv. Appl. Math.* 2:482, by the homology alignment algorithm of Needleman and Wunsch (1970) *J. Mol. Biol.* 48:443, by the search for similarity method of Pearson and Lipman (1988) *Proc. Nat'l Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel, et al., supra).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng and Doolittle (1987) *J. Mol. Evol.* 35:351-360. The method used is similar to the method described by Higgins and Sharp (1989) *CABIOS* 5:151-153. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described Altschul, et al. (1990) *J. Mol. Biol.* 215:403-410. Software for performing BLAST analyses is publicly available through the National Center for Biotechnology Information (http:www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul, et al., supra). These initial neighborhood word hits act as seeds for initiating searches to find longer HSPs containing them. The word hits are then extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff and Henikoff (1989) *Proc. Nat'l Acad. Sci. USA* 89:10915) alignments (B) of 50, expectation (E) of 10, M=5, N=4, and a comparison of both strands.

In addition to calculating percent sequence identity, the BLAST algorithm also performs a statistical analysis of the similarity between two sequences (see, e.g., Karlin and Altschul (1993) *Proc. Nat'l Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences of polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

CTLA-8-like proteins from other mammalian species can be cloned and isolated by cross-species hybridization of closely related species, e.g., human, as disclosed in Tables 1-7. Homology may be relatively low between distantly related species, and thus hybridization of relatively closely related species is advisable. Alternatively, preparation of an antibody preparation which exhibits less species specificity may be useful in expression cloning approaches.

III. Purified IL-170 Protein

The predicted sequence of primate, e.g., human, and rodent, e.g., mouse, IL-173 polypeptide sequence is shown in Table 2. Similarly, in Table 3, is provided primate, e.g., human, IL-174 sequence, and is assigned SEQ ID NO: 14. A rodent, e.g., murine, IL-174 is also described in Table 3. The peptide sequences allow preparation of peptides to generate antibodies to recognize such segments.

As used herein, the terms "primate IL-170 protein" and "rodent IL-170 protein" shall encompass, when used in a protein context, a protein having designated amino acid sequences shown in Tables 1-7, or a significant fragment of such a protein. It also refers to a primate or rodent derived polypeptide which exhibits similar biological function or interacts with IL-170 protein specific binding components. These binding components, e.g., antibodies, typically bind to an IL-170 protein with high affinity, e.g., at least about 100 nM, usually better than about 30 nM, preferably better than about 10 nM, and more preferably at better than about 3 nM. Homologous proteins would be found in mammalian species other than rat or humans, e.g., mouse, primates, and in the herpes virus genome, e.g., ORF13. Non-mammalian species should also possess structurally or functionally related genes and proteins.

The term "polypeptide" as used herein includes a significant fragment or segment, and encompasses a stretch of amino acid residues of at least about 8 amino acids, generally at least 10 amino acids, more generally at least 12 amino acids, often at least 14 amino acids, more often at least 16 amino acids, typically at least 18 amino acids, more typically at least 20 amino acids, usually at least 22 amino acids, more usually at least 24 amino acids, preferably at least 26 amino acids, more preferably at least 28 amino acids, and, in particularly preferred embodiments, at least about 30 or more amino acids. The specific ends of such a segment will be at any combinations within the protein, preferably encompassing structural domains.

The term "binding composition" refers to molecules that bind with specificity to IL-170 protein, e.g., in a ligand-receptor type fashion, an antibody-antigen interaction, or compounds, e.g., proteins which specifically associate with IL-170 protein, e.g., in a natural physiologically relevant protein-protein interaction, either covalent or non-covalent. The molecule may be a polymer, or chemical reagent. No implication as to whether IL-170 protein is either the ligand or the receptor of a ligand-receptor interaction is represented, other than the interaction exhibit similar specificity, e.g., specific affinity. A functional analog may be a protein with structural modifications, or may be a wholly unrelated molecule, e.g., which has a molecular shape which interacts with the appropriate binding determinants. The proteins may serve as agonists or antagonists of a receptor, see, e.g., Goodman, et al. (eds. 1990) *Goodman & Gilman's: The Pharmacological Bases of Therapeutics* (8th ed.), Pergamon Press.

Solubility of a polypeptide or fragment depends upon the environment and the polypeptide. Many parameters affect polypeptide solubility, including temperature, electrolyte environment, size and molecular characteristics of the polypeptide, and nature of the solvent. Typically, the temperature at which the polypeptide is used ranges from about 4° C. to about 65° C. Usually the temperature at use is greater than about 18° C. and more usually greater than about 22° C. For diagnostic purposes, the temperature will usually be about room temperature or warmer, but less than the denaturation temperature of components in the assay. For therapeutic purposes, the temperature will usually be body temperature, typically about 37° C. for humans, though under certain situations the temperature may be raised or lowered in situ or in vitro.

The electrolytes will usually approximate in situ physiological conditions, but may be modified to higher or lower ionic strength where advantageous. The actual ions may be modified, e.g., to conform to standard buffers used in physiological or analytical contexts.

The size and structure of the polypeptide should generally be in a substantially stable state, and usually not in a denatured state. The polypeptide may be associated with other polypeptides in a quaternary structure, e.g., to confer solubility, or associated with lipids or detergents in a manner which approximates natural lipid bilayer interactions.

The solvent will usually be a biologically compatible buffer, of a type used for preservation of biological activities, and will usually approximate a physiological solvent. Usually the solvent will have a neutral pH, typically between about 5 and 10, and preferably about 7.5. On some occasions, a detergent will be added, typically a mild non-denaturing one, e.g., CHS or CHAPS, or a low enough concentration as to avoid significant disruption of structural or physiological properties of the antigen.

Solubility is reflected by sedimentation measured in Svedberg units, which are a measure of the sedimentation velocity of a molecule under particular conditions. The determination of the sedimentation velocity was classically performed in an analytical ultracentrifuge, but is typically now performed in a standard ultracentrifuge. See, Freifelder (1982) *Physical Biochemistry* (2d ed.), W.H. Freeman; and Cantor and Schimmel (1980) *Biophysical Chemistry*, parts 1-3, W.H. Freeman & Co., San Francisco. As a crude determination, a sample containing a putatively soluble polypeptide is spun in a standard full sized ultracentrifuge at about 50K rpm for about 10 minutes, and soluble molecules will remain in the supernatant. A soluble particle or polypeptide will typically be less than about 30S, more typically less than about 15S, usually less than about 10S, more usually less than about 6S, and, in particular embodiments, preferably less than about 4S, and more preferably less than about 3S.

IV. Making IL-170 Protein; Mimetics

DNA which encodes the IL-170 protein or fragments thereof can be obtained by chemical synthesis, screening cDNA libraries, or by screening genomic libraries prepared from a wide variety of cell lines or tissue samples.

This DNA can be expressed in a wide variety of host cells for the synthesis of a full-length protein or fragments which can in turn, for example, be used to generate polyclonal or monoclonal antibodies; for binding studies; for construction and expression of modified molecules; and for structure/function studies. Each antigen or its fragments can be expressed in host cells that are transformed or transfected with appropriate expression vectors. These molecules can be substantially purified to be free of protein or cellular contaminants, other than those derived from the recombinant host, and therefore are particularly useful in pharmaceutical compositions when combined with a pharmaceutically acceptable carrier and/or diluent. The antigen, or portions thereof, may be expressed as fusions with other proteins.

Expression vectors are typically self-replicating DNA or RNA constructs containing the desired antigen gene or its fragments, usually operably linked to suitable genetic control elements that are recognized in a suitable host cell. These control elements are capable of effecting expression within a suitable host. The specific type of control elements necessary to effect expression will depend upon the eventual host cell used. Generally, the genetic control elements can include a prokaryotic promoter system or a eukaryotic promoter expression control system, and typically include a transcriptional promoter, an optional operator to control the onset of transcription, transcription enhancers to elevate the level of mRNA expression, a sequence that encodes a suitable ribosome binding site, and sequences that terminate transcription and translation. Expression vectors also usually contain an origin of replication that allows the vector to replicate independently of the host cell. Methods for amplifying vector copy number are also known, see, e.g., Kaufman, et al. (1985) *Molec. and Cell. Biol.* 5:1750-1759.

The vectors of this invention contain DNA which encodes an IL-170 protein, or a fragment thereof, typically encoding a biologically active polypeptide. The DNA can be under the control of a viral promoter and can encode a selection marker. This invention further contemplates use of such expression vectors which are capable of expressing eukaryotic cDNA coding for an IL-170 protein in a prokaryotic or eukaryotic host, where the vector is compatible with the host and where the eukaryotic cDNA coding for the antigen is inserted into the vector such that growth of the host containing the vector expresses the cDNA in question. Usually, expression vectors are designed for stable replication in their host cells or for amplification to greatly increase the total number of copies of the desirable gene per cell. It is not always necessary to require that an expression vector replicate in a host cell, e.g., it is possible to effect transient expression of the antigen or its fragments in various hosts using vectors that do not contain a replication origin that is recognized by the host cell. It is also possible to use vectors that cause integration of an IL-170 protein gene or its fragments into the host DNA by recombination, or to integrate a promoter which controls expression of an endogenous gene.

Vectors, as used herein, comprise plasmids, viruses, bacteriophage, integratable DNA fragments, and other vehicles which enable the integration of DNA fragments into the genome of the host. Expression vectors are specialized vectors which contain genetic control elements that effect expression of operably linked genes. Plasmids are the most commonly used form of vector but all other forms of vectors which serve an equivalent function and which are, or become, known in the art are suitable for use herein. See, e.g., Pouwels, et al. (1985 and Supplements) *Cloning Vectors: A Laboratory Manual*, Elsevier, N.Y., and Rodriquez, et al. (eds. 1988) *Vectors: A Survey of Molecular Cloning Vectors and Their Uses*, Buttersworth, Boston, Mass.

Transformed cells include cells, preferably mammalian, that have been transformed or transfected with vectors containing an IL-170 gene, typically constructed using recombinant DNA techniques. Transformed host cells usually express the antigen or its fragments, but for purposes of cloning, amplifying, and manipulating its DNA, do not need to express the protein. This invention further contemplates culturing transformed cells in a nutrient medium, thus permitting the protein to accumulate in the culture. The protein can be recovered, either from the culture or from the culture medium.

For purposes of this invention, DNA sequences are operably linked when they are functionally related to each other. For example, DNA for a presequence or secretory leader is operably linked to a polypeptide if it is expressed as a preprotein or participates in directing the polypeptide to the cell membrane or in secretion of the polypeptide. A promoter is operably linked to a coding sequence if it controls the transcription of the polypeptide; a ribosome binding site is operably linked to a coding sequence if it is positioned to permit translation. Usually, operably linked means contiguous and in reading frame, however, certain genetic elements such as repressor genes are not contiguously linked but still bind to operator sequences that in turn control expression.

Suitable host cells include prokaryotes, lower eukaryotes, and higher eukaryotes. Prokaryotes include both gram negative and gram positive organisms, e.g., *E. coli* and *B. subtilis*. Lower eukaryotes include yeasts, e.g., *S. cerevisiae* and *Pichia*, and species of the genus Dictyostelium. Higher eukaryotes include established tissue culture cell lines from animal cells, both of non-mammalian origin, e.g., insect cells, and birds, and of mammalian origin, e.g., human, primates, and rodents.

Prokaryotic host-vector systems include a wide variety of vectors for many different species. As used herein, *E. coli* and its vectors will be used generically to include equivalent vectors used in other prokaryotes. A representative vector for amplifying DNA is pBR322 or many of its derivatives. Vectors that can be used to express the IL-170 proteins or its fragments include, but are not limited to, such vectors as those containing the lac promoter (pUC-series); trp promoter (pBR322-trp); Ipp promoter (the pIN-series); lambda-pP or pR promoters (pOTS); or hybrid promoters such as ptac (pDR540). See Brosius, et al. (1988) "Expression Vectors Employing Lambda-, trp-, lac-, and Ipp-derived Promoters", in Rodriguez and Denhardt (eds.) *Vectors: A Survey of Molecular Cloning Vectors and Their Uses*, Buttersworth, Boston, Chapter 10, pp. 205-236.

Lower eukaryotes, e.g., yeasts and Dictyostelium, may be transformed with vectors encoding IL-170 proteins. For purposes of this invention, the most common lower eukaryotic host is the baker's yeast, *Saccharomyces cerevisiae*. It will be used to generically represent lower eukaryotes although a number of other strains and species are also available. Yeast vectors typically consist of a replication origin (unless of the integrating type), a selection gene, a promoter, DNA encoding the desired protein or its fragments, and sequences for translation termination, polyadenylation, and transcription termination. Suitable expression vectors for yeast include such constitutive promoters as 3-phosphoglycerate kinase and various other glycolytic enzyme gene promoters or such inducible promoters as the alcohol dehydrogenase 2 promoter or metallothionine promoter. Suitable vectors include derivatives of the following types: self-replicating low copy number (such as the YRp-series), self-replicating high copy number (such as the YEp-series); integrating types (such as the YIp-series), or mini-chromosomes (such as the YCp-series).

Higher eukaryotic tissue culture cells are the preferred host cells for expression of the functionally active IL-170 protein. In principle, many higher eukaryotic tissue culture cell lines are workable, e.g., insect baculovirus expression systems, whether from an invertebrate or vertebrate source. However, mammalian cells are preferred, in that the processing, both cotranslationally and posttranslationally. Transformation or transfection and propagation of such cells has become a routine procedure. Examples of useful cell lines include HeLa cells, Chinese hamster ovary (CHO) cell lines, baby rat kidney (BRK) cell lines, insect cell lines, bird cell lines, and monkey (COS) cell lines. Expression vectors for such cell lines usually include an origin of replication, a promoter, a translation initiation site, RNA splice sites (if genomic DNA is used), a polyadenylation site, and a transcription termination site. These vectors also usually contain a selection gene or amplification gene. Suitable expression vectors may be plasmids, viruses, or retroviruses carrying promoters derived, e.g., from such sources as from adenovirus, SV40, parvoviruses, vaccinia virus, or cytomegalovirus. Representative examples of suitable expression vectors include pcDNA1; pCD, see Okayama, et al. (1985) *Mol. Cell Biol.* 5:1136-1142; pMC1neo Poly-A, see Thomas, et al. (1987) *Cell* 51:503-512; and a baculovirus vector such as pAC 373 or pAC 610, see O'Reilly, et al. (1992) *Baculovirus Expression Vectors: A Laboratory Manual* Freeman and Co., CRC Press, Boca Raton, Fla.

It will often be desired to express an IL-170 protein polypeptide in a system which provides a specific or defined glycosylation pattern. In this case, the usual pattern will be that provided naturally by the expression system. However, the pattern will be modifiable by exposing the polypeptide, e.g., an unglycosylated form, to appropriate glycosylating proteins introduced into a heterologous expression system. For example, the IL-170 protein gene may be co-transformed with one or more genes encoding mammalian or other glycosylating enzymes. Using this approach, certain mammalian glycosylation patterns will be achievable or approximated in prokaryote or other cells.

The IL-170 protein, or a fragment thereof, may be engineered to be phosphatidyl inositol (PI) linked to a cell membrane, but can be removed from membranes by treatment with a phosphatidyl inositol cleaving enzyme, e.g., phosphatidyl inositol phospholipase-C. This releases the antigen in a biologically active form, and allows purification by standard procedures of protein chemistry. See, e.g., Low (1989) *Biochim. Biophys. Acta* 988:427-454; Tse, et al. (1985) *Science* 230:1003-1008; and Brunner, et al. (1991) *J. Cell Biol.* 114:1275-1283.

Now that the IL-170 protein has been characterized, fragments or derivatives thereof can be prepared by conventional processes for synthesizing peptides. These include processes such as are described in Stewart and Young (1984) *Solid Phase Peptide Synthesis*, Pierce Chemical Co., Rockford, Ill.; Bodanszky and Bodanszky (1984) *The Practice of Peptide Synthesis*, Springer-Verlag, New York; and Bodanszky (1984) *The Principles of Peptide Synthesis*, Springer-Verlag, New York. For example, an azide process, an acid chloride process, an acid anhydride process, a mixed anhydride process, an active ester process (for example, p-nitrophenyl ester, N-hydroxysuccinimide ester, or cyanomethyl ester), a carbodiimidazole process, an oxidative-reductive process, or a dicyclohexylcarbodiimide (DCCD)/additive process can be used. Solid phase and solution phase syntheses are both applicable to the foregoing processes.

The IL-170 protein, fragments, or derivatives are suitably prepared in accordance with the above processes as typically employed in peptide synthesis, generally either by a so-called stepwise process which comprises condensing an amino acid to the terminal amino acid, one by one in sequence, or by coupling peptide fragments to the terminal amino acid. Amino groups that are not being used in the coupling reaction are typically protected to prevent coupling at an incorrect location.

If a solid phase synthesis is adopted, the C-terminal amino acid is bound to an insoluble carrier or support through its carboxyl group. The insoluble carrier is not particularly limited as long as it has a binding capability to a reactive carboxyl group. Examples of such insoluble carriers include halomethyl resins, such as chloromethyl resin or bromomethyl resin, hydroxymethyl resins, phenol resins, tert-alkyloxycarbonyl-hydrazidated resins, and the like.

An amino group-protected amino acid is bound in sequence through condensation of its activated carboxyl group and the reactive amino group of the previously formed peptide or chain, to synthesize the peptide step by step. After synthesizing the complete sequence, the peptide is split off from the insoluble carrier to produce the peptide. This solid-phase approach is generally described by Merrifield, et al. (1963) in *J. Am. Chem. Soc.* 85:2149-2156.

The prepared protein and fragments thereof can be isolated and purified from the reaction mixture by means of peptide separation, for example, by extraction, precipitation, electrophoresis and various forms of chromatography, and the like. The IL-170 proteins of this invention can be obtained in varying degrees of purity depending upon its desired use. Purification can be accomplished by use of the protein purification techniques disclosed herein or by the use of the antibodies herein described in immunoabsorbant affinity chromatography. This immunoabsorbant affinity chromatography is carried out by first linking the antibodies to a solid support and then contacting the linked antibodies with solubilized lysates of appropriate source cells, lysates of other cells expressing the protein, or lysates or supernatants of cells producing the IL-170 protein as a result of DNA techniques, see below.

V. Physical Variants

This invention also encompasses proteins or peptides having substantial amino acid sequence homology with the amino acid sequence of the IL-170 protein. The variants include species or allelic variants.

Amino acid sequence homology, or sequence identity, is determined by optimizing residue matches, if necessary, by introducing gaps as required. This changes when considering conservative substitutions as matches. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. Homologous amino acid sequences are typically intended to include natural allelic and interspecies variations in each respective protein sequence. Typical homologous proteins or peptides will have from 25-100% homology (if gaps can be introduced), to 50-100% homology (if conservative substitutions are included) with the amino acid sequence of the IL-170 protein. Homology measures will be at least about 35%, generally at least 40%, more generally at least 45%, often at least 50%, more often at least 55%, typically at least 60%, more typically at least 65%, usually at least 70%, more usually at least 75%, preferably at least 80%, and more preferably at least 80%, and in particularly preferred embodiments, at least 85% or more. See also Needleham, et al. (1970) *J. Mol. Biol.* 48:443-453; Sankoff, et al. (1983) Chapter One in *Time Warps, String Edits, and Macromolecules: The Theory and Practice of Sequence Comparison* Addison-Wesley, Reading, Mass.; and software packages from IntelliGenetics, Mountain View, Calif.; and the University of Wisconsin Genetics Computer Group, Madison, Wis.

The isolated DNA encoding an IL-170 protein can be readily modified by nucleotide substitutions, nucleotide deletions, nucleotide insertions, and inversions of nucleotide stretches. These modifications result in novel DNA sequences which encode these antigens, their derivatives, or proteins having similar physiological, immunogenic, or antigenic activity. These modified sequences can be used to produce mutant antigens or to enhance expression. Enhanced expression may involve gene amplification, increased transcription, increased translation, and other mechanisms. Such mutant IL-170 protein derivatives include predetermined or site-specific mutations of the respective protein or its fragments. "Mutant IL-170 protein" encompasses a polypeptide otherwise falling within the homology definition of the murine IL-170 or human IL-170 protein as set forth above, but having an amino acid sequence which differs from that of IL-170 protein as found in nature, whether by way of deletion, substitution, or insertion. In particular, "site specific mutant IL-170 protein" generally includes proteins having significant homology with the corresponding protein having sequences from Tables 1-6, and as sharing various biological activities, e.g., antigenic or immunogenic, with those sequences, and in preferred embodiments contain most of the disclosed sequences. Similar concepts apply to different IL-170 proteins, particularly those found in various warm blooded animals, e.g., mammals and birds. As stated before, it is emphasized that descriptions are generally meant to encompass all IL-170 proteins, not limited to the mouse embodiment specifically discussed.

Although site specific mutation sites are predetermined, mutants need not be site specific. IL-170 protein mutagenesis can be conducted by making amino acid insertions or deletions. Substitutions, deletions, insertions, or any combinations may be generated to arrive at a final construct. Insertions include amino- or carboxy-terminal fusions. Random mutagenesis can be conducted at a target codon and the expressed mutants can then be screened for the desired activity. Methods for making substitution mutations at predetermined sites in DNA having a known sequence are well known in the art, e.g., by M13 primer mutagenesis or polymerase chain reaction (PCR) techniques. See also Sambrook, et al. (1989) and Ausubel, et al. (1987 and Supplements).

The mutations in the DNA normally should not place coding sequences out of reading frames and preferably will not create complementary regions that could hybridize to produce secondary mRNA structure such as loops or hairpins.

The present invention also provides recombinant proteins, e.g., heterologous fusion proteins using segments from these proteins. A heterologous fusion protein is a fusion of proteins or segments which are naturally not normally fused in the same manner. Thus, the fusion product of an immunoglobulin with an IL-170 polypeptide is a continuous protein molecule having sequences fused in a typical peptide linkage, typically made as a single translation product and exhibiting properties derived from each source peptide. A similar concept applies to heterologous nucleic acid sequences.

In addition, new constructs may be made from combining similar functional domains from other proteins. For example, antigen-binding or other segments may be "swapped" between different new fusion polypeptides or fragments. See, e.g., Cunningham, et al. (1989) *Science* 243:1330-1336; and O'Dowd, et al. (1988) *J. Biol. Chem.* 263:15985-15992. Thus, new chimeric polypeptides exhibiting new combinations of specificities will result from the functional linkage of biologically relevant domains and other functional domains.

The phosphoramidite method described by Beaucage and Carruthers (1981) *Tetra. Letts.* 22:1859-1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence, e.g., PCR techniques.

VI. Functional Variants

The blocking of physiological response to IL-170 proteins may result from the inhibition of binding of the antigen to its natural binding partner, e.g., through competitive inhibition. Thus, in vitro assays of the present invention will often use isolated protein, membranes from cells expressing a recombinant membrane associated IL-170 protein, soluble fragments comprising binding segments, or fragments attached to solid phase substrates. These assays will also allow for the diagnostic determination of the effects of either binding segment mutations and modifications, or protein mutations and modifications, e.g., analogs.

This invention also contemplates the use of competitive drug screening assays, e.g., where neutralizing antibodies to antigen or binding partner fragments compete with a test compound for binding to the protein. In this manner, the antibodies can be used to detect the presence of any polypeptide which shares one or more antigenic binding sites of the protein and can also be used to occupy binding sites on the protein that might otherwise interact with a binding partner.

Additionally, neutralizing antibodies against the IL-170 protein and soluble fragments of the antigen which contain a high affinity receptor binding site, can be used to inhibit antigen function in tissues, e.g., tissues experiencing abnormal physiology.

"Derivatives" of the IL-170 antigens include amino acid sequence mutants, glycosylation variants, and covalent or aggregate conjugates with other chemical moieties. Covalent derivatives can be prepared by linkage of functionalities to groups which are found in the IL-170 amino acid side chains or at the N- or C-termini, by means which are well known in the art. These derivatives can include, without limitation, aliphatic esters or amides of the carboxyl terminus, or of residues containing carboxyl side chains, O-acyl derivatives of hydroxyl group-containing residues, and N-acyl derivatives of the amino terminal amino acid or amino-group containing residues, e.g., lysine or arginine. Acyl groups are selected from the group of alkyl-moieties including C3 to C18 normal alkyl, thereby forming alkanoyl aroyl species. Covalent attachment to carrier proteins may be important when immunogenic moieties are haptens.

In particular, glycosylation alterations are included, e.g., made by modifying the glycosylation patterns of a polypeptide during its synthesis and processing, or in further processing steps. Particularly preferred means for accomplishing this are by exposing the polypeptide to glycosylating enzymes derived from cells which normally provide such processing, e.g., mammalian glycosylation enzymes. Deglycosylation enzymes are also contemplated. Also embraced are versions of the same primary amino acid sequence which have other minor modifications, including phosphorylated amino acid residues, e.g., phosphotyrosine, phosphoserine, or phosphothreonine.

A major group of derivatives are covalent conjugates of the IL-170 protein or fragments thereof with other proteins or polypeptides. These derivatives can be synthesized in recombinant culture such as N- or C-terminal fusions or by the use of agents known in the art for their usefulness in cross-linking proteins through reactive side groups. Preferred antigen derivatization sites with cross-linking agents are at free amino groups, carbohydrate moieties, and cysteine residues.

Fusion polypeptides between the IL-170 proteins and other homologous or heterologous proteins are also provided. Homologous polypeptides may be fusions between different surface markers, resulting in, e.g., a hybrid protein exhibiting receptor binding specificity. Likewise, heterologous fusions may be constructed which would exhibit a combination of properties or activities of the derivative proteins. Typical examples are fusions of a reporter polypeptide, e.g., luciferase, with a segment or domain of an antigen, e.g., a receptor-binding segment, so that the presence or location of the fused antigen may be easily determined. See, e.g., Dull, et al., U.S. Pat. No. 4,859,609. Other gene fusion partners include bacterial β-galactosidase, trpE, Protein A, β-lactamase, alpha amylase, alcohol dehydrogenase, and yeast alpha mating factor. See, e.g., Godowski, et al. (1988) *Science* 241:812-816.

The phosphoramidite method described by Beaucage and Carruthers (1981) *Tetra. Letts.* 22:1859-1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence.

Such polypeptides may also have amino acid residues which have been chemically modified by phosphorylation, sulfonation, biotinylation, or the addition or removal of other moieties, particularly those which have molecular shapes similar to phosphate groups. In some embodiments, the modifications will be useful labeling reagents, or serve as purification targets, e.g., affinity ligands.

Fusion proteins will typically be made by either recombinant nucleic acid methods or by synthetic polypeptide methods. Techniques for nucleic acid manipulation and expression are described generally, for example, in Sambrook, et al. (1989) *Molecular Cloning: A Laboratory Manual* (2d ed.), Vols. 1-3, Cold Spring Harbor Laboratory. Techniques for synthesis of polypeptides are described, for example, in Merrifield (1963) *J. Amer. Chem. Soc.* 85:2149-2156; Merrifield (1986) *Science* 232: 341-347; and Atherton, et al. (1989) *Solid Phase Peptide Synthesis: A Practical Approach*, IRL Press, Oxford.

This invention also contemplates the use of derivatives of the IL-170 proteins other than variations in amino acid sequence or glycosylation. Such derivatives may involve covalent or aggregative association with chemical moieties. These derivatives generally fall into the three classes: (1)

salts, (2) side chain and terminal residue covalent modifications, and (3) adsorption complexes, for example with cell membranes. Such covalent or aggregative derivatives are useful as immunogens, as reagents in immunoassays, or in purification methods such as for affinity purification of antigens or other binding proteins. For example, an IL-170 antigen can be immobilized by covalent bonding to a solid support such as cyanogen bromide-activated Sepharose, by methods which are well known in the art, or adsorbed onto polyolefin surfaces, with or without glutaraldehyde cross-linking, for use in the assay or purification of anti-IL-170 protein antibodies or its receptor or other binding partner. The IL-170 antigens can also be labeled with a detectable group, for example radioiodinated by the chloramine T procedure, covalently bound to rare earth chelates, or conjugated to another fluorescent moiety for use in diagnostic assays. Purification of IL-170 protein may be effected by immobilized antibodies or binding partners.

A solubilized IL-170 antigen or fragment of this invention can be used as an immunogen for the production of antisera or antibodies specific for the protein or fragments thereof. The purified antigen can be used to screen monoclonal antibodies or binding fragments prepared by immunization with various forms of impure preparations containing the protein. In particular, the term "antibodies" also encompasses antigen binding fragments of natural antibodies. The purified IL-170 proteins can also be used as a reagent to detect any antibodies generated in response to the presence of elevated levels of the protein or cell fragments containing the antigen, both of which may be diagnostic of an abnormal or specific physiological or disease condition. Additionally, antigen fragments may also serve as immunogens to produce the antibodies of the present invention, as described immediately below. For example, this invention contemplates antibodies raised against amino acid sequences encoded by nucleotide sequences shown in Tables 1-6, or fragments of proteins containing them. In particular, this invention contemplates antibodies having binding affinity to or being raised against specific fragments which are predicted to lie outside of the lipid bilayer.

The present invention contemplates the isolation of additional closely related species variants. Southern blot analysis established that similar genetic entities exist in other mammals, e.g., rat and human. It is likely that the IL-170 proteins are widespread in species variants, e.g., rodents, lagomorphs, carnivores, artiodactyla, perissodactyla, and primates.

The invention also provides means to isolate a group of related antigens displaying both distinctness and similarities in structure, expression, and function. Elucidation of many of the physiological effects of the antigens will be greatly accelerated by the isolation and characterization of distinct species variants. In particular, the present invention provides useful probes for identifying additional homologous genetic entities in different species.

The isolated genes will allow transformation of cells lacking expression of a corresponding IL-170 protein, e.g., either species types or cells which lack corresponding antigens and should exhibit negative background activity. Expression of transformed genes will allow isolation of antigenically pure cell lines, with defined or single specie variants. This approach will allow for more sensitive detection and discrimination of the physiological effects of IL-170 proteins. Subcellular fragments, e.g., cytoplasts or membrane fragments, can be isolated and used.

Dissection of the critical structural elements which effect the various physiological or differentiation functions provided by the proteins is possible using standard techniques of modern molecular biology, particularly in comparing members of the related class. See, e.g., the homolog-scanning mutagenesis technique described in Cunningham, et al. (1989) *Science* 243:1339-1336; and approaches used in O'Dowd, et al. (1988) *J. Biol. Chem.* 263:15985-15992; and Lechleiter, et al. (1990) *EMBO J.* 9:4381-4390.

In particular, functional domains or segments can be substituted between species variants to determine what structural features are important in both binding partner affinity and specificity, as well as signal transduction. An array of different variants will be used to screen for molecules exhibiting combined properties of interaction with different species variants of binding partners.

Antigen internalization may occur under certain circumstances, and interaction between intracellular components and "extracellular" segments of proteins involved in interactions may occur. The specific segments of interaction of IL-170 protein with other intracellular components may be identified by mutagenesis or direct biochemical means, e.g., cross-linking or affinity methods. Structural analysis by crystallographic or other physical methods will also be applicable. Further investigation of the mechanism of biological function will include study of associated components which may be isolatable by affinity methods or by genetic means, e.g., complementation analysis of mutants.

Further study of the expression and control of IL-170 protein will be pursued. The controlling elements associated with the antigens may exhibit differential developmental, tissue specific, or other expression patterns. Upstream or downstream genetic regions, e.g., control elements, are of interest.

Structural studies of the antigen will lead to design of new variants, particularly analogs exhibiting agonist or antagonist properties on binding partners. This can be combined with previously described screening methods to isolate variants exhibiting desired spectra of activities.

Expression in other cell types will often result in glycosylation differences in a particular antigen. Various species variants may exhibit distinct functions based upon structural differences other than amino acid sequence. Differential modifications may be responsible for differential function, and elucidation of the effects are now made possible.

Thus, the present invention provides important reagents related to antigen-binding partner interaction. Although the foregoing description has focused primarily upon the murine IL-170 and human IL-170 protein, those of skill in the art will immediately recognize that the invention encompasses other antigens, e.g., mouse and other mammalian species or allelic variants, as well as variants thereof.

VII. Antibodies

Antibodies can be raised to the various IL-170 proteins, including species or allelic variants, and fragments thereof, both in their naturally occurring forms and in their recombinant forms. Additionally, antibodies can be raised to IL-170 proteins in either their active forms or in their inactive forms. Anti-idiotypic antibodies are also contemplated.

Antibodies, including binding fragments and single chain versions, against predetermined fragments of the antigens can be raised by immunization of animals with conjugates of the fragments with immunogenic proteins. Monoclonal antibodies are prepared from cells secreting the desired antibody. These antibodies can be screened for binding to normal or defective IL-170 proteins, or screened for agonistic or antagonistic activity, e.g., mediated through a binding partner. These monoclonal antibodies will usually bind with at least a $K_D$ of about 1 mM, more usually at least about 300 μM, typically at least about 10 µM, more typically at least about 30 µM, preferably at least about 10 µM, and more preferably at least about 3 µM or better.

An IL-170 polypeptide that specifically binds to or that is specifically immunoreactive with an antibody, e.g., such as a polyclonal antibody, generated against a defined immunogen, e.g., such as an immunogen consisting of an amino acid sequence of mature SEQ ID NO: 8 or fragments thereof or a polypeptide generated from the nucleic acid of SEQ ID NO: 7 is typically determined in an immunoassay. Included within the metes and bounds of the present invention are those nucleic acid sequences described herein, including functional variants, that encode polypeptides that selectively bind to polyclonal antibodies generated against the prototypical IL-173, IL-174, IL-176, or IL-177 polypeptide as structurally and functionally defined herein. The immunoassay typically uses a polyclonal antiserum which was raised, e.g., to a protein of SEQ ID NO: 8. This antiserum is selected to have low crossreactivity against appropriate other IL-170 family members, preferably from the same species, and any such crossreactivity is removed by immunoabsorption prior to use in the immunoassay. Appropriate selective serum preparations can be isolated, and characterized.

In order to produce antisera for use in an immunoassay, the protein, e.g., of SEQ ID NO: 8, is isolated as described herein. For example, recombinant protein may be produced in a mammalian cell line. An appropriate host, e.g., an inbred strain of mice such as Balb/c, is immunized with the protein of SEQ ID NO: 8 using a standard adjuvant, such as Freund's adjuvant, and a standard mouse immunization protocol (see Harlow and Lane). Alternatively, a substantially full length synthetic peptide derived from the sequences disclosed herein can be used as an immunogen. Polyclonal sera are collected and titered against the immunogen protein in an immunoassay, e.g., a solid phase immunoassay with the immunogen immobilized on a solid support. Polyclonal antisera with a titer of $10^4$ or greater are selected and tested for their cross reactivity against other IL-170 family members, e.g., IL-171, IL-172, or IL-175, using a competitive binding immunoassay such as the one described in Harlow and Lane, supra, at pages 570-573. Preferably at least two IL-170 family members are used in this determination in conjunction with the target. These IL-170 family members can be produced as recombinant proteins and isolated using standard molecular biology and protein chemistry techniques as described herein. Thus, antibody preparations can be identified or produced having desired selectivity or specificity for subsets of IL-170 family members.

Immunoassays in the competitive binding format can be used for the crossreactivity determinations. For example, the protein of mature SEQ ID NO: 8 can be immobilized to a solid support. Proteins added to the assay compete with the binding of the antisera to the immobilized antigen. The ability of the above proteins to compete with the binding of the antisera to the immobilized protein is compared to the protein of SEQ ID NO: 8. The percent crossreactivity for the above proteins is calculated, using standard calculations. Those antisera with less than 10% crossreactivity with each of the proteins listed above are selected and pooled. The cross-reacting antibodies are then removed from the pooled antisera by immunoabsorption with the above-listed proteins.

The immunoabsorbed and pooled antisera are then used in a competitive binding immunoassay as described above to compare a second protein to the immunogen protein. In order to make this comparison, the two proteins are each assayed at a wide range of concentrations and the amount of each protein required to inhibit 50% of the binding of the antisera to the immobilized protein is determined. If the amount of the second protein required is less than twice the amount of the protein of, e.g., SEQ ID NO: 8 that is required, then the second protein is said to specifically bind to an antibody generated to the immunogen.

The antibodies, including antigen binding fragments, of this invention can have significant diagnostic or therapeutic value. They can be potent antagonists that bind to a binding partner and inhibit antigen binding or inhibit the ability of an antigen to elicit a biological response. They also can be useful as non-neutralizing antibodies and can be coupled to toxins or radionuclides so that when the antibody binds to the antigen, a cell expressing it, e.g., on its surface, is killed. Further, these antibodies can be conjugated to drugs or other therapeutic agents, either directly or indirectly by means of a linker, and may effect drug targeting.

The antibodies of this invention can also be useful in diagnostic applications. As capture or non-neutralizing antibodies, they can be screened for ability to bind to the antigens without inhibiting binding by a partner. As neutralizing antibodies, they can be useful in competitive binding assays. They will also be useful in detecting or quantifying IL-170 protein or its binding partners. See, e.g., Chan (ed. 1987) *Immunoassay: A Practical Guide* Academic Press, Orlando, Fla.; Ngo (ed. 1988) Nonisotopic Immunoassay Plenum Press, NY; and Price and Newman (eds. 1991) *Principles and Practice of Immunoassay* Stockton Press, NY.

Antigen fragments may be joined to other materials, particularly polypeptides, as fused or covalently joined polypeptides to be used as immunogens. An antigen and its fragments may be fused or covalently linked to a variety of immunogens, such as keyhole limpet hemocyanin, bovine serum albumin, tetanus toxoid, etc. See *Microbiology*, Hoeber Medical Division, Harper and Row, 1969; Landsteiner (1962) *Specificity of Serological Reactions*, Dover Publications, New York, and Williams, et al. (1967) *Methods in Immunology and Immunochemistry*, Vol. 1, Academic Press, New York, for descriptions of methods of preparing polyclonal antisera. A typical method involves hyperimmunization of an animal with an antigen. The blood of the animal is then collected shortly after the repeated immunizations and the gamma globulin is isolated.

In some instances, it is desirable to prepare monoclonal antibodies from various mammalian hosts, such as mice, rodents, primates, humans, etc. Description of techniques for preparing such monoclonal antibodies may be found in, e.g., Stites, et al. (eds.) *Basic and Clinical Immunology* (4th ed.), Lange Medical Publications, Los Altos, Calif., and references cited therein; Harlow and Lane (1988) *Antibodies: A Laboratory Manual*, CSH Press; Goding (1986) *Monoclonal Antibodies: Principles and Practice* (2d ed.) Academic Press, New York; and particularly in Kohler and Milstein (1975) in *Nature* 256: 495-497, which discusses one method of generating monoclonal antibodies. Summarized briefly, this method involves injecting an animal with an immunogen. The animal is then sacrificed and cells taken from its spleen, which are then fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Other suitable techniques involve in vitro exposure of lymphocytes to the antigenic polypeptides or alternatively to selection of libraries of antibodies in phage or similar vectors. See, Huse, et al. (1989) "Generation of a Large Combinatorial Library of the Immunoglobulin Repertoire in Phage Lambda," *Science* 246:1275-1281; and Ward, et al. (1989) *Nature* 341:544-546. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents, teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced, see Cabilly, U.S. Pat. No. 4,816,567.

The antibodies of this invention can also be used for affinity chromatography in isolating the protein. Columns can be prepared where the antibodies are linked to a solid support, e.g., particles, such as agarose, Sephadex, or the like, where a cell lysate may be passed through the column, the column washed, followed by increasing concentrations of a mild denaturant, whereby the purified IL-170 protein will be released.

The antibodies may also be used to screen expression libraries for particular expression products. Usually the antibodies used in such a procedure will be labeled with a moiety allowing easy detection of presence of antigen by antibody binding.

Antibodies raised against each IL-170 protein will also be useful to raise anti-idiotypic antibodies. These will be useful in detecting or diagnosing various immunological conditions related to expression of the respective antigens.

VIII. Uses

The present invention provides reagents which will find use in diagnostic applications as described elsewhere herein, e.g., in the general description for physiological or developmental abnormalities, or below in the description of kits for diagnosis.

This invention also provides reagents with significant therapeutic value. The IL-170 protein (naturally occurring or recombinant), fragments thereof, and antibodies thereto, along with compounds identified as having binding affinity to IL-170 protein, should be useful in the treatment of conditions associated with abnormal physiology or development, including abnormal proliferation, e.g., cancerous conditions, or degenerative conditions. Abnormal proliferation, regeneration, degeneration, and atrophy may be modulated by appropriate therapeutic treatment using the compositions provided herein. For example, a disease or disorder associated with abnormal expression or abnormal signaling by an IL-170 antigen should be a likely target for an agonist or antagonist of the protein.

Other abnormal developmental conditions are known in the cell types shown to possess IL-170 antigen mRNA by Northern blot analysis. See Berkow (ed.) *The Merck Manual of Diagnosis and Therapy*, Merck & Co., Rahway, N.J.; and Thorn, et al. *Harrison's Principles of Internal Medicine*, McGraw-Hill, N.Y. These problems may be susceptible to prevention or treatment using compositions provided herein.

Recombinant antibodies which bind to IL-170 can be purified and then administered to a patient. These reagents can be combined for therapeutic use with additional active or inert ingredients, e.g., in conventional pharmaceutically acceptable carriers or diluents, e.g., immunogenic adjuvants, along with physiologically innocuous stabilizers and excipients. These combinations can be sterile filtered and placed into dosage forms as by lyophilization in dosage vials or storage in stabilized aqueous preparations. This invention also contemplates use of antibodies or binding fragments thereof, including forms which are not complement binding.

Screening using IL-170 for binding partners or compounds having binding affinity to IL-170 antigen can be performed, including isolation of associated components. Subsequent biological assays can then be utilized to determine if the compound has intrinsic biological activity and is therefore an agonist or antagonist in that it blocks an activity of the antigen. This invention further contemplates the therapeutic use of antibodies to IL-170 protein as antagonists. This approach should be particularly useful with other IL-170 protein species variants.

The quantities of reagents necessary for effective therapy will depend upon many different factors, including means of administration, target site, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman, et al. (eds. 1990) *Goodman and Gilman's: The Pharmacological Bases of Therapeutics,* 8th Ed., Pergamon Press; and *Remington's Pharmaceutical Sciences,* 17th ed. (1990), *Mack Publishing Co.,* Easton, Pa. Methods for administration are discussed therein and below, e.g., for oral, intravenous, intraperitoneal, or intramuscular administration, transdermal diffusion, and others. See also Langer (1990) *Science* 249: 1527-1533. Pharmaceutically acceptable carriers will include water, saline, buffers, and other compounds described, e.g., in the *Merck Index,* Merck & Co., Rahway, N.J. Dosage ranges would ordinarily be expected to be in amounts lower than 1 mM concentrations, typically less than about 10 μM concentrations, usually less than about 100 nM, preferably less than about 10 pM (picomolar), and most preferably less than about 1 fM (femtomolar), with an appropriate carrier. Slow release formulations, or a slow release apparatus will often be utilized for continuous administration.

IL-170 protein, fragments thereof, and antibodies to it or its fragments, antagonists, and agonists, may be administered directly to the host to be treated or, depending on the size of the compounds, it may be desirable to conjugate them to carrier proteins such as ovalbumin or serum albumin prior to their administration. Therapeutic formulations may be administered in any conventional dosage formulation. While it is possible for the active ingredient to be administered alone, it is preferable to present it as a pharmaceutical formulation. Formulations typically comprise at least one active ingredient, as defined above, together with one or more acceptable carriers thereof. Each carrier should be both pharmaceutically and physiologically acceptable in the sense of being compatible with the other ingredients and not injurious to the patient. Formulations include those suitable for oral, rectal, nasal, or parenteral (including subcutaneous, intramuscular, intravenous and intradermal) administration. The formulations may conveniently be presented in unit dosage form and may be prepared by any methods well known in the art of pharmacy. See, e.g., Gilman, et al. (eds. 1990) *Goodman and Gilman's: The Pharmacological Bases of Therapeutics,* 8th Ed., Pergamon Press, Parrytown, N.Y.; *Remington's Pharmaceutical Sciences,* 17th ed. (1990) Mack Publishing Co., Easton, Pa.; Avis, et al. (eds. 1993) *Pharmaceutical Dosage Forms: Parenteral Medications* 2d ed., Dekker, NY; Lieberman, et al. (eds. 1990) *Pharmaceutical Dosage Forms: Tablets* 2d ed., Dekker, NY; and Lieberman, et al. (eds. 1990) *Pharmaceutical Dosage Forms: Disperse Systems* Dekker, NY. The therapy of this invention may be combined with or used in association with other therapeutic, including cytokine, reagents.

Both the naturally occurring and the recombinant forms of the IL-170 proteins of this invention are particularly useful in kits and assay methods which are capable of screening compounds for binding activity to the proteins. Several methods of automating assays have been developed in recent years so as to permit screening of tens of thousands of compounds in a short period. See, e.g., Fodor, et al. (1991) *Science* 251:767-773, which describes means for testing of binding affinity by a plurality of defined polymers synthesized on a solid substrate. The development of suitable assays can be greatly facilitated by the availability of large amounts of purified, soluble IL-170 protein as provided by this invention.

This invention is particularly useful for screening compounds by using recombinant antigen in any of a variety of drug screening techniques. The advantages of using a recombinant protein in screening for specific ligands include: (a) improved renewable source of the antigen from a specific source; (b) potentially greater number of antigen molecules per cell giving better signal to noise ratio in assays; and (c) species variant specificity (theoretically giving greater biological and disease specificity). The purified protein may be tested in numerous assays, typically in vitro assays, which evaluate biologically relevant responses. See, e.g., Coligan *Current Protocols in Immunology*; Hood, et al. *Immunology* Benjamin/Cummings; Paul (ed.) *Fundamental Immunology*; and *Methods in Enzymology* Academic Press.

One method of drug screening utilizes eukaryotic or prokaryotic host cells which are stably transformed with recombinant DNA molecules expressing the IL-170 antigens. Cells may be isolated which express an antigen in isolation from other functionally equivalent antigens. Such cells, either in viable or fixed form, can be used for standard protein-protein binding assays. See also, Parce, et al. (1989) *Science* 246:243-247; and Owicki, et al. (1990) *Proc. Nat'l Acad. Sci. USA* 87:4007-4011, which describe sensitive methods to detect cellular responses. Competitive assays are particularly useful, where the cells (source of IL-170 protein) are contacted and incubated with a labeled binding partner or antibody having known binding affinity to the ligand, such as $^{125}$I-antibody, and a test sample whose binding affinity to the binding composition is being measured. The bound and free labeled binding compositions are then separated to assess the degree of antigen binding. The amount of test compound bound is inversely proportional to the amount of labeled receptor binding to the known source. Any one of numerous techniques can be used to separate bound from free antigen to assess the degree of binding. This separation step could typically involve a procedure such as adhesion to filters followed by washing, adhesion to plastic followed by washing, or centrifugation of the cell membranes. Viable cells could also be used to screen for the effects of drugs on IL-170 protein mediated functions, e.g., second messenger levels, i.e., $Ca^{++}$; cell proliferation; inositol phosphate pool changes; and others. Some detection methods allow for elimination of a separation step, e.g., a proximity sensitive detection system. Calcium sensitive dyes will be useful for detecting $Ca^{++}$ levels, with a fluorimeter or a fluorescence cell sorting apparatus.

Another method utilizes membranes from transformed eukaryotic or prokaryotic host cells as the source of the IL-170 protein. These cells are stably transformed with DNA vectors directing the expression of a membrane associated IL-170 protein, e.g., an engineered membrane bound form. Essentially, the membranes would be prepared from the cells and used in any receptor/ligand type binding assay such as the competitive assay set forth above.

Still another approach is to use solubilized, unpurified or solubilized, purified IL-170 protein from transformed eukaryotic or prokaryotic host cells. This allows for a "molecular" binding assay with the advantages of increased specificity, the ability to automate, and high drug test throughput.

Another technique for drug screening involves an approach which provides high throughput screening for compounds having suitable binding affinity to IL-170 and is described in detail in Geysen, European Patent Application 84/03564, published on Sep. 13, 1984. First, large numbers of different small peptide test compounds are synthesized on a solid substrate, e.g., plastic pins or some other appropriate surface, see Fodor, et al. (1991). Then all the pins are reacted with solubilized, unpurified or solubilized, purified IL-170 binding composition, and washed. The next step involves detecting bound binding composition.

Rational drug design may also be based upon structural studies of the molecular shapes of the IL-170 protein and other effectors or analogs. Effectors may be other proteins which mediate other functions in response to antigen binding, or other proteins which normally interact with the antigen. One means for determining which sites interact with specific other proteins is a physical structure determination, e.g., x-ray crystallography or 2 dimensional NMR techniques. These will provide guidance as to which amino acid residues form molecular contact regions. For a detailed description of protein structural determination, see, e.g., Blundell and Johnson (1976) *Protein Crystallography*, Academic Press, New York.

Purified IL-170 protein can be coated directly onto plates for use in the aforementioned drug screening techniques. However, non-neutralizing antibodies to these ligands can be used as capture antibodies to immobilize the respective ligand on the solid phase.

IX. Kits

This invention also contemplates use of IL-170 proteins, fragments thereof, peptides, and their fusion products in a variety of diagnostic kits and methods for detecting the presence of a binding composition. Typically the kit will have a compartment containing either a defined IL-170 peptide or gene segment or a reagent which recognizes one or the other, e.g., antigen fragments or antibodies.

A kit for determining the binding affinity of a test compound to an IL-170 protein would typically comprise a test compound; a labeled compound, for example an antibody having known binding affinity for the antigen; a source of IL-170 protein (naturally occurring or recombinant); and a means for separating bound from free labeled compound, such as a solid phase for immobilizing the antigen. Once compounds are screened, those having suitable binding affinity to the antigen can be evaluated in suitable biological assays, as are well known in the art, to determine whether they exhibit similar biological activities to the natural antigen. The availability of recombinant IL-170 protein polypeptides also provide well defined standards for calibrating such assays.

A preferred kit for determining the concentration of, for example, an IL-170 protein in a sample would typically comprise a labeled compound, e.g., antibody, having known binding affinity for the antigen, a source of antigen (naturally occurring or recombinant) and a means for separating the bound from free labeled compound, for example, a solid phase for immobilizing the IL-170 protein. Compartments containing reagents, and instructions, will normally be provided.

One method for determining the concentration of IL-170 protein in a sample would typically comprise the steps of: (1) preparing membranes from a sample comprised of a membrane bound IL-170 protein source; (2) washing the membranes and suspending them in a buffer; (3) solubilizing the antigen by incubating the membranes in a culture medium to which a suitable detergent has been added; (4) adjusting the detergent concentration of the solubilized antigen; (5) contacting and incubating said dilution with radiolabeled antibody to form complexes; (6) recovering the complexes such as by filtration through polyethyleneimine treated filters; and (7) measuring the radioactivity of the recovered complexes.

Antibodies, including antigen binding fragments, specific for the IL-170 protein or fragments are useful in diagnostic applications to detect the presence of elevated levels of IL-170 protein and/or its fragments. Such diagnostic assays can employ lysates, live cells, fixed cells, immunofluorescence, cell cultures, body fluids, and further can involve the detection of antigens related to the protein in serum, or the like. Diagnostic assays may be homogeneous (without a separation step between free reagent and protein-protein complex) or heterogeneous (with a separation step). Various commercial assays exist, such as radioimmunoassay (RIA), enzyme-linked immunosorbent assay (ELISA), enzyme immunoassay (EIA), enzyme-multiplied immunoassay technique (EMIT), substrate-labeled fluorescent immunoassay (SLFIA), and the like. For example, unlabeled antibodies can be employed by using a second antibody which is labeled and which recognizes the antibody to an IL-170 protein or to a particular fragment thereof. Similar assays have also been extensively discussed in the literature. See, e.g., Harlow and Lane (1988) *Antibodies: A Laboratory Manual*, CSH.

Anti-idiotypic antibodies may have similar use to diagnose presence of antibodies against an IL-170 protein, as such may be diagnostic of various abnormal states. For example, overproduction of IL-170 protein may result in production of various immunological reactions which may be diagnostic of abnormal physiological states, particularly in proliferative cell conditions such as cancer or abnormal differentiation.

Frequently, the reagents for diagnostic assays are supplied in kits, so as to optimize the sensitivity of the assay. For the subject invention, depending upon the nature of the assay, the protocol, and the label, either labeled or unlabeled antibody, or labeled IL-170 protein is provided. This is usually in conjunction with other additives, such as buffers, stabilizers, materials necessary for signal production such as substrates for enzymes, and the like. Preferably, the kit will also contain instructions for proper use and disposal of the contents after use. Typically the kit has compartments for each useful reagent. Desirably, the reagents are provided as a dry lyophilized powder, where the reagents may be reconstituted in an aqueous medium providing appropriate concentrations of reagents for performing the assay.

Any of the aforementioned constituents of the drug screening and the diagnostic assays may be used without modification or may be modified in a variety of ways. For example, labeling may be achieved by covalently or non-covalently joining a moiety which directly or indirectly provides a detectable signal. In any of these assays, the antigen, test compound, IL-170 protein, or antibodies thereto can be labeled either directly or indirectly. Possibilities for direct labeling include label groups: radiolabels such as $^{125}$I, enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Possibilities for indirect labeling include biotinylation of one constituent followed by binding to avidin coupled to one of the above label groups.

There are also numerous methods of separating the bound from the free antigen, or alternatively the bound from the free test compound. The IL-170 protein can be immobilized on various matrixes followed by washing. Suitable matrixes include plastic such as an ELISA plate, filters, and beads. Methods of immobilizing the IL-170 protein to a matrix include, without limitation, direct adhesion to plastic, use of a capture antibody, chemical coupling, and biotin-avidin. The last step in this approach involves the precipitation of protein-protein complex by any of several methods including those utilizing, e.g., an organic solvent such as polyethylene glycol or a salt such as ammonium sulfate. Other suitable separation techniques include, without limitation, the fluorescein antibody magnetizable particle method described in Rattle, et al. (1984) *Clin. Chem.* 30:1457-1461, and the double antibody magnetic particle separation as described in U.S. Pat. No. 4,659,678.

The methods for linking proteins or their fragments to the various labels have been extensively reported in the literature and do not require detailed discussion here. Many of the techniques involve the use of activated carboxyl groups either through the use of carbodiimide or active esters to form peptide bonds, the formation of thioethers by reaction of a mercapto group with an activated halogen such as chloroacetyl, or an activated olefin such as maleimide, for linkage, or the like. Fusion proteins will also find use in these applications.

Another diagnostic aspect of this invention involves use of oligonucleotide or polynucleotide sequences taken from the sequence of an IL-170 protein. These sequences can be used as probes for detecting levels of antigen message in samples from patients suspected of having an abnormal condition, e.g., cancer or developmental problem. The preparation of both RNA and DNA nucleotide sequences, the labeling of the sequences, and the preferred size of the sequences has received ample description and discussion in the literature. Normally an oligonucleotide probe should have at least about 14 nucleotides, usually at least about 18 nucleotides, and the polynucleotide probes may be up to several kilobases. Various labels may be employed, most commonly radionuclides, particularly $^{32}$P. However, other techniques may also be employed, such as using biotin modified nucleotides for introduction into a polynucleotide. The biotin then serves as the site for binding to avidin or antibodies, which may be labeled with a wide variety of labels, such as radionuclides, fluorescers, enzymes, or the like. Alternatively, antibodies may be employed which can recognize specific duplexes, including DNA duplexes, RNA duplexes, DNA-RNA hybrid duplexes, or DNA-protein duplexes. The antibodies in turn may be labeled and the assay carried out where the duplex is bound to a surface, so that upon the formation of duplex on the surface, the presence of antibody bound to the duplex can be detected. The use of probes to the novel anti-sense RNA may be carried out in any conventional techniques such as nucleic acid hybridization, plus and minus screening, recombinational probing, hybrid released translation (HRT), and hybrid arrested translation (HART). This also includes amplification techniques such as polymerase chain reaction (PCR). Another approach utilizes, e.g., antisense nucleic acid, including the introduction of double stranded RNA (dsRNA) to genetically interfere with gene function as described, e.g., in Misquitta, et al. (1999) *Proc. Nat'l Acad. Sci. USA*

96:1451-1456, and/or ribozymes to block translation of a specific IL-70 mRNA. The use of antisense methods to inhibit the in vitro translation of genes is well known in the art. Marcus-Sakura (1988) *Anal. Biochem.* 172:289; Akhtar (ed. 1995) *Delivery Strategies for Antisense Oligonucleotide Therapeutics* CRC Press, Inc.

Diagnostic kits which also test for the qualitative or quantitative presence of other markers are also contemplated. Diagnosis or prognosis may depend on the combination of multiple indications used as markers. Thus, kits may test for combinations of markers. See, e.g., Viallet, et al. (1989) *Progress in Growth Factor Res.* 1:89-97.

The broad scope of this invention is best understood with reference to the following examples, which are not intended to limit the invention to specific embodiments.

EXAMPLES

I. General Methods

Some of the standard methods are described or referenced, e.g., in Maniatis, et al. (1982) *Molecular Cloning, A Laboratory Manual*, Cold Spring Harbor Laboratory, Cold Spring Harbor Press; Sambrook, et al. (1989) *Molecular Cloning: A Laboratory Manual*, (2d ed.), vols. 1-3, CSH Press, NY; Ausubel, et al., *Biology*, Greene Publishing Associates, Brooklyn, N.Y.; or Ausubel, et al. (1987 and Supplements) *Current Protocols in Molecular Biology*, Greene/Wiley, New York; Innis, et al. (eds. 1990) *PCR Protocols: A Guide to Methods and Applications* Academic Press, N.Y.; and Kohler, et al. (1995) *Quantitation of mRNA by Polymerase Chain Reaction* Springer-Verlag, Berlin. Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification" in *Methods in Enzymology*, vol. 182, and other volumes in this series; and manufacturer's literature on use of protein purification products, e.g., Pharmacia, Piscataway, N.J., or Bio-Rad, Richmond, Calif. Combination with recombinant techniques allow fusion to appropriate segments, e.g., to a FLAG sequence or an equivalent which can be fused via a protease-removable sequence. See, e.g., Hochuli (1989) *Chemische Industrie* 12:69-70; Hochuli (1990) "Purification of Recombinant Proteins with Metal Chelate Absorbent" in Setlow (ed.) *Genetic Engineering, Principle and Methods* 12:87-98, Plenum Press, N.Y.; and Crowe, et al. (1992) *QIAexpress: The High Level Expression & Protein Purification System* QUIAGEN, Inc., Chatsworth, Calif.

Also incorporated herein by reference is a similar patent application directed to the IL-171 and IL-175 cytokines, Attorney Docket Number DX0918K, filed on the same date as this.

Standard immunological techniques are described, e.g., in Hertzenberg, et al. (eds. 1996) *Weir's Handbook of Experimental Immunology* vols. 1-4, Blackwell Science; Coligan (1991) *Current Protocols in Immunology* Wiley/Greene, NY; and *Methods in Enzymology* vols. 70, 73, 74, 84, 92, 93, 108, 116, 121, 132, 150, 162, and 163. Cytokine assays are described, e.g., in Thomson (ed. 1998) *The Cytokine Handbook* (3d ed.) Academic Press, San Diego; Mire-Sluis and Thorpe (1998) *Cytokines* Academic Press, San Diego; Metcalf and Nicola (1995) *The Hematopoietic Colony Stimulating Factors* Cambridge University Press; and Aggarwal and Gutterman (1991) *Human Cytokines* Blackwell Pub.

Assays for vascular biological activities are well known in the art. They will cover angiogenic and angiostatic activities in tumor, or other tissues, e.g., arterial smooth muscle proliferation (see, e.g., Koyoma, et al. (1996) *Cell* 87:1069-1078), monocyte adhesion to vascular epithelium (see McEvoy, et al. (1997) *J. Exp. Med.* 185:2069-2077), etc. See also Ross (1993) *Nature* 362:801-809; Rekhter and Gordon (1995) *Am. J. Pathol.* 147:668-677; Thyberg, et al. (1990) *Atherosclerosis* 10:966-990; and Gumbiner (1996) *Cell* 84:345-357.

Assays for neural cell biological activities are described, e.g., in Wouterlood (ed. 1995) *Neuroscience Protocols* modules 10, Elsevier; *Methods in Neurosciences* Academic Press; and *Neuromethods* Humana Press, Totowa, N.J. Methodology of developmental systems is described, e.g., in Meisami (ed.) *Handbook of Human Growth and Developmental Biology* CRC Press; and Chrispeels (ed.) *Molecular Techniques and Approaches in Developmental Biology* Interscience.

Computer sequence analysis is performed, e.g., using available software programs, including those from the GCG (U. Wisconsin) and GenBank sources. Public sequence databases were also used, e.g., from GenBank and others.

Many techniques applicable to IL-17 may be applied to these new entities, as described, e.g., in U.S. Ser. No. 08/432, 994, which is incorporated herein by reference for all purposes.

FACS analyses are described in Melamed, et al. (1990) *Flow Cytometry and Sorting* Wiley-Liss, Inc., New York, N.Y.; Shapiro (1988) *Practical Flow Cytometry* Liss, New York, N.Y.; and Robinson, et al. (1993) *Handbook of Flow Cytometry Methods* Wiley-Liss, New York, N.Y.

II. Isolation of a DNA Clone Encoding IL-170 Protein

Isolation of murine CTLA-8 is described in Rouvier, et al. (1993) *J. Immunol.* 150:5445-5456. Similar methods are available for isolating species counterparts of the IL-173, IL-174, IL-176, and IL-177, along with the IL-171. IL-172, and IL-175.

Source of the IL-170 Messages

Various cell lines are screened using an appropriate probe for high level message expression. Appropriate cell lines are selected based upon expression levels of the appropriate IL-170 message.

Isolation of an IL-170 Encoding Clone

Standard PCR techniques are used to amplify an IL-170 gene sequence from a genomic or cDNA library, or from mRNA. A human genomic or cDNA library is obtained and screened with an appropriate cDNA or synthetic probe. PCR primers may be prepared. Appropriate primers are selected, e.g., from the sequences provided, and a full length clone is isolated. Various combinations of primers, of various lengths and possibly with differences in sequence, may be prepared. The full length clone can be used as a hybridization probe to screen for other homologous genes using stringent or less stringent hybridization conditions.

In another method, oligonucleotides are used to screen a library. In combination with polymerase chain reaction (PCR) techniques, synthetic oligonucleotides in appropriate orientations are used as primers to select correct clones from a library.

III. Biochemical Characterization of IL-170 Proteins

An IL-170 protein is expressed in heterologous cells, e.g., the native form or a recombinant form displaying the FLAG peptide at the carboxy terminus. See, e.g., Crowe, et al. (1992) *QIAexpress: The High Level Expression and Protein Purification System* QIAGEN, Inc. Chatsworth, Calif.; and Hopp, et al. (1988) *Bio/Technology* 6:1204-1210. These two forms are introduced into expression vectors, e.g., pME18S or pEE12, and subsequently transfected into appropriate cells, e.g., COS-7 or NSO cells, respectively. Electroporated cells are cultivated, e.g., for 48 hours in RPMI medium supplemented with 10% Fetal Calf Serum. Cells are then incubated with $^{35}$S-Met and $^{35}$S-Cys in order to label cellular proteins. Comparison of the proteins under reducing conditions on SDS-PAGE should show that cells transfected with full length clones should secret a polypeptide of the appropriate size, e.g., about 15,000 daltons. Treatment with endoglycosidases will demonstrate whether there are N-glycosylated forms.

IV. Large Scale Production, Purification of IL-170s

For biological assays, mammalian IL-170 is produced in large amounts, e.g., with transfected COS-7 cells grown in RPMI medium supplemented with 1% Nutridoma HU (Boehringer Mannheim, Mannheim, Germany) and subsequently purified. Purification may use affinity chromatography using antibodies, or protein purification techniques, e.g., using antibodies to determine separation properties.

In order to produce larger quantities of native proteins, stable transformants of NSO cells can be prepared according to the methodology developed by Celltech (Slough, Berkshire, UK; International Patent Applications WO86/05807, WO87/04462, WO89/01036, and WO89/10404).

Typically, 1 liter of supernatant containing, e.g., human IL-173 or IL-173-FLAG is passed, e.g., on a 60 ml column of $Zn^{++}$ ions grafted to a Chelating Sepharose Fast Flow matrix (Pharmacia, Upsalla, Sweden). After washing with 10 volumes of binding buffer (His-Bind Buffer kit, Novagen, Madison, Wis.), the proteins retained by the metal ions are eluted with a gradient of 20-100 mM Imidazole. The content of human IL-173-FLAG in the eluted fractions is determined by dot blot using the anti-FLAG monoclonal antibody M2 (Eastman Kodak, New Haven, Conn.), whereas the content of human IL-173 is assessed, e.g., by silver staining of non-reducing SDS-PAGE. The IL-170 containing fractions are then pooled and dialyzed against PBS, and are either used in biological assays or further purified, e.g., by anion exchange HPLC on a DEAE column. A third step of gel filtration chromatography may be performed on a SUPERDEX G-75 HRD30 column (Pharmacia Uppsala, Sweden). Purification may be evaluated, e.g., by silver stained SDS-PAGE.

V. Preparation of Antibodies Against IL-173

Inbred Balb/c mice are immunized intraperitoneally, e.g., with 1 ml of purified human IL-173-FLAG emulsified in Freund's complete adjuvant on day 0, and in Freund's incomplete adjuvant on days 15 and 22. The mice are boosted with 0.5 ml of purified human IL-173 administered intravenously.

Polyclonal antiserum is collected. The serum can be purified to antibodies. The antibodies can be further processed, e.g., to Fab, Fab2, Fv, or similar fragments.

Hybridomas are created using, e.g., the non-secreting myeloma cells line SP2/0-Ag8 and polyethylene glycol 1000 (Sigma, St. Louis, Mo.) as the fusing agent. Hybridoma cells are placed in a 96-well Falcon tissue culture plate (Becton Dickinson, NJ) and fed with DMEM F12 (Gibco, Gaithersburg, Md.) supplemented with 80 µg/ml gentamycin, 2 mM glutamine, 10% horse serum (Gibco, Gaithersburg, Md.), 1% ADCM (CRTS, Lyon, France) $10^{-5}$ M azaserine (Sigma, St. Louis, Mo.) and $5 \times 10^{-5}$ M hypoxanthine. Hybridoma supernatants are screened for antibody production against human IL-173 by immunocytochemistry (ICC) using acetone fixed human IL-173 transfected COS-7 cells and by ELISA using human IL-173-FLAG purified from COS-7 supernatants as a coating antigen. Aliquots of positive cell clones are expanded for 6 days and cryopreserved as well as propagated in ascites from pristane (2,6,10,14-teramethylpentadecane, Sigma, St. Louis, Mo.) treated Balb/c mice who had received on intraperitoneal injection of pristane 15 days before. Typically, about $10^5$ hybridoma cells in 1 ml of PBS are given intraperitoneally, and 10 days later, ascites are collected from each mouse.

After centrifugation of the ascites, the antibody fraction is isolated by ammonium sulfate precipitation and anion-exchange chromatography on a Zephyr-D silicium column (IBF Sepracor) equilibrated with 20 mM Tris pH 8.0. Proteins are eluted with a NaCl gradient (ranging from 0 to 1 M NaCl). 2 ml fractions are collected and tested by ELISA for the presence of anti-IL-173 antibody. The fractions containing specific anti-IL-173 activity are pooled, dialyzed, and frozen. Aliquots of the purified monoclonal antibodies may be peroxidase labeled.

Antibody preparations, polyclonal or monoclonal, may be cross absorbed, depleted, or combined to create reagents which exhibit desired combinations of selectivities and specificities. Defined specific antigens can be immobilized to a solid matrix and used to selectively deplete or select for desired binding capacities.

VI. Quantification of Human IL-173

Among the antibodies specific for IL-173, appropriate clonal isolates are selected to quantitate levels of human IL-173 using a sandwich assay. Purified antibodies are diluted, e.g., at 2 µg/ml in coating buffer (carbonate buffer, pH 9.6. 15 mM $Na_2CO_3$, 35 mM $NaHCO_3$). This diluted solution is coated onto the wells of a 96-well ELISA plate (Immunoplate Maxisorp F96 certified, NUNC, Denmark) overnight at room temperature. The plates are then washed manually, e.g., with a washing buffer consisting of Phosphate Buffered Saline and 0.05% Tween 20 (Technicon Diagnositics, USA). 110 µl of purified human CTLA-8 diluted in TBS-B-T buffer [20 mM Tris, 150 mM NaCl, 1% BSA (Sigma, St. Louis, Mo.), and 0.05% Tween 20] is added to each well. After 3 hours of incubation at 37° C., the plates are washed once. 100 µl of peroxidase labeled Ab diluted to 5 µg/ml in TBS-B-T buffer is added to each well, and incubated for 2 hours at 37° C. The wells are then washed three times in washing buffer. 100 µl of peroxidase substrate, 2.2° Azino-bis(3 ethylbenzthiazoine-6-sulfonic acid) (ABTS), diluted to 1 mg/ml in citrate/phosphate buffer, is added to each well, and the colorimetric reaction read at 405 nm.

VII. Distribution of IL-170 Genes

The human IL-173 was identified from sequence derived from a cDNA library from an epileptic brain frontal cortex. The rat IL-173 was derived from a cDNA library from cochlea, brain, cerebellum, eye, lung, and kidney. Again, the genes appear to be quite rare, which suggests the expression distributions would be highly restricted.

The mouse IL-174 was identified from sequence derived from a cDNA library derived form a mouse embryo. The gene appears to be quite rare, which suggests the expression distribution would be highly restricted.

The human IL-171 was identified from a sequence derived from an apoptotic T cell. The gene appears to be quite rare, which suggests the expression distribution would be highly restricted.

The human IL-172 was identified from sequences derived from human fetal heart, liver and spleen, thymus, thymus tumor, and total fetus. Mouse was derived from sequences derived from mouse, embryo, mammary gland, and pooled organs. Both genes appear to be quite rare, which suggests their expression distribution would be highly restricted.

The human IL-175 was identified from a sequence derived from a 12 h thiouridine activated T cell. The gene appears to be quite rare, which suggests the expression distribution would be highly restricted.

VIII. Chromosome Mapping of IL-170 Genes

An isolated cDNA encoding the appropriate IL-170 gene is used. Chromosome mapping is a standard technique. See, e.g., BIOS Laboratories (New Haven, Conn.) and methods for using a mouse somatic cell hybrid panel with PCR.

The human IL-173 gene maps to human chromosome 13q11.

IX. Isolating IL-170 Homologues

A binding composition, e.g., antibody, is used for screening of an expression library made from a cell line which expresses an IL-170 protein. Standard staining techniques are used to detect or sort intracellular or surface expressed antigen, or surface expressing transformed cells are screened by panning. Screening of intracellular expression is performed by various staining or immunofluorescence procedures. See also McMahan, et al. (1991) *EMBO J.* 10:2821-2832.

Similar methods are applicable to isolate either species or allelic variants. Species variants are isolated using cross-species hybridization techniques based upon a full length isolate or fragment from one species as a probe, or appropriate species.

X. Isolating Receptors for IL-170

Methods are available for screening of an expression library made from a cell line which expresses potential IL-170 receptors. A labeled IL-170 ligand is produced, as described above. Standard staining techniques are used to detect or sort surface expressed receptor, or surface expressing transformed cells are screened by panning. See also McMahan, et al. (1991) *EMBO J.* 10:2821-2832.

For example, on day 0, precoat 2-chamber permanox slides with 1 ml per chamber of fibronectin, 10 ng/ml in PBS, for 30 min at room temperature. Rinse once with PBS. Then plate COS cells at 2-3×10$^5$ cells per chamber in 1.5 ml of growth media. Incubate overnight at 37° C.

On day 1 for each sample, prepare 0.5 ml of a solution of 66 µg/ml DEAE-dextran, 66 µM chloroquine, and 4 µg DNA in serum free DME. For each set, a positive control is prepared, e.g., of huIL-170-FLAG cDNA at 1 and 1/200 dilution, and a negative mock. Rinse cells with serum free DME. Add the DNA solution and incubate 5 hr at 37° C. Remove the medium and add 0.5 ml 10% DMSO in DME for 2.5 min. Remove and wash once with DME. Add 1.5 ml growth medium and incubate overnight.

On day 2, change the medium. On days 3 or 4, the cells are fixed and stained. Rinse the cells twice with Hank's Buffered Saline Solution (HBSS) and fix in 4% paraformaldehyde (PFA)/glucose for 5 min. Wash 3× with HESS. The slides may be stored at −80° C. after all liquid is removed. For each chamber, 0.5 ml incubations are performed as follows. Add HBSS/saponin (0.1%) with 32 µl/ml of 1 M NaN$_3$ for 20 min. Cells are then washed with HESS/saponin 1×. Soluble antibody is added to cells and incubate for 30 min. Wash cells twice with HBSS/saponin. Add second antibody, e.g., Vector anti-mouse antibody, at 1/200 dilution, and incubate for 30 min. Prepare ELISA solution, e.g., Vector Elite ABC horseradish peroxidase solution, and preincubate for 30 min. Use, e.g., 1 drop of solution A (avidin) and 1 drop solution B (biotin) per 2.5 ml HBSS/saponin. Wash cells twice with HBSS/saponin. Add ABC HRP solution and incubate for 30 min. Wash cells twice with HBSS, second wash for 2 min, which closes cells. Then add Vector diaminobenzoic acid (DAB) for 5 to 10 min. Use 2 drops of buffer plus 4 drops DAB plus 2 drops of H$_2$O$_2$ per 5 ml of glass distilled water. Carefully remove chamber and rinse slide in water. Air dry for a few minutes, then add 1 drop of Crystal Mount and a cover slip. Bake for 5 min at 85-90° C.

Alternatively, the labeled ligand is used to affinity purify or sort out cells expressing the receptor. See, e.g., Sambrook, et al. or Ausubel, et al.

All references cited herein are incorporated herein by reference to the same extent as if each individual publication or patent application was specifically and individually indicated to be incorporated by reference.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. An isolated nucleic acid encoding an IL-174 polypeptide, wherein the polypeptide comprises: SEQ ID NO:18.
2. The isolated nucleic acid of claim 1, wherein the IL-174 polypeptide consists of SEQ ID NO:18 and the nucleic acid comprises nucleotides 1-507 of SEQ ID NO:17.
3. The isolated nucleic acid of claim 2, which is an expression vector.
4. The isolated nucleic acid of claim 1, which is an expression vector.
5. An isolated cell containing the expression vector of claim 4.
6. The cell of claim 5, which is a prokaryotic cell.
7. The cell of claim 5, which is a eukaryotic cell.
8. The cell of claim 7, which is a mammalian cell.
9. The cell of claim 5, wherein the expression vector comprises nucleotides 1-507 of SEQ ID NO:17.
10. A method of making an IL-174 polypeptide comprising expressing the expression vector of claim 4, thereby producing the IL-174 polypeptide.
11. The method of claim 10, wherein the IL-174 polypeptide consists of SEQ ID NO:18, and the expression vector comprises nucleotides 1-507 of SEQ ID NO:17.

* * * * *